US009737707B2

(12) United States Patent
Haessler et al.

(10) Patent No.: US 9,737,707 B2
(45) Date of Patent: Aug. 22, 2017

(54) DEVICES AND METHODS FOR STIMULATING NERVES

(71) Applicant: FemPulse, LLC, Incline Village, NV (US)

(72) Inventors: Alexandra Haessler, Larkspur, CA (US); Bruno Strul, Portola Valley, CA (US)

(73) Assignee: FemPulse, LLC, Incline Village, NV (US)

( * ) Notice: Subject to any disclaimer, the term of this patent is extended or adjusted under 35 U.S.C. 154(b) by 0 days.

(21) Appl. No.: 15/008,758

(22) Filed: Jan. 28, 2016

(65) Prior Publication Data

US 2016/0256685 A1    Sep. 8, 2016

Related U.S. Application Data

(63) Continuation of application No. 14/101,336, filed on Dec. 9, 2013, now Pat. No. 9,248,285, which is a continuation-in-part of application No. 14/056,937, filed on Oct. 17, 2013, now Pat. No. 9,381,351, which is a continuation-in-part of application No. 13/913,390, filed on Jun. 8, 2013, now abandoned,
(Continued)

(51) Int. Cl.
| | |
|---|---|
| *A61N 1/18* | (2006.01) |
| *A61N 1/36* | (2006.01) |
| *A61B 5/04* | (2006.01) |
| *A61B 5/053* | (2006.01) |
| *A61N 1/05* | (2006.01) |
| *A61N 1/375* | (2006.01) |
| *A61N 1/372* | (2006.01) |

(52) U.S. Cl.
CPC ............ *A61N 1/36007* (2013.01); *A61B 5/04* (2013.01); *A61B 5/053* (2013.01); *A61N 1/0524* (2013.01); *A61N 1/0551* (2013.01); *A61N 1/0556* (2013.01); *A61N 1/36071* (2013.01); *A61N 1/3756* (2013.01); *A61M 2210/1017* (2013.01); *A61N 1/0514* (2013.01); *A61N 1/36017* (2013.01); *A61N 1/36107* (2013.01); *A61N 1/37205* (2013.01)

(58) Field of Classification Search
CPC . A61N 1/36071; A61N 1/36007; A61N 1/326
USPC .......................................................... 607/39
See application file for complete search history.

(56) References Cited

U.S. PATENT DOCUMENTS

| | | |
|---|---|---|
| 4,515,167 A | 5/1985 | Hochman |
| 4,607,639 A | 8/1986 | Tanagho et al. |

(Continued)

FOREIGN PATENT DOCUMENTS

| | | |
|---|---|---|
| WO | 99/22680 | 5/1999 |
| WO | 2011/103473 | 8/2011 |

*Primary Examiner* — Carl H Layno
*Assistant Examiner* — Jon Eric C Morales
(74) *Attorney, Agent, or Firm* — Jens Hoekendijk

(57) ABSTRACT

A device for stimulating nerves adjacent the vagina includes a nerve stimulating element coupled to a main body. The nerve stimulating element is positioned and designed to stimulate the vesical, Frankenhauser's and/or inferior hypogastric plexuses. The device may reside in the vaginal fornices. An implant is also provided which has a nerve stimulating element in contact with a uterosacral ligament. The device positioned in the vagina may be used to charge a power source for an implant which may be a capacitor.

2 Claims, 65 Drawing Sheets

Related U.S. Application Data which is a continuation-in-part of application No. 13/844,472, filed on Mar. 15, 2013, now Pat. No. 8,914,111, which is a continuation-in-part of application No. 13/492,855, filed on Jun. 9, 2012, now Pat. No. 8,788,040.

(56) References Cited

U.S. PATENT DOCUMENTS

| | | |
|---|---|---|
| 4,771,779 A | 9/1988 | Tanagho et al. |
| 4,827,946 A | 5/1989 | Kaali et al. |
| 4,881,526 A | 11/1989 | Johnson et al. |
| 4,909,263 A | 3/1990 | Norris |
| 4,955,378 A | 9/1990 | Grasso |
| 5,036,867 A | 8/1991 | Biswas |
| 5,370,671 A | 12/1994 | Maurer et al. |
| 5,662,699 A | 9/1997 | Hamedi et al. |
| 5,702,428 A | 12/1997 | Tippey et al. |
| 6,055,456 A | 4/2000 | Gerber |
| 6,086,549 A | 7/2000 | Neese et al. |
| 6,185,465 B1 | 2/2001 | Mo et al. |
| 6,356,777 B1 | 3/2002 | Garfield et al. |
| 6,402,683 B1 | 6/2002 | Marty |
| 6,418,930 B1 | 7/2002 | Fowler |
| 6,428,467 B1 | 8/2002 | Benderev |
| 6,432,037 B1 | 8/2002 | Eini et al. |
| 6,445,955 B1 | 9/2002 | Michelson et al. |
| 6,526,980 B1 | 3/2003 | Tracy et al. |
| 6,625,495 B1 | 9/2003 | Alon et al. |
| 6,741,895 B1 | 5/2004 | Gafni et al. |
| 6,905,471 B2 | 6/2005 | Leivseth et al. |
| 6,964,643 B2 | 11/2005 | Hovland et al. |
| 7,079,882 B1 | 7/2006 | Schmidt |
| 7,328,068 B2 | 2/2008 | Spinelli et al. |
| 7,369,894 B2 | 5/2008 | Gerber |
| RE41,463 E | 7/2010 | Boutos |
| 7,794,456 B2 | 9/2010 | Sharps et al. |
| 7,957,794 B2 | 6/2011 | Hochman |
| 7,963,977 B2 | 6/2011 | Brockman |
| 8,114,610 B2 | 2/2012 | Fuks et al. |
| 8,452,407 B2 | 5/2013 | Whitehurst et al. |
| 8,467,875 B2 | 6/2013 | Bennett et al. |
| 8,788,040 B2 | 7/2014 | Haessler |
| 8,914,111 B2 | 12/2014 | Haessler |
| 2004/0030360 A1 | 2/2004 | Eini et al. |
| 2005/0010260 A1* | 1/2005 | Gerber ............... A61N 1/36071 607/39 |
| 2005/0113877 A1 | 5/2005 | Spinelli et al. |
| 2005/0240229 A1* | 10/2005 | Whitehurst ........ A61N 1/36007 607/2 |
| 2005/0251134 A1* | 11/2005 | Woloszko ............ A61B 18/149 606/46 |
| 2005/0256423 A1 | 11/2005 | Kirsner et al. |
| 2007/0142746 A1 | 6/2007 | Scampini |
| 2008/0171950 A1 | 7/2008 | Franco |
| 2008/0177398 A1 | 7/2008 | Gross et al. |
| 2008/0300650 A1 | 12/2008 | Gerber et al. |
| 2009/0036945 A1 | 2/2009 | Chancellor |
| 2009/0076565 A1 | 3/2009 | Surwit |
| 2009/0171425 A1 | 7/2009 | Dahlberg |
| 2009/0222058 A1 | 9/2009 | Craggs |
| 2009/0228067 A1 | 9/2009 | Boyd et al. |
| 2009/0270963 A1 | 10/2009 | Pelger et al. |
| 2010/0106216 A1 | 4/2010 | Cha et al. |
| 2011/0105876 A1 | 5/2011 | Zhang |
| 2011/0202108 A1 | 8/2011 | Gross et al. |
| 2012/0101326 A1 | 4/2012 | Simon et al. |
| 2012/0215280 A1 | 8/2012 | Peddicord |
| 2012/0245652 A1 | 9/2012 | Whitehurst et al. |
| 2013/0131772 A1 | 5/2013 | Peddicord |
| 2013/0144191 A1 | 6/2013 | Egorov et al. |
| 2013/0204328 A1 | 8/2013 | Stahmann et al. |

* cited by examiner

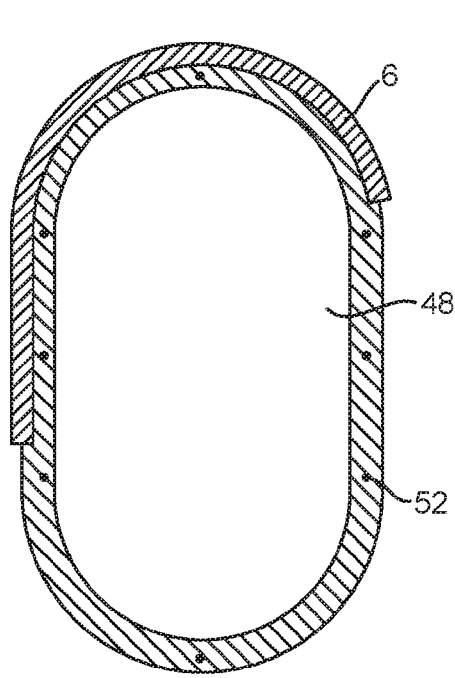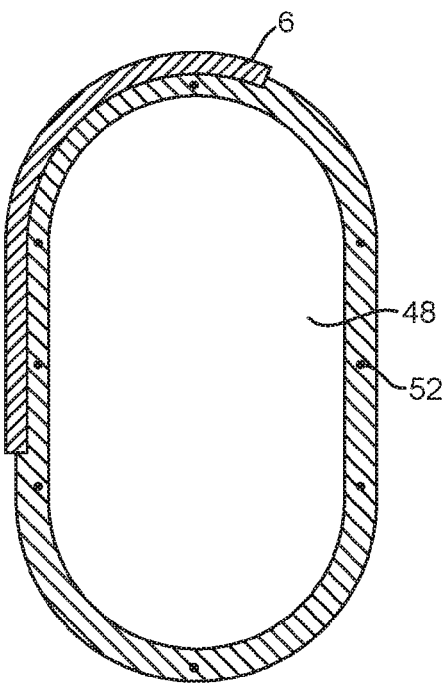
FIG. 14A  FIG. 14B
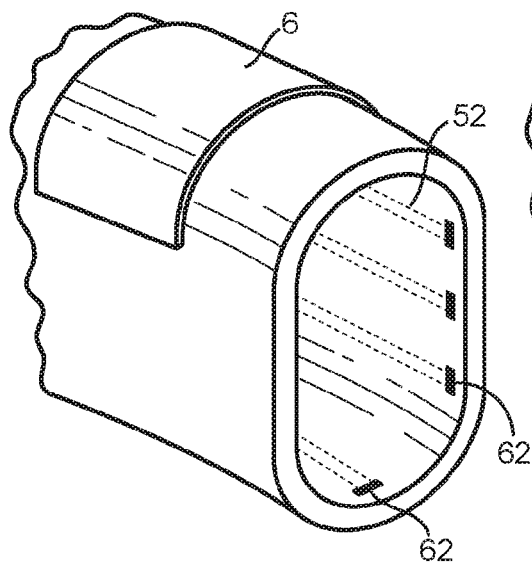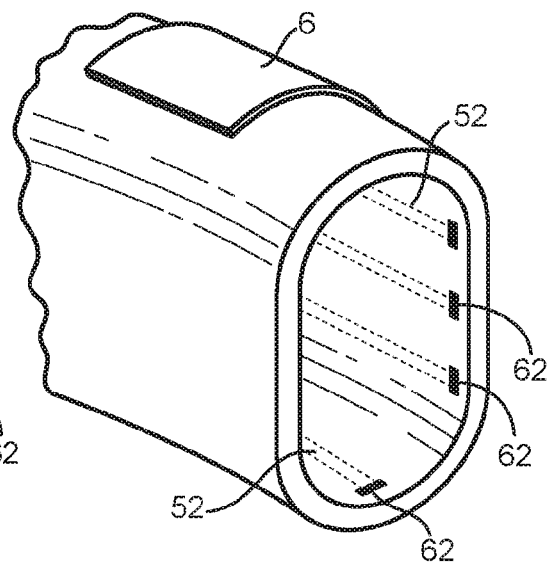
FIG. 15A  FIG. 15B

A-A
battery

B-B
control

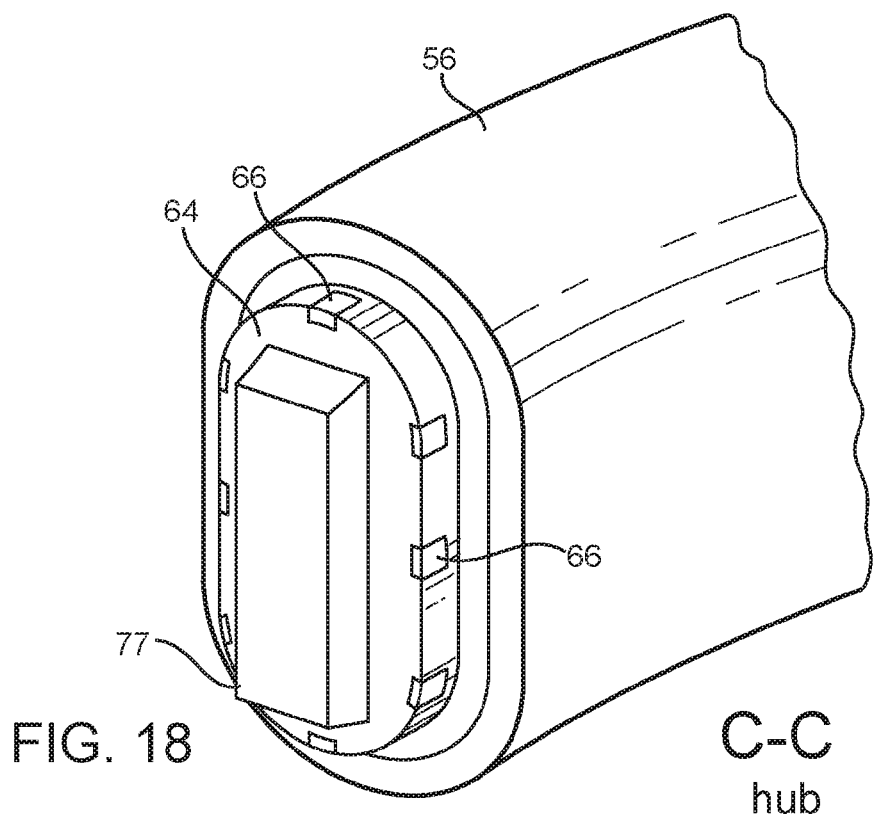
FIG. 18     C-C hub
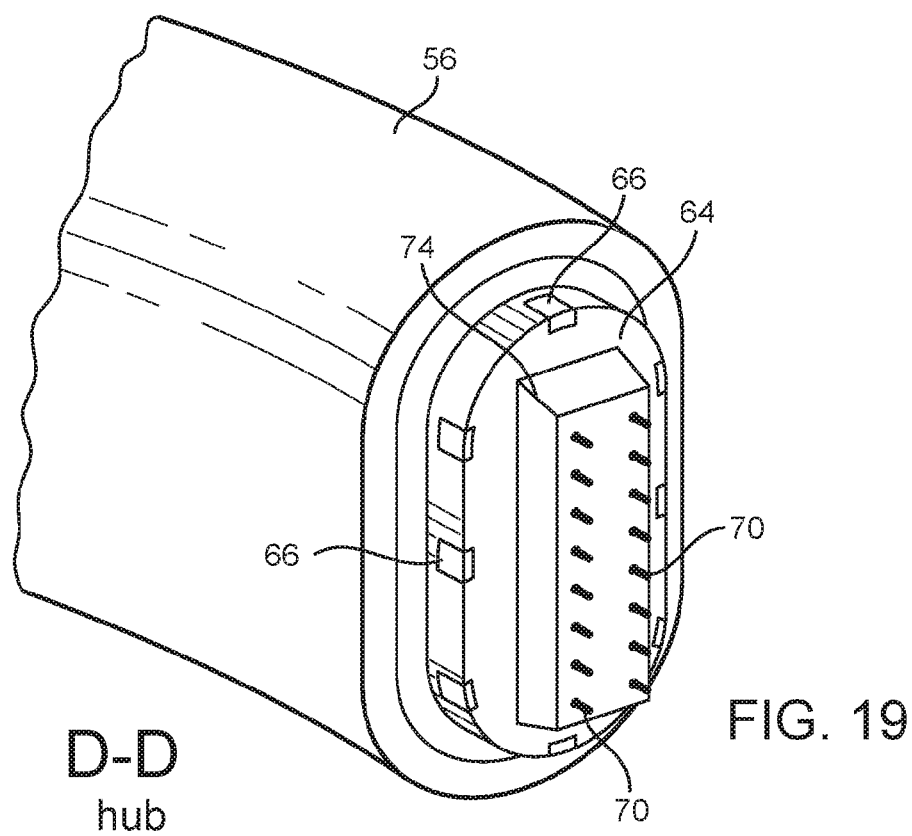
D-D hub     FIG. 19

A-A

B-B

C-C

DEVICES AND METHODS FOR STIMULATING NERVES

CROSS-REFERENCE TO RELATED APPLICATIONS

The present application is a continuation-in-part of U.S. application Ser. No. 14/101,336, filed Dec. 9, 2013, is now U.S. Pat. No. 9,248,285 which is a continuation in part of U.S. application Ser. No. 14/056,937, filed Oct. 17, 2013 is now U.S. Pat. No. 9,381,351 which is a continuation-in-part of U.S. application Ser. No. 13/913,390, (now abandoned) filed Jun. 8, 2013, which is a continuation-in-part of U.S. application Ser. No. 13/844,472, filed Mar. 15, 2013, now U.S. Pat. No. 8,914,111 which is a continuation-in-part of U.S. application Ser. No. 13/492,855, filed Jun. 9, 2012, now U.S. Pat. No. 8,788,040 all by Alexandra Haessler, which are all hereby incorporated by reference.

BACKGROUND

Millions of women suffer from increased urinary urgency, frequency, incontinence, incomplete bladder emptying and irritative bladder conditions. There are two main types of incontinence, urge incontinence and stress incontinence, which have different physiological causes and different treatment options. Many women suffer from mixed incontinence, having both conditions.

Stress incontinence is largely the result of weakened ligaments, pelvic floor tissue and vaginal support, ultimately allowing the urethra to drop open in the setting of increased intraabdominal pressure. The process leading to stress incontinence is primarily mechanical and is associated with supportive tissue under the distal anterior vaginal wall. Strengthening the pelvic floor and supporting the urethra and/or bladder neck are safe and effective treatments for stress incontinence.

Urinary urgency, frequency, urge incontinence, incomplete bladder emptying, and nocturia represent a more complex process that is greatly neurologically mediated. Urinary urgency is marked by a strong, and often uncomfortable, urge to void that is difficult to suppress. Urge incontinence is defined by involuntary leakage of urine in the setting of urgency. The conditions noted above and other irritative bladder conditions may result from abnormal sensitivity of autonomic bladder nerves that prematurely communicate "fullness" to the central nervous system. These conditions may also result from erroneous nerve function in the central nervous system that allows the bladder to empty at inappropriate times. The underlying cause of these problems may be multifactorial. Ultimately, it is the autonomic nervous system that communicates bladder sensation, discomfort, or "fullness" and coordinates bladder filling and emptying.

Incomplete bladder emptying or urinary retention may result from inappropriate autonomic nerve signaling to the urethra and/or bladder. Some medical treatments are aimed at altering autonomic signal to the urethra, such that urethral tone is lessened. Others work by increasing bladder muscle tone by activating autonomic receptors in the bladder to cause a bladder contraction.

Many treatments of irritative bladder conditions are aimed at modifying nerve signaling between the bladder and the central nervous system. The goal is to affect both the afferent signals to the central nervous system that signal irritation, urgency, pressure or a sense of fullness and/or the efferent nerve signal that can trigger a rise in bladder pressure, cause discomfort, or leakage. Autonomic nerves transmit these signals. Treatment for urinary urgency, frequency, nocturia and urge incontinence is multifaceted, attempting to affect nerve signaling with behavioral, dietary, medical and physical therapies.

Urinary urge incontinence medications attempt to inhibit bladder contractions by disrupting signals between the autonomic nerves and the urinary tract. These drugs are not adequately effective for the majority of patients and also have significant systemic side effects that limit usage. Discontinuation rates at 6 months are well over 50% due to the high cost, lack of adequate effectiveness, and side effects. There are also contraindications to use, most of which are conditions affecting the elderly population that desires treatment for lower urinary tract symptoms.

An aggressive pelvic floor physical therapy regimen incorporating education, lifestyle, and dietary changes along with pelvic floor exercise training can be a reasonably effective treatment for urgency, frequency and urge incontinence in some patients. It is not clear how well exercise alone works to control urge related symptoms, as a large portion of the benefit gained from physical therapy is the result of education, cognitive-behavioral techniques, diet and lifestyle change. Patients are not often compliant beyond the short term, as the regimen can be costly, time consuming and difficult to comply with over time.

The goal of most pelvic floor exercises is to strengthen the muscles of the pelvic floor and increase nerve "tone." These exercises activate the somatic nerves in order to cause pelvic floor muscle contraction. This is primarily a treatment for stress incontinence. A pelvic floor muscle contraction can secondarily affect autonomic nerves to the bladder via a spinal cord reflex arc. These exercises may dampen the signal to urinate or prevent leakage. They do not necessarily prevent the more common overactive bladder symptoms that occur before one has time to perform a contraction, such as a spontaneous sense of urgency or waking at night to void. It has been shown that urinary urgency alone, without leakage, is more bothersome to patients than urinary leakage alone. Effective treatment needs to prevent the spinal cord from perceiving inappropriate sensations in the first place.

Neuromodulation of autonomic nerves has become a useful treatment method for lower urinary tract symptoms, such as urgency, frequency, incontinence, incomplete bladder emptying, irritative symptoms, incomplete bladder emptying, fecal incontinence and related conditions. One technique involves an implanted stimulation lead over the S3 nerve root. It can be a successful treatment for patients who have failed other treatments.

Although use of the surgical implant over the S3 nerve root has been successful, the treatment has drawbacks. The main disadvantage is that the device requires surgical implantation of small electrical leads through a foramen in the sacrum and a stimulator device within the soft tissue above the gluteus maximus. Implantation typically requires two surgical procedures, exposure to radiation, and often requires additional surgery to revise or remove the components. It has also been reported that over 25% of patients will require surgical revision of either the implanted battery or lead to manage complications. Additionally, the current surgical implant often needs to be removed for some types of MRI. The device is also extremely expensive. In general, patients prefer less effective alternative therapies, as they often do not think bladder symptoms warrant surgery or they are not comfortable with the idea of a surgical implant.

Another drawback of the conventional surgical implant is that the stimulation occurs at the level of the nerve root, so somatic fibers traveling in the S3 nerve root are also stimulated before they branch off into somatic nerves. These nerves can cause the patients to feel vulvar, vaginal, anal and lower extremity muscle contractions or tingling. Still another limitation of the implantable stimulator is that the same one, or occasionally two, nerve roots are available and subject to all of the stimulation. As a result, the nerve becomes less responsive due to habituation rendering the lead less effective or ineffective. This phenomenon has been well established. Due to these many drawbacks, including risk of surgery, complications associated with the implant, cost, reduced effectiveness over time, and somatic symptoms associated with the implanted S3 sacral nerve modulator, this treatment has not been widely adopted despite its effectiveness.

The existing non-surgical electrical stimulation therapies include devices that are positioned in the vagina thereby avoiding some drawbacks of the surgical implant. However, these devices are often less effective and have their own drawbacks. Many conventional devices positioned in the vagina direct electrical impulses in the lower or distal vagina and/or adjacent to the pelvic floor. Electrical signals are sent through the vagina to paravaginal tissue, targeting nerves adjacent the pelvic floor muscles or the muscles themselves. The goal suggested by these conventional methods is generally to stimulate nerves adjacent the pelvic floor and to increase pelvic floor tension. Many of these therapies attempt to treat stress incontinence and/or simulate pelvic floor exercises. Yet, bladder filling, emptying and sensation are mediated by autonomic nerves, not somatic nerves. The inventor believes that these devices and therapies are often not as effective at treating urinary urgency, incontinence, nocturia, incomplete bladder emptying or other lower urinary tract symptoms as an implanted sacral nerve modulator because they do not sufficiently isolate stimulation to autonomic nerves.

A major limitation of these vaginal stimulation devices for treating most irritative urinary tract symptoms is that they indiscriminately send electrical impulses to both somatic and some distal autonomic nerve fibers adjacent to the lower and mid-vagina. They also often target somatic nerves, such as the pudendal nerve and its distal branches. The somatic nerves do not directly control bladder filling, emptying, or sensation. Activation of somatic nerves can cause increased pelvic floor tension, discomfort, and pain associated with pudendal nerve activation. Such conditions may actually contribute to urinary urgency, frequency and voiding dysfunction. Somatic nerves are quite sensitive, so the electrical impulses can be perceived even at low intensity, thereby limiting the full range of treatment protocols or precluding therapy altogether.

Thus, the inventor believes that the problem with present neuromodulation treatment methods is that they either require surgical implantation or, for vaginally inserted devices, the stimulation does not adequately target important autonomic nerve structures yet influences muscles and somatic nerves in the lower vagina providing less effective therapy for autonomically mediated urinary tract symptoms and contributing to undesirable side effects. Furthermore, the conventional implanted sacral nerve root therapies stimulate somatic nerves (although there are also autonomic—parasympathetic fibers near this location) and provide therapy to a very focal portion of a nerve, thereby contributing to habituation. These factors may provide less effective therapy for autonomically mediated urinary tract symptoms and contribute to undesirable side effects. Thus, optimal therapy would stimulate the autonomic nerves that mediate signal between the urinary tract and the central nervous system and/or end organ while avoiding activation of the pelvic floor and associated somatic nerves. Optimally, neuromodulation would be delivered directly to the autonomic nerves at the "gateway" between the urinary tract and the spinal cord while avoiding pelvic floor muscle and nerve activation.

The present invention is also directed to systems and methods for altering and improving (reducing) sympathetic tone. The autonomic nervous system maintains homeostasis and functional control of most organs in the body. The sympathetic arm of the system mediates the "fight or flight" response associated with a stress state, generally via norepinephrine, otherwise known as "adrenaline." The sympathetic system is responsible for preparing animals for immediate action. The parasympathetic arm maintains organ function at rest. It is theorized that survival of early organisms was quite dependent on the ability to quickly adjust from rest (grazing) to extreme physical activity (fleeing a predator). This transition requires immediate coordination of many organs, glands and nerves that increase cardiac output, optimize respiratory function, increase skeletal muscle contractility, alter blood flow distribution, adjust visual depth perception, and trigger rapid-fire thinking. When the sympathetic tone is high, organs are operating at an extreme capacity, which is not healthy over time.

Outside of acute stress, organisms need to maintain a fine balance between the sympathetic and parasympathetic tone. In modern times humans are not often fleeing life-threatening danger. However, we tend to live in a chronic state of stress. Naturally, the sympathetic nervous output is upregulated in a chronic stress state. Chronic stress contributes to persistently elevated sympathetic tone, which has deleterious effects on most organs of the body. For example, the heart is very sensitive to even modest increases in circulating epinephrine. Chronic exposure to increased epinephrine levels results in a rise of blood pressure and heart rate that can contribute to many forms of heart disease, including arrhythmias, coronary artery disease, valvular dysfunction and heart failure. Alterations in cerebral blood flow resulting from stress, influenced by the sympathetic nervous system, can result in migraine headaches.

Metabolism is greatly affected by increased sympathetic tone, via increased release of cortisol. Cortisol is an adrenal hormone that alters metabolism of glucose, bone, muscle, adipose (fat) cells and connective tissue. Cortisol acts locally and systemically to mobilize metabolic resources for a stress response related action. Chronically elevated circulating cortisol levels can have serious and deleterious consequences including insulin resistance/diabetes, decreased bone formation (osteoporosis), inhibited collagen production (poor tissue quality and wound healing), decreased protein synthesis (atrophy), increased gastric acid secretion (ulcers and gastrointestinal bleeding), altered renal function (electrolyte imbalances), impaired hippocampal function (decreased learning ability and dampened memory retrieval), along with increased epinephrine sensitivity in blood vessels (hypertension). Cortisol also weakens the immune response by inhibiting T cell proliferation, which results in vulnerability to infection and cancer.

Stress and elevated sympathetic tone is also associated with increases in circulating inflammatory mediators, mainly Interleukin-6, which promote systemic inflammation. Inflammation is responsible for autoimmune conditions affecting nearly every organ in the body. Examples include dermatologic conditions (eczema), atherosclerosis (coronary artery disease and stroke), gastrointestinal (ulcerative coltis or Crohn's disease), lupus, arthritis, allergic reactions, pericarditis, myocytis, cataracts, pain conditions, interstitial cystitis, vasculitis, glomerulopathies, multiple sclerosis, iritis, asthma, and cancer. Pain is associated with inflammation and stress. Increased mortality has been associated with chronic exposure to increased stress and Interleukin-6 levels.

Many people simply maintain an elevated sympathetic tone, regardless of their stress level. Normal blood pressure and heart rate in healthy and relaxed people varies within a normal range, for example. Central obesity contributes to increased sympathetic output, regardless of stress level or cardiovascular health.

Ultimately, lowering sympathetic tone can improve specific disease states and overall health. Current approaches to decrease sympathetic tone include exercise, weight loss, relaxation techniques, meditation and cognitive behavioral therapies. These approaches are not always effective, achievable or sustainable.

The present invention is directed to improved systems and methods for stimulating nerves. The present invention is also specifically directed to systems and methods for altering sympathetic tone.

SUMMARY

The present invention provides devices and methods for targeting autonomic nerves while minimizing transmission of stimulus to pelvic floor muscles and non-target nerves, specifically, somatic nerves adjacent to the lower or mid-vagina. The present invention is positioned to stimulate autonomic plexuses and autonomic nerves at the "gateway" between the lower urinary tract and the spinal cord while avoiding pelvic floor muscle and nerve activation. In specific embodiments and methods, the present invention targets the inferior hypogastric plexus (or pelvic plexus), left and right Frankenhauser's plexus (or Lee's plexus) and the vesical plexus. These plexuses may, of course, be called by other names such as Lee's plexus as another name for Frankenhauser's plexus without departing from the invention. Furthermore, the Frankenhauser's plexus refers to both left and right Frankenhauser's plexuses collectively. Unless otherwise specified, use of Frankenhauser's plexus or plexuses shall mean both plexuses.

In one aspect of the present invention, a device for stimulating nerves is positioned in the upper half of the vagina, and in specific embodiments in the vaginal fornices, so that the stimulus intended for the target nerves does not adversely influence non-target somatic nerves, such as the pudendal nerve or its branches, adjacent to the distal or lower half of the vagina. Reducing side effects and possible urinary tract symptoms due to stimulating somatic nerves are thereby avoided in accordance with the present invention.

The present invention treats urologic, gynecologic, colorectal and pain conditions in women with neuromodulation of nerves via electrical stimulation (and other modalities) delivered by a unique, self-retained, indwelling vaginal device that resides in the fornices of the vagina (or uppermost portion of the vagina in women without a cervix) and targets specific autonomic plexuses which communicate with associated nerves traveling to and from genitourinary and pelvic structures. The neuromodulation of the present invention stimulates the nerve plexuses to change a signal transmitted by the nerve plexuses to the associated autonomic nerves.

Referring to FIG. 1, autonomic nerve signals traveling to and from the bladder, urethra, rectum, vagina, uterus, peritoneum and other pelvic structures travel through the inferior hypogastric plexus IHP, carrying the signal between pelvic structures and the spinal cord. The inferior hypogastric plexus IHP is the gateway between the visceral (bladder, gynecologic, rectum) organs and the central nervous system. The IHP is a coalescence of both sympathetic and parasympathetic autonomic fibers. The sympathetic fibers run between the thoracic nerve roots (T10-L2) and into the superior hypogastric plexus, then travel towards the IHP via the left and right hypogastric nerves LHN, RHN along the uterosacral ligaments USL. In some cases a portion of the sympathetic fibers may enter the IHP along the undersurface of the cardinal ligaments. These fibers facilitate bladder storage. The parasympathetic nerves travel from the sacral spinal nerve roots (S2-4) in the sacral or pelvic splanchnic nerves, or nervi erigentes towards the pelvic organs, often in association with the pelvic nerve. They facilitate bladder emptying. Sympathetic and parasympathetic fibers coalesce in the IHP over the posterior and lateral surfaces of the upper cervix, just above the vaginal insertion.

Importantly, the vagina terminates at the level of the pericervical ring around the uppermost portion of the cervix, just below the uterosacral ligament USL insertions. The recesses of the most proximal, or uppermost, aspect of the vagina that surround the cervix are called the vaginal fornices VF. The pelvic floor PF surrounds the lower portion of the vagina near the vaginal opening, making the "floor" of the pelvic cavity. The inferior hypogastric plexus IHP is a web-like plexus adjacent to the posterior and lateral cervix at the level of the uterocervical junction and the uterosacral ligament USL insertions, just proximal to the posterior vaginal fornix. Inferior hypogastric plexus IHP fibers also cover the distal uterosacral ligaments and possibly reside in the lower or under-portion of the cardinal ligament just anterior to the USL. For reference, the IHP is generally referred to as a singular structure in the literature, but anatomic studies suggest significant concentrations of these ganglia may be distributed bilaterally, as described above. For purposes of this description and application the IHP, when used herein, will refer to the IHP and any lateral extensions around the cervix or most proximal aspect of the vagina.

Autonomic nerve fibers travel from the IHP around the cervix to the vesical plexus, which communicates with autonomic fibers to innervate the bladder. Some autonomic fibers travel from the IHP to the posterior-lateral aspect of the cervix to right and left Frankenhauser's plexuses FP (also known as Lee's or the uterovaginal plexuses). Frankenhauser's or Lee's plexuses send some nerves upward to innervate the uterus and some nerves inferiorly to innervate the vagina, cervix, urethra, and clitoris. Both of these plexuses may be important in controlling urinary tract function. Autonomic fibers travel between the IHP and the middle rectal plexus to innervate the distal rectum.

Surgical removal of the cervix can result in injury to the hypogastric nerves, IHP, Frankenhauser's plexuses and/or the vesical plexuses. These structures often heal and function well post-operatively. However, they can sustain permanent injury and exhibit chronically altered function resulting in chronic urinary tract conditions and other forms of pelvic organ dysfunction.

As mentioned above, autonomic nerves and somatic nerves have different functions. Autonomic nerves control visceral, internal organ function and some types of pain. The bladder and urethra are innervated by autonomic nerves.

Somatic nerves mediate voluntary muscle activity, body movement, and somatic sensation. The pudendal nerve PN and its distal branches mediate voluntary pelvic floor function and some distal vaginal, urethral, anal and genital sensation. The nerve types also have different distributions. For example, autonomic nerves traveling to and from the pelvic organs enter via a proximal and central approach, just above the top of the posterior vagina in the center of the pelvic cavity. The somatic nerves travel to the pelvic floor from an inferior and lateral approach. A problem with prior art devices placed in the vagina is that they stimulate, usually intentionally, somatic nerves adjacent the pelvic floor such as the pudendal nerve and its branches.

Autonomic nerves are responsible for signaling visceral organ or peritoneal pain, such as that caused by endometriosis, dysmenorrhea, interstitial cystitis, irritable bowel syndrome, adhesions and other conditions. Autonomic nerves also influence how visceral organs respond to somatic pain and can be a source of referred pain in a somatic distribution. Autonomic sensation may be transmitted by autonomic (or visceral) sensory fibers, not necessarily sympathetic or parasympathetic fibers.

In an embodiment, the present invention is an indwelling, removable, programmable, stimulation device that is positioned in the fornices of the vagina, thereby optimally targeting autonomic plexuses of the pelvic organs and the distal aspect of the hypogastric nerves. This device will deliver electrical stimulation (and support other therapies, such as application of a magnetic field, medication, or ultrasound) to the plexuses and associated nerves at the autonomic gateway between the pelvic organs and the central nervous system, mainly at the left and right hypogastric nerves, inferior hypogastric plexus, left and right Frankenhauser's plexuses, the vesical plexus and possibly the middle rectal plexuses. Stimulation of these plexuses and distal hypogastric nerves changes a signal sent by these plexuses and nerves to their associated efferent and afferent nerve fibers.

At this location the neuromodulation signal will have more effect than if it were distributed distal to the plexuses, such as with current devices that stimulate and reside lower in the vagina. With more distally stimulating devices some aberrant nerve signal arising above the stimulation site can travel, for example, between the urinary tract and the plexuses or hypogastric nerve above the stimulation site. The same limitations can hinder the effects of the current devices in treating gynecologic, colorectal and pain conditions as well. The device of the present invention, on the other hand, is positioned in the vaginal fornices or upper-most portion of the vagina thereby optimizing stimulation to the autonomic nerves and plexuses that control the sensation and function of the pelvic organs, including the bladder.

In a preferred embodiment, a ring-like device with an electrode, or a plurality of electrodes, will reside in the fornices, adjacent to the plexuses that surround the cervix. The device will also be able to target the junction between the left and right hypogastric nerves (that travel to and from the IHP along the uterosacral ligaments) and the IHP. An advantage of the present invention is that positioning the device in the fornices allows access to the collection of plexuses (vesical, inferior hypogastric plexus, and Frankenhauser's plexus) and the hypogastric nerves simultaneously with a single device.

The device may also have bilateral pairs of electrodes: right and left anterior, right and left anterior-lateral, right and left posterior-lateral, and right and left posterior leads. Any individual electrode or grouping of electrodes may be programmed to work with or independently of any other electrode or grouping of electrodes as described in further detail below. Bilaterality allows great flexibility of use. Each patient has an individual distribution of autonomic nerves and plexuses and some may have a dominant side. Alternating between right and left sides may also be important for any given patient to reduce habituation. Stimulation regimens may be customized for each patient.

The position of the device is essential to its unique ability to stimulate the target autonomic plexuses in the pelvis. For example, the posterior electrodes are adjacent to the IHP, the posterior-lateral electrodes are adjacent to left and right Frankenhauser's plexuses, the anterior electrodes are adjacent to the vesical plexus and the anterior-lateral electrodes are adjacent to the fibers approaching and leaving the vesical plexus. The anterior-lateral electrodes and posterior-lateral electrodes may ultimately reside adjacent to the vesical plexus or IHP respectively, depending on normal variant distribution of nerves and plexuses in an individual patient. As noted above, some IHP or hypogastric nerve fibers may travel along the undersurface of the cardinal ligament, just anterior to the USL. The posterior or posterior-lateral sets of electrodes may stimulate the autonomic fibers in the IHP or nerve fibers leaving or approaching the IHP that affect autonomic communication with the middle rectal plexus and/or autonomic rectal nerves. They may also affect signaling of the left and right hypogastric nerves as they approach and leave the IHP along the distal end of the uterosacral ligaments USL.

There will be multiple embodiments that optimize the direction of signal to the target structures and/or contact with the tissue. For example, in an embodiment the ring will have a flared and/or curved rim to increase electrode contact with the vaginal wall and adjacent nerves. Another embodiment may have protruding tabs extending from the ring to maintain position and/or more effectively direct current to the target nerves or plexuses. The device may also have a marker or positioning feature in order to maintain proper orientation relative to a midline. There may also be a feature available to optimize the transmission of electrical signal across the vaginal wall.

By directing signals to the peri-cervical plexuses and nerves, stimulation is directed to autonomic nerves while minimizing, and possibly eliminating, stimulation of somatic nerves and pelvic floor muscles. This is an essential distinction of the present invention from current devices. Because the device will reside in the fornices, or uppermost portion of the vaginal apex in some women, it will be well proximal to the somatic sensory nerve distribution. This will allow the patient to wear the device without awareness, making continuous treatment regimens possible. Such continuous regimens may be difficult with conventional devices residing lower in the vagina. Convenience of use, privacy, and comfort may increase compliance and, therefore, treatment success using the devices and methods of the present invention.

The device being described is able to work unilaterally, bilaterally, anteriorly, posteriorly and/or laterally as a single device that is easily placed and removed. With the device of the present invention the stimulation sites may also be changed or rotated. For example, a stimulation regimen may alternate between the rightward then leftward aspect of the IHP or vesical plexus, right and left Frankenhauser's plexus, or the junction or intersection between the right and left hypogastric nerves and the IHP. The feature allows increased flexibility with treatment regimens, giving certain plexuses or nerves rest while stimulating others.

The device of the present invention will also be able to target vastly more autonomic signals traveling to and from the pelvis. This may make it more effective at treating global pathologic problems, such as chronic pelvic pain. For example, a patient with severe pelvic pain may require continuous circumferential stimulation while a patient with overactive bladder may only need to target therapy to a single plexus.

As such, the device of the present invention permits the patient to receive individualized therapy. After initial placement, each patient's symptoms, response to treatment and any side effects may be monitored. A regimen will be customized based on her response to therapy. The device is programmable and the patient will be able to have adjustments to her regimen as desired. The plurality and laterality of electrodes allows a wide variety of stimulation opportunities.

For example, an overactive bladder patient may do well with the electrodes adjacent to the IHP stimulating 30 minutes daily. A patient with side effects to signaling of the IHP, say constipation, may prefer use of the anterior leads near the vesical plexus. If a patient has a blunted response after a long course of use, a good option could be to stimulate only the right anterior leads for a week and then rest the associated nerves while stimulating the leftward nerves of the vesical plexus during the following week. An interstitial cystitis/painful bladder syndrome patient may benefit from stimulating the vesical plexus and one or both of Frankenhauser's plexuses simultaneously to treat both bladder pain and urgency.

A patient with a spinal cord injury may do better with signaling the IHP continuously to control high levels of aberrant signal. This could afford treatment of fecal and urinary incontinence. Another patient may benefit from activating Frankenhauser's to treat non-obstructive urinary retention.

A woman suffering from dysmenorrhea (pain with menstruation) may only need the posterior-lateral leads active in order to stimulate Frankenhauser's plexuses and avoid dampening signal to and from the rectum or bladder. She could use the device five days a month. One patient with chronic pelvic pain may require continuous circumferential stimulation. Another may only require therapy targeted to the plexuses on one side allowing the rectal and bladder signals to function normally on the contralateral side. One therapeutic goal will be to find the least amount of signal required to treat each patient.

Specific aspects of the present invention are now described. The device has a nerve stimulating element positioned on an exterior surface of a body for contact with the exposed or internal surface of the vagina. The nerve stimulating element may stimulate nerves in any suitable manner including provision of one or more emitting elements, which emit electrical energy, ultrasound energy, a drug, a magnetic field or other suitable stimulus. In a specific embodiment, the nerve stimulating element may be one or more electrodes, which deliver electrical energy to stimulate adjacent plexuses, nerves and associated autonomic nerve fibers.

As mentioned above, many conventional devices contribute to side effects from stimulating somatic nerves adjacent to the distal or lower half of the vagina. These devices also often describe intentionally stimulating pelvic muscles and somatic nerves. The present invention avoids drawbacks associated with these devices by providing a device which has all of the nerve stimulating elements positioned in the proximal half of the vagina and may have the entire device positioned in the proximal half of the vagina. To this end, the present invention provides nerve stimulating elements that are positioned close to the target plexuses. These nerves travel close to the proximal end of the vagina and have branches, which are typically no more than 2 cm from the exposed surface of the vagina and, as such, the preferred embodiments are described with the nerve stimulating element being no more than 3 cm from the target nerve plexus or nerve. Stated another way, the nerve stimulating element may be positioned no more than 3 cm from the uterosacral ligaments which are positioned adjacent the target plexuses. Stated still another way, the nerve stimulating element is positioned to stimulate the vesical plexus, left and right Frankenhauser's plexus, left and right hypogastric nerves, and/or inferior hypogastric plexus without intervening nerves, and in particular without intervening somatic nerves. Stated still another way, the nerve stimulating element may be positioned to contact the exposed surface of the vagina closer to the left or right hypogastric nerve, vesical plexus, Frankenhauser's plexuses, or the inferior hypogastric plexus, than to the pelvic floor. Stated yet another way, the nerve stimulating element (and in some embodiments all nerve stimulating elements) is positioned within 3 cm from a proximal end of the vagina, proximal to a distal end of the cervix, or proximal to the midpoint between the proximal and distal ends of the vagina. Finally, the entire device may be positioned proximal to a midpoint between the proximal and distal ends of the vagina or within 5 cm from the proximal end of the vagina.

The device may also include a plurality of nerve stimulating elements to stimulate the left and right sides of the target nerve plexuses and/or nerves either simultaneously or independently. Providing independent nerve stimulating elements on the left and right sides of the target plexuses and nerves permits tailoring the therapy for the user and condition being treated. Furthermore, the laterality of treatment regions may be changed periodically to reduce habituation thereby permitting stimulation of the same plexus from different approaches.

The main body of the device may form a closed loop having a central opening with the cervix positioned in the central opening. Although the main body extends completely around the cervix, the main body may extend only partially around the cervix. To this end, the main body may extend around at least 120 degrees, or even 270 degrees, around the cervix relative to the cervical axis. For example, the main body may be C-shaped or U-shaped. In another aspect of the present invention, the nerve stimulating elements (such as the electrodes) are spaced apart at least 120 degrees, or even 180 degrees, relative to the cervical axis (or the central axis when the cervix is absent) so that the target nerve plexuses may be stimulated independently (or simultaneously) as described herein with a single device on opposite sides of the cervix. Of course, the nerve stimulating element(s) may be positioned only along a posterior or anterior half of the vaginal canal for targeted use as described herein rather than spaced around the periphery of the device.

The present invention may be useful in stimulating and altering autonomic nerve function for treatment of urinary urgency, frequency, incontinence, incomplete bladder emptying, pain and other pelvic visceral organ dysfunction, such as fecal incontinence. The devices and methods are designed to deliver therapy, an example being electrical stimulation, to specific plexuses that mediate autonomic communication between the visceral pelvic organs and the central nervous system. The device will also alter the signal from visceral pain nerves.

The indications for use include those referred to below. In addition, alteration of autonomic nerve signal may be used to treat cardiovascular conditions, such as hypertension, bradycardia, tachycardia and other dysrhythmias. Beneficial effects of this treatment may include altering autonomic tone, thereby treating chronic stress related conditions, such as gastritis, inflammatory conditions (such as asthma, inflammatory bowel diseases, atherosclerosis and arthritis), headaches, diabetes and anxiety.

The present invention is also directed to modulating the peripheral autonomic nervous system to alter, and ultimately reduce, systemic sympathetic tone. The autonomic nervous system functions as a circuit. Modulation of the signal of the autonomic plexuses surrounding the cervix and uppermost aspect of the vagina, namely the inferior hypogastric plexus (IHP), Frankenhauser's plexuses (L and R) and the vesical plexuses (L and R), may alter systemic sympathetic discharge throughout the sympathetic chain. Stimulation of the superior hypogastric plexus (SHP) may have a similar effect and may be included in this group of plexuses. Stimulation of these plexuses may influence the sympathetic tone of individual organs differentially. Alternatively, this therapy may influence the sympathetic tone of some, but not all organs under the control of the autonomic nervous system. In one aspect of the present invention, at least three of the plexuses are stimulated in accordance with methods and systems of the present invention.

The current invention will decrease sympathetic tone thereby protecting organs (such as the heart and vascular system) from deleterious effects of chronically increased sympathetic stimulation (via hormones, neurotransmitters, chemicals) and/or mitigate systemic disease processes influenced by sympathetic outflow, such as inflammation and immunosuppression.

In one aspect of the present invention, a battery-operated nerve stimulating device (which includes a handheld programmable and wireless controller) is designed to be positioned in the vagina and specifically the vaginal fornices. An embodiment may also include a version wherein the device and controller are connected via a cable without departing from the scope of the invention. The controller may record information regarding previous stimulation regimens, impedance, patient responses to therapy and other information. The information stored by the controller can be transferred to a computer or other device to review and analyze. The controller may also recommend stimulation regimens, based on patient response to past treatments or standard regimens known to be therapeutic.

The devices and methods distribute therapy to autonomic plexus targets in the central pelvis while avoiding somatic nerves, general paravaginal nerves and the pelvic floor muscles. Unlike other vaginal neuromodulation devices, the electrodes are positioned in the most cephalad aspect of the device to optimize distribution of therapy above the vault of the vagina. Multiple embodiments are designed to assure adequate coverage of the plexuses. For example, versions include a torus-like, a truncated pyramidal frustum and truncated cone. Variations will include devices with and without a central opening, as the later may be beneficial for women without a cervix.

The devices of the present invention may be shaped to cause the apical vagina to widen and elevate, thereby bringing the vaginal wall closer to the target plexuses. The shape of the device also induces tenting of the vagina around the surface of the device. This layering of the vagina over the nerve stimulating elements optimizes contact between these elements and the vaginal wall. These embodiments cause a modest increase in vaginal wall tension and decreased resistance within the vaginal wall, thereby providing a more predictable interface between the nerve stimulating elements (such as electrodes) and the target structures.

The nerve stimulating elements generally conform to the contour of the device to maintain consistent proximity and contact with the vaginal wall. This feature may assure treatment of the entire plexus and plexus associated nerves that travel peripheral to the cervix and/or apex of the vagina. This also facilitates stimulation of pain nerves, both visceral and autonomic, traveling to and from adjacent visceral organs, within the preperitoneal tissue or associated with the peritoneum.

The invention may also provide surface features designed to optimize stimulation of the targets. In one embodiment, the device surface may have an undulating exterior surface with peaks, or raised areas, between valleys or recesses. The raised areas protrude into the vaginal wall to create a seal between recesses. Each recess will contain at least one nerve stimulating element and may also include a conductive material.

An embodiment will provide variations of a form-fitting, externally applied and absorbable ring-like insert. The insert includes a plurality of electrically conductive areas coupled to a substrate with the plurality of electrically conductive areas being separated by non-conductive areas. The substrate may form a closed loop with the electrically conductive areas positioned at spaced apart locations on the closed loop. The substrate may dissolve within the body to leave the conductive areas positioned within recesses in the main body of the device. The conductive areas may include a gel, such as a hydrogel, or a porous material having a flowable conductive material contained in the pores (such as a hydrogel or saline). The porous material may be a resilient foam element or any other suitable biocompatible porous element. The substrate may also include an elastic band that secures the insert to the device.

Once the insert is applied to the device the conductive areas will reside within the recesses and the exposed substrate will cover the external surface of the device ultimately providing a smooth outer contour.

The device may also include a reservoir (or reservoirs) of a conductive, flowable material (such as a hydrogel or saline). The reservoir is coupled to the main body of the device and is further fluidly coupled to one or more recesses. The conductive, flowable material may be automatically drawn into the recess. For example, the recess may include a porous element that draws the flowable material automatically out of the reservoir and into the recess. Alternatively, mechanical, chemical, thermal, electrical or hydrogen driven means may be used to force the flowable material out of the reservoir.

The physical characteristics of the devices described herein may also help maintain proper orientation. As mentioned previously, the device may include recesses, which form peaks and valleys that help the device maintain the same position and limit rotation. The truncated pyramid and truncated cone shapes may help to drape the vagina in a similar fashion over the device. The torus shaped embodiment is designed to prevent dislocation, by virtue of the smooth outer circumference. The design will facilitate the vagina to conform to the shape and envelope the device so that when pressure is exerted on the upper vagina the vagina and device move as a unit. The device may also be able to alert the user when the battery is weak. The device may communicate with the handheld controller and a flashing light and/or audible alarm will notify the user. The device may also mechanically pulse and/or send stimulation so that the patient is alerted.

To comprehensively treat the peripheral pelvic visceral plexuses the system of the present invention may include a vaginal positioned device with multiple nerve stimulating elements that may operate independently to create multiple potential circuits with the implant. The vaginal device allows delivery of therapy through different plexuses via multiple current pathways, as 2 or more groupings of electrodes (one vaginal device and one or more implants) triangulate therapy and provide selective stimulation of target plexuses and associated nerves. Thus, the system being disclosed offers open circuit stimulation (for a single electrode) and closed circuit and selective stimulation, which may be directed by the user or health care provider.

The advantage of selective stimulation is the opportunity to employ multiple treatment pathways and potential regimens so that therapy may be individualized. For example, a user with pelvic pain may benefit from modulating nerve signals via Frankenhauser's plexus. She or her healthcare provider may activate the circuit between the vaginal electrodes in the posterior aspect of the vaginal device (near Frankenhauser's plexus) and one or more of the implants, depending on whether she desires unilateral or bilateral treatment. A patient with significant urinary urgency may benefit from creating a circuit between the vesical plexus by activating the stimulating elements on the anterior aspect of the vaginal device and the implant. A patient with fecal incontinence or fecal urgency may favor simply stimulating the IHP via the uterosacral implants with or without input from the vaginal device. The vaginal device allows increased flexibility of use, such that therapy may be tailored to each woman's symptoms and response to therapy.

Another advantage of the vaginal component and its ability to select and control the delivery of energy through different tissue and nerve pathways is minimization and possibly prevention of habituation. The vaginal component stimulating elements afford right/left and anterior/posterior electrodes as discussed herein. Targeting specific structures also avoids unnecessary stimulation of unintended targets. This feature will minimize side effects. Stimulating as few visceral and autonomic pelvic nerves as necessary may decrease habituation associated with pelvic plexuses, interneuron and the central nervous system stimulation. Focused therapy will require less current and ultimately less energy use, which favors prolonged battery-life.

The vaginal device and/or controller records data regarding treatment regimens, including start and end time, nerve stimulating elements used, resistance, current, frequency, disruption of therapy and any changes made to a regimen. In real time the user will be able to record subjective and objective information, which will be used to adjust and tailor future regimens to her specific needs. For example, if she has a good response to a certain regimen she may note it at the end of a day or predetermined assessment period. In this case, the regimen will be maintained or she may opt to decrease stimulation intensity towards the threshold of benefit. She may also note when she experiences a side effect. She may also record information about her menstrual cycle and be reminded of ovulation, and her last menstrual period, such that therapy is avoided in the luteal phase, if desired.

By reviewing the treatment regimen (including current, frequency of stimulation, active electrodes and duration of therapy) employed during the time the side effect was experienced, she and her healthcare team will be able to change the stimulation setting or redirect therapy to another target structure altogether. The user may record experiences via free text, respond to periodic questions or via standardized questionnaires and bladder diaries available in the software. All data will be recorded and downloadable to computers and portable devices, such as phones. The user's personal device (such as a phone) may reprogram the controller and alter the regimen. If the patient desires and consents, this objective, subjective and regimen data may be transmitted electronically for remote assessment by healthcare providers or for research purposes.

The controller of the vaginally positioned device may also communicate instructions to the device such as selecting a stimulation regimen, including which electrodes are active, the amount of current, pulse characteristics, and duration of therapy. The control system of the vaginal device will also maintain information about the stimulation regimens employed, resistance, current, power usage and other information related to the stimulation. The hand held controller may also record subjective and objective input from the user.

In another aspect of the present invention, the present invention seeks to modulate the peripheral autonomic nervous system to alter, and ultimately reduce, systemic sympathetic tone. The autonomic nervous system functions as a circuit. Modulation of the signal of the autonomic plexuses surrounding the cervix and uppermost aspect of the vagina, namely the inferior hypogastric plexus (IHP), superior hypogastric plexus (SHP), Frankenhauser's plexuses (L and R) and the vesical plexuses (L and R), may alter systemic sympathetic discharge throughout the sympathetic chain. Stimulation of these plexuses may influence the sympathetic tone of individual organs differentially. Alternatively, this therapy may influence the sympathetic tone of some, but not all organs under the control of the autonomic nervous system. In one aspect of the present invention, at least three of these plexuses are stimulated in accordance with methods and systems of the present invention.

The current invention will decrease sympathetic tone, thereby protecting organs (such as the heart and vascular system) from deleterious effects of chronically increased sympathetic stimulation (via hormones, neurotransmitters, chemicals) and/or mitigate systemic disease processes influenced by sympathetic outflow, such as inflammation and immunosuppression.

In another aspect of the present invention, an implant with a nerve stimulating element is implanted and preferably secured to a uterosacral ligaments. The implant, like the vaginal devices, modulates the action of nerves and treats conditions by altering the signals of autonomic nerve plexuses, their associated nerves and nerve endings and potentially interneurons and central nervous systems nerves and processes via one or more nerve stimulating implants. The implant may be used independently, together with other implants, or in combination with the vaginally positioned devices of the present invention. The vaginal device may also stimulate the anatomic structures described either by creating a circuit with the implanted electrodes or independently. In another aspect of the present invention, at least two implants are secured to the same uterosacral ligament.

The vaginal device may include the controller and power source to deliver therapy to the inferior hypogastric plexus (or pelvic plexus), left and right Frankenhauser's plexus (or Lee's plexus), vesicle plexuses (L and R) and even the superior hypogastric plexus. These plexuses may, of course, be called by other names such as Lee's plexus as another name for Frankenhauser's plexus without departing from the invention. Furthermore, the Frankenhauser's plexus refers to both left and right Frankenhauser's plexuses collectively. Unless otherwise specified, use of Frankenhauser's plexus or plexuses shall mean both plexuses.

The present invention treats urologic, gynecologic, sexual, colorectal, and pain conditions in women with neuromodulation via electrical stimulation (and other modalities), (including heat, ultrasound, and medication). The implant and indwelling vaginal device deliver therapy to specific autonomic plexuses that communicate with nerves traveling to and from genitourinary and pelvic structures. The neuromodulation of the present invention stimulates the nerve plexuses to alter signal transmitted by the nerve plexuses and associated autonomic nerves between the pelvic organs and the central nervous system.

For reference (FIG. 1) autonomic nerve signals traveling to and from the bladder, urethra, rectum, vagina, uterus, peritoneum and other pelvic structures travel through the inferior hypogastric plexus IHP, carrying the signal between pelvic structures and the spinal cord. The inferior hypogastric plexus IHP is the gateway between the visceral (bladder, gynecologic, rectum) organs and the central nervous system. The IHP is a coalescence of both sympathetic and parasympathetic autonomic fibers. The sympathetic fibers run between the thoracic nerve roots (T10-L2) and into the superior hypogastric plexus, then travel towards the IHP via the left and right hypogastric nerves LHN, RHN along the uterosacral ligaments USL. In some cases a portion of the sympathetic fibers may enter the IHP along the undersurface of the cardinal ligaments. These fibers facilitate bladder storage. The parasympathetic nerves travel from the sacral spinal nerve roots (S2-4) in the sacral or pelvic splanchnic nerves, or nervi erigentes towards the pelvic organs, often in association with the pelvic nerve. They facilitate bladder emptying. Sympathetic and parasympathetic fibers coalesce in the IHP over the posterior and lateral surfaces of the upper cervix, just above the vaginal insertion.

Importantly, the vagina terminates at the level of the pericervical ring (known by other names) around the uppermost portion of the cervix, just below the uterosacral ligament USL insertions. The recesses of the most proximal, or uppermost, aspect of the vagina that surround the cervix are called the vaginal fornices VF. The pelvic floor PF surrounds the lower portion of the vagina near the vaginal opening, making the "floor" of the pelvic cavity. The inferior hypogastric plexus IHP is a web-like plexus adjacent to the posterior and lateral cervix at the level of the uterocervical junction and the uterosacral ligament USL insertions, just proximal to the posterior vaginal fornix. Inferior hypogastric plexus IHP fibers also cover the distal uterosacral ligaments and possibly reside in the lower or under-portion of the cardinal ligament just anterior to the USL. For reference, the IHP is generally referred to as a singular structure in the literature, but anatomic studies suggest significant concentrations of these ganglia may be distributed bilaterally, as described above. For purposes of this description and application the IHP, when used herein, will refer to the IHP and any lateral extensions around the cervix or most proximal aspect of the vagina.

Autonomic nerve fibers travel from the IHP around the cervix to the vesical plexus, which communicates with autonomic fibers to innervate the bladder. Some autonomic fibers travel from the IHP to the posterior-lateral aspect of the cervix to right and left Frankenhauser's plexuses FP (also known as Lee's or the uterovaginal plexuses). Frankenhauser's or Lee's plexuses send some nerves upward to innervate the uterus and some nerves inferiorly to innervate the vagina, cervix, urethra, and clitoris. Both of these plexuses may be important in controlling urinary tract function. Autonomic fibers travel between the IHP and the middle rectal plexus to innervate the distal rectum.

In one embodiment of the present invention, the implant has a nerve stimulating element, such as an electrode, which is positioned around and/or through one or both uterosacral ligaments, adjacent to the inferior hypogastric plexus, Frankenhauser's plexus or the superior hypogastric plexus. The implant may also be secured to other structures, such as pubocervical fascia or the external vaginal wall, without departing from the scope of the invention. The therapy is designed to also treat the autonomic nerves traveling around the pericervical and apical vaginal fascia/connective tissue to visceral pelvic organs and the vesicle plexuses.

In one embodiment, the implant is generally cylindrical in shape with tapered ends. The implant may include a throughhole to accommodate the uterosacral ligament. The nerve stimulating element may be between 0.5 and 5.0 cm long and up to 2 cm wide. The outer surface of each implant is made of a biocompatible and insulating material to which the nerve stimulating elements are attached. The implant has a power source, such as a battery, which powers the implant. The battery may be rechargable and recharged remotely through tissue as is known in the art. For example, the charger may be positioned in the vagina and, in particular, positioned within the vaginal fornices VF.

The size and shape of the device is designed to provide an optimal surface area for stimulation of an autonomic plexus and associated nerves. The nerve stimulating element may be a relatively small microstimulator when treating a somatic nerve or nerve junction, such as a dorsal nerve ganglion. Autonomic nerves plexuses, on the other hand, are broader, so the nerves coalesce more diffusely thereby possibly necessitating a larger nerve stimulator. Broader distribution of therapy may be important for treatment success.

In another aspect of the present invention, the nerve stimulating element pierces the ligament. The uterosacral ligaments contain autonomic nerves as they travel to and from plexuses from the visceral pelvic organs. The implant may have two or more nerve stimulating elements (such as electrodes) in contact with the uterosacral ligament and positioned in series along the ligament. When an implant is secured to each uterosacral ligament, the implants may send current between the bilateral uterosacral ligament implants, thereby increasing the amount of therapy provided to the IHP and broadening the distribution of therapy.

The control system of the vaginally positioned device may communicate with the control system of implant(s) to coordinate stimulation (such as simultaneous or independent stimulation). The control systems may communicate with one another using the nerve stimulating elements to transmit and receive electrical impulses through tissue. Alternatively, the control system may generate radiofrequency signals, which are received by the control system of the implant.

The controller of the vaginally positioned device may also be used to control and send stimulation instructions to the implant either directly or indirectly via the vaginal device. The controller is configured to communicate control information (such as duration and intensity of stimulation) to the control system of the vaginal device. The controller may transmit a stimulation instruction to the device, which then transmits the stimulation instruction to the implant.

The devices, systems and methods of the present invention stimulate target nerves and plexuses while avoiding adversely influencing non-target somatic nerves, such as the pudendal nerve or its branches, adjacent to the distal or lower half of the vagina. Reducing side effects and possible urinary tract symptoms due to stimulating somatic nerves are thereby avoided in accordance with the present invention.

In addition to other treatments describe herein, the present invention may be used to treat any one or more of the following conditions: urinary urgency, frequency, nocturia, urge incontinence, stress incontinence of urine, loss of urine without sensory awareness, overflow incontinence, bladder pain, urethral pain, urethral syndrome, urethral stricture, urinary hesitancy, protracted urinary stream, pelvic floor dyssynergia, interstitial cystitis, dysuria, overactive bladder, incomplete bladder emptying, urinary retention, hesitancy, dysmenorrhea, pelvic pain, pelvic venous congestion syndrome, endometriosis, irritable bowel syndrome, constipation, fecal urgency, fecal incontinence, rectal pain, pain with defecation, anal pain. Of course, numerous aspects of the present invention may be practiced for a different condition without departing from the scope of the invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 14A is a cross-sectional view of the main body.

FIG. 14B is another cross-sectional view of the main body with an alternative electrode.

FIG. 15A is a perspective view of one end of the main body.

FIG. 15B is a perspective view of the same end of the main body as FIG. 15A with the alternative electrode of FIG. 14B.

FIG. 18 shows an end of the hub that abuts against the battery.

FIG. 19 shows another end of the hub that is coupled to the control system.

DETAILED DESCRIPTION

Figure 1:
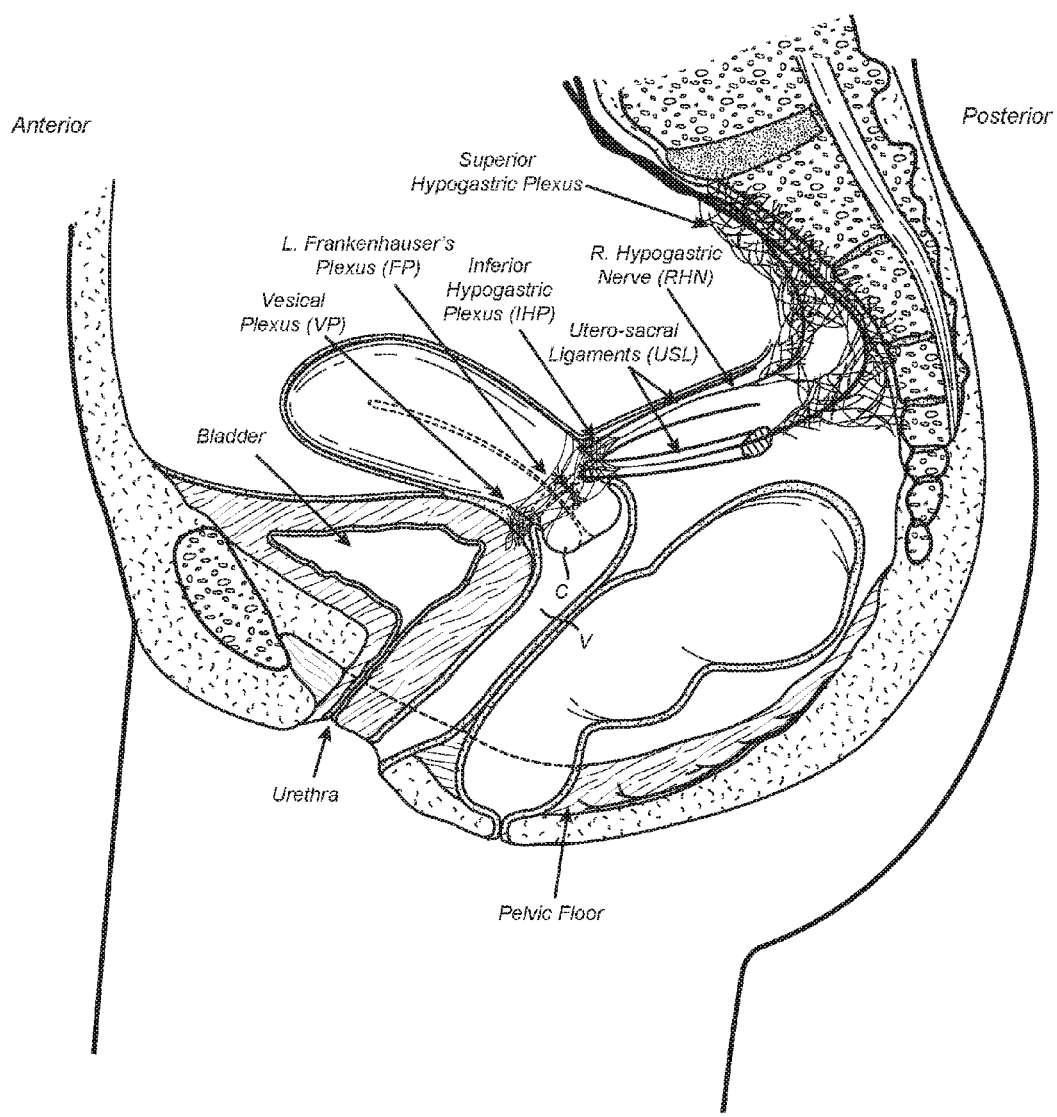
FIG. 1 is a parasagital view into the female pelvis from the left.
Figure 2:
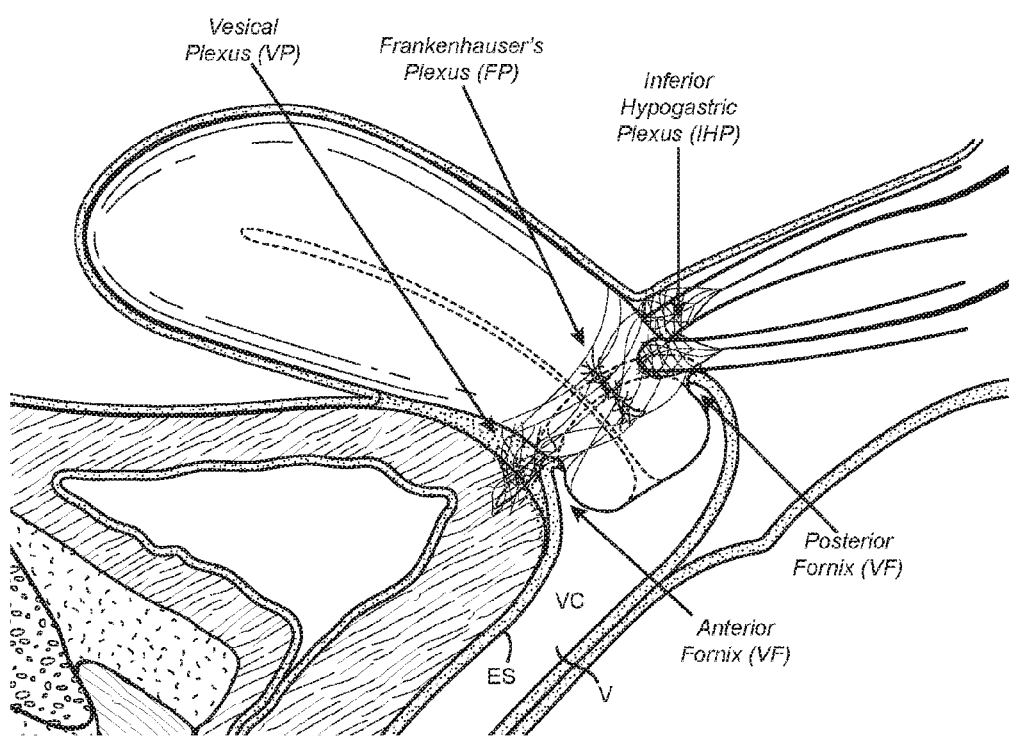
FIG. 2 is an enlarged view of the upper vagina and uterus.
Figure 3:
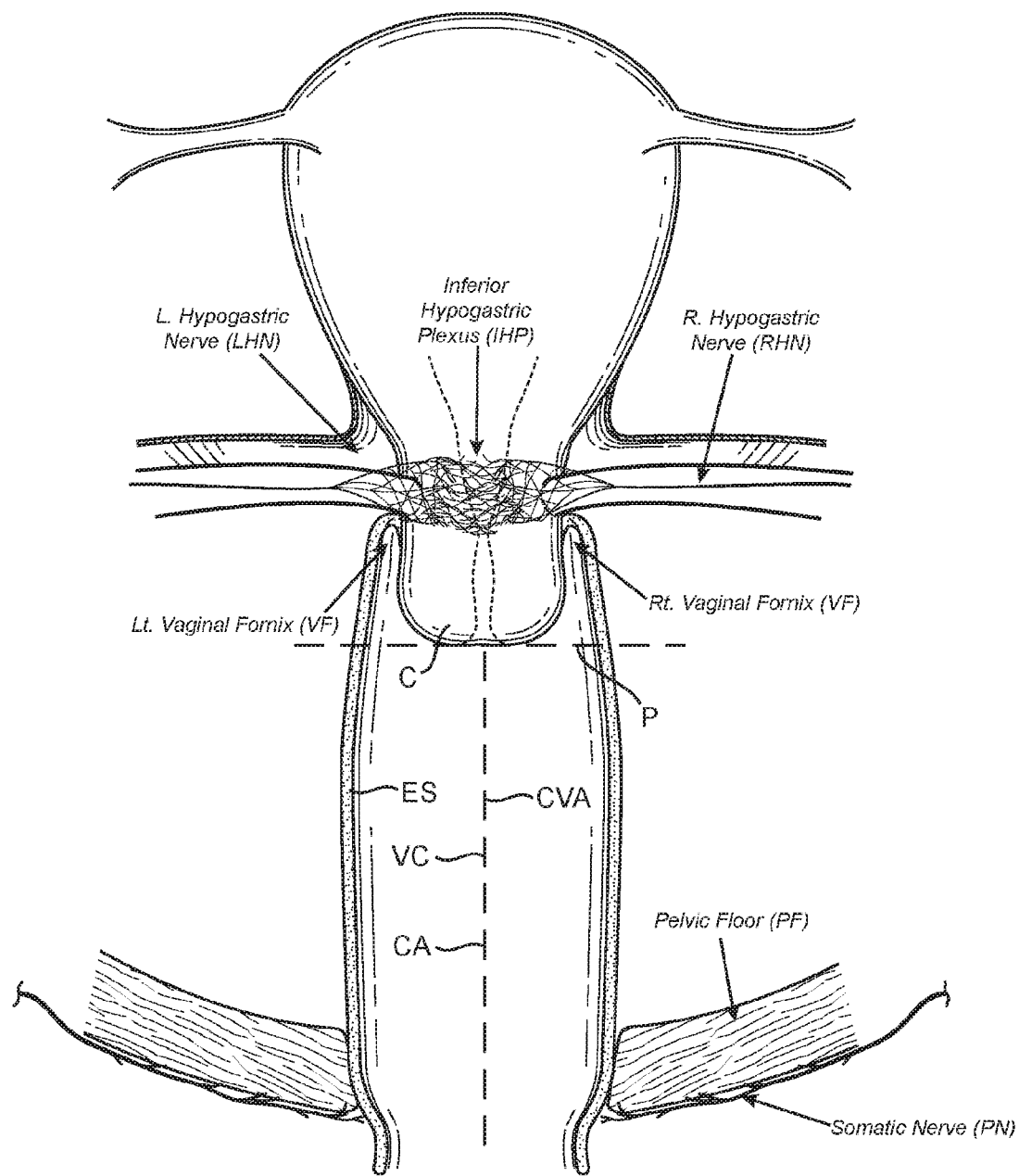
FIG. 3 is a posterior view of the gynecologic organs.
Figure 4:
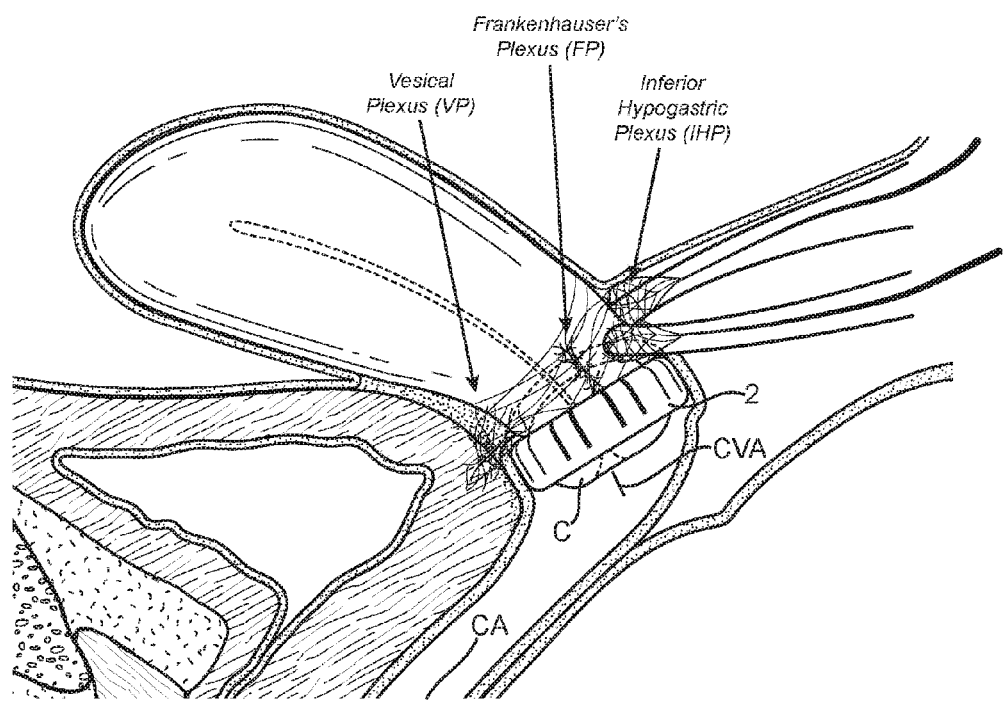
FIG. 4 is an enlarged view of the upper vagina and uterus with the device of the present invention positioned in the vaginal fornices.
Figure 5:
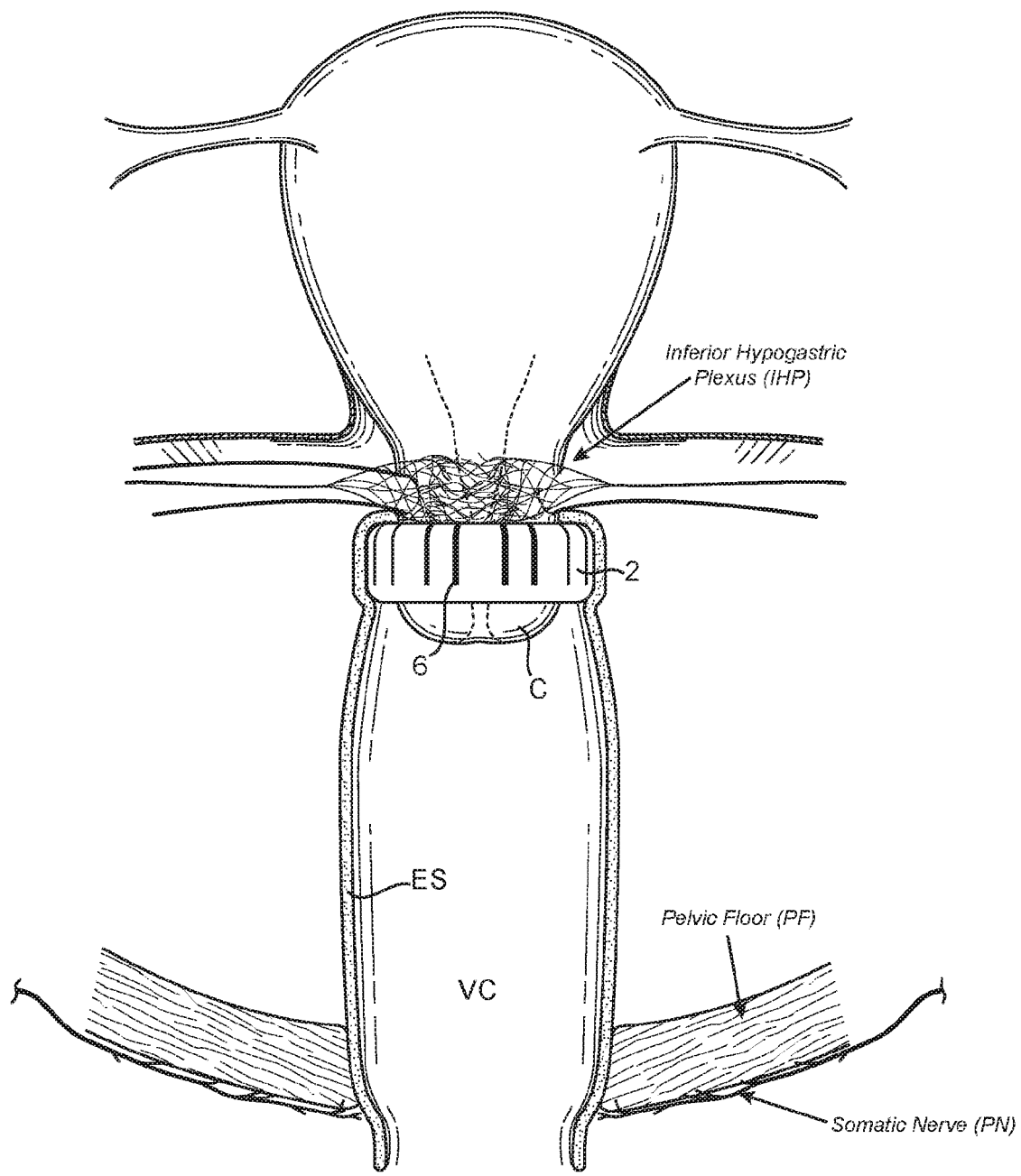
FIG. 5 is a posterior view of the gynecologic organs with the device positioned in the vaginal fornices.
Figure 6:
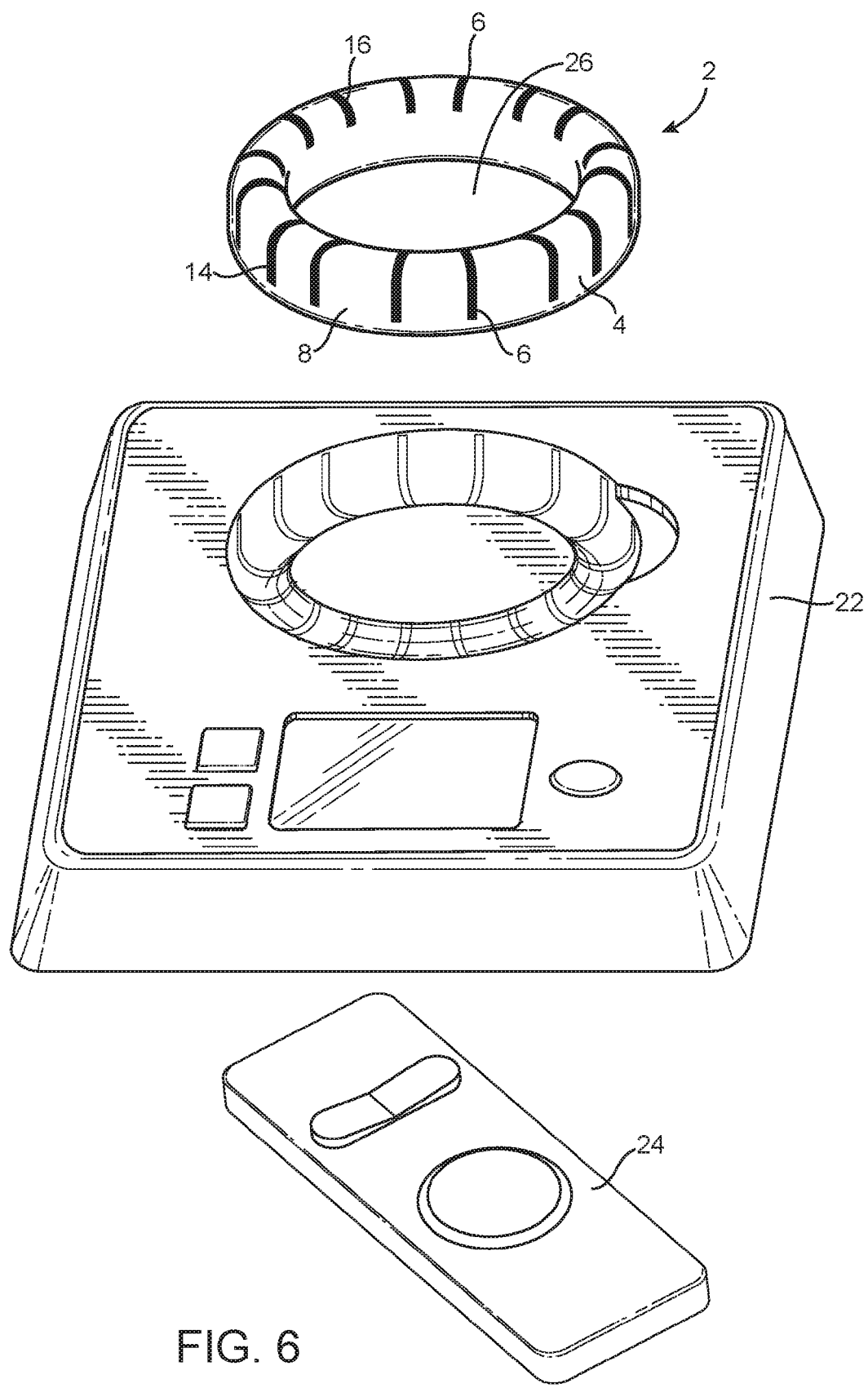
FIG. 6 shows the device, a charger and a controller.
Figure 7:
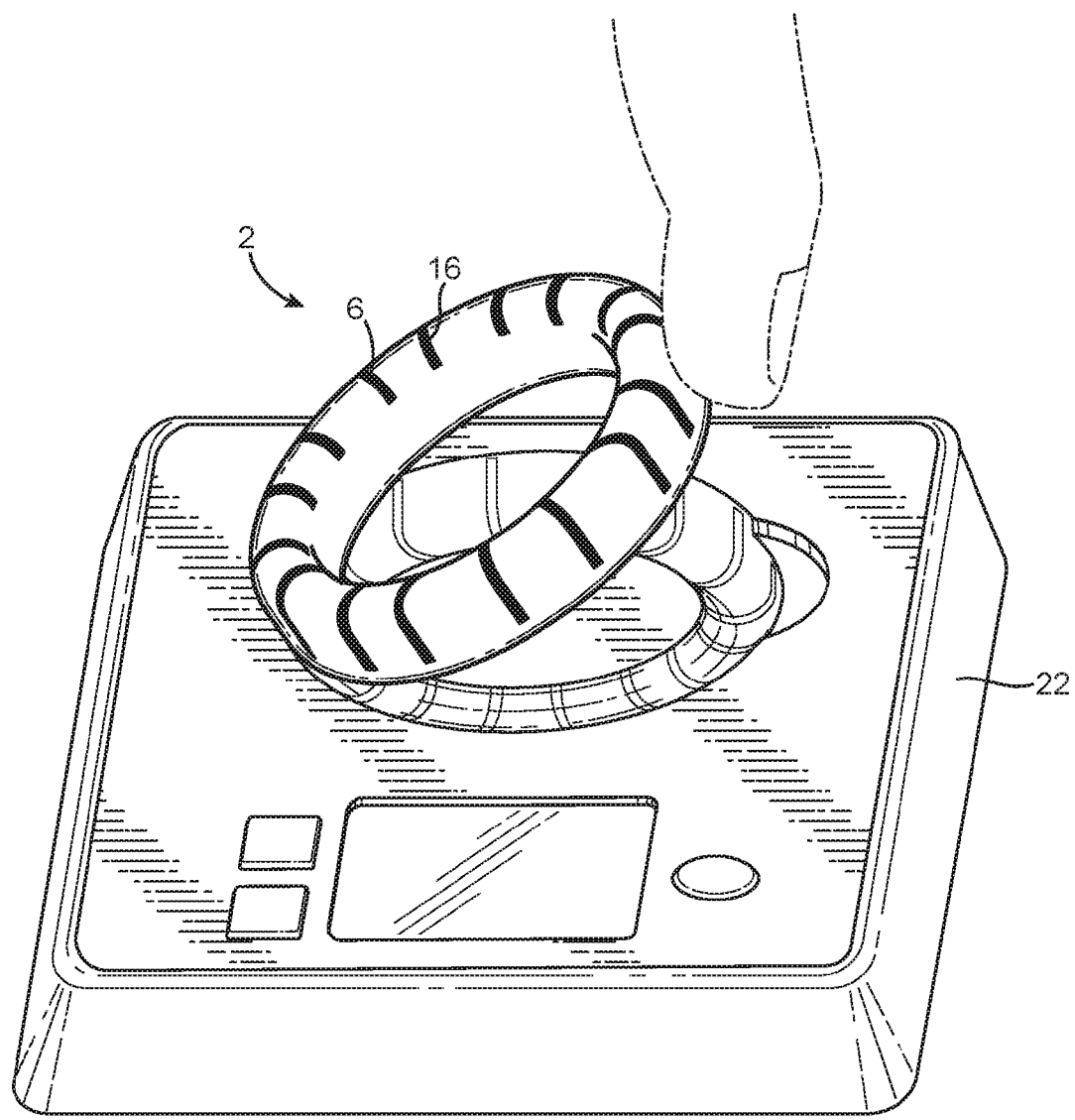
FIG. 7 shows removal of the device from the charger.

For the purpose of defining the invention, various terms are now defined for use herein with reference to FIGS. 1-3. Firstly, the vagina V is a fibroelastic, muscular structure that forms a canal (hereinafter "vaginal canal" VC) having a distensible, flexible lining. The surface of this flexible lining has an internal or exposed surface ES. The vagina, and vaginal canal, as defined herein has a proximal end terminating at the proximal aspect of the cervix and a distal end at the introitus where it joins the vulva. If the cervix C has been removed or is congenitally absent, the proximal end of the vagina (and vaginal canal) is simply defined by the uppermost portion of the vagina, also known as the vaginal cuff.

As used herein, the shape of the vaginal canal VC defines a central axis CA. A cervical axis CVA extends through and is aligned with the cervical canal CC. The cervical axis CVA is also an axis of symmetry, as closely as can be approximated with the anatomy, for the cervix extending through the cervical opening or cervical canal. A midpoint between the proximal and distal ends of the vagina (or the vaginal canal) is determined herein using the midpoint of the central axis. The central axis CA may, of course, have a relatively complex shape so long as the central axis CA generally defines and follows the orientation and shape of the vaginal canal VC. The proximal end of the vagina (and vaginal canal) is defined by the uppermost portion of the vagina. For example, a proximal portion of the vagina or vaginal canal extending 3 cm from the proximal end of the vagina includes the vagina extending 3 cm from the uppermost (proximal) end.

The vaginal fornices VF, as used herein, refers to a space or recess between the cervix and the adjacent vaginal wall. Specifically, the space is positioned between the exposed surface ES of the vaginal canal VC and an exposed surface of the cervix C and further bounded by a plane P extending perpendicular to the cervical axis CVA and passing through distal end of the cervix C. The vaginal fornices VF may be thought of as a somewhat torus-shaped space but, of course, varies from patient to patient.

Referring now to FIGS. 4-8, a device 2 in accordance with the present invention is shown. The device 2 includes a main body 4 having a plurality of nerve stimulating elements 6 positioned on an exterior surface 8 of the main body 4 for contact with the exposed or internal surface ES of the vaginal wall 12. The nerve stimulating elements 6 may stimulate nerves in a number of different ways without departing from numerous aspects of the invention. For example, the nerve stimulating element 6 may include one or more emitting elements 14 which emit electrical energy, ultrasound energy, a drug, a magnetic field or other suitable stimulus to the target nerves.

In a specific embodiment, the nerve stimulating elements 6 may be one or more electrodes 16 that deliver electrical energy to stimulate adjacent nerves as described below. As used herein, it is understood that use of "electrode" or "emitting element" herein shall be interchangeable with the term nerve stimulating element, and vice versa, as applicable. Thus, aspects of the invention described or claimed specifically in relation to the electrodes 16 or nerve stimulating element 6 are equally applicable to the other and such substitution is expressly incorporated here. Furthermore, the application of electrical stimulus is sufficient to change the signals transmitted by the target nerves and plexuses described below. In this manner, neuromodulation of the target nerves is achieved.

The electrodes 16 are coupled to a control system 18 which in turn is coupled to a power source 19 such as a battery 20. The device 2 may include a battery charger 22 or may be charged transcutaneously as is known in the art. Of course, an advantage of the present invention is that the device 2 may easily be removed, charged and repositioned which cannot be accomplished with conventional surgically placed devices. The device 2 may also include an external controller 24 which may operate the device remotely when the device 2 is in place. The battery charger 22 may also be a controller for programming the device 2 in accordance with methods described herein. A few prior art devices which describe suitable control systems, controllers and battery charging systems are described in U.S. Pat. Nos. 7,729,772, 7,813,809 and 8,165,692 which are hereby incorporated by reference. The controller 24 (and charger 22) may control the duration, frequency, intensity and stimulation protocol as described herein and in the patents incorporated above. The controller 24 may also be incorporated or applied to another suitable personal electronic device, such as a cellphone, programmable watch, tablet, laptop, electronic calendar/organizer or any other suitable personal programmable electronic device, without departing from the scope of the invention. If the controller 24 is incorporated into a personal electronic device the necessary control software can be downloaded as a conventional application. The controller 24 may take advantage of the ability of the personal electronic device to communicate wirelessly with the device 2 (and other devices described below).

Figure 21:
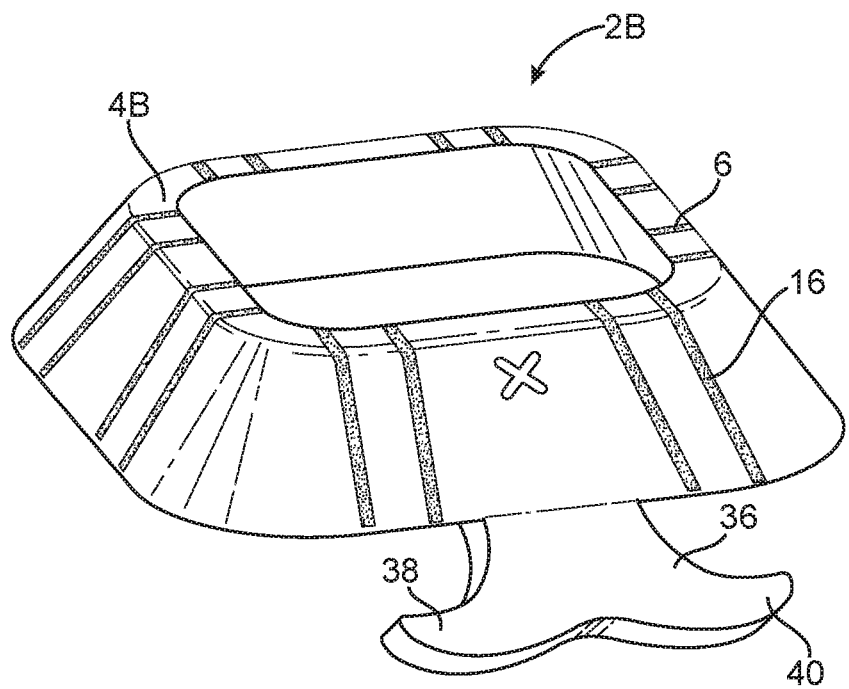
FIG. 21 shows still another device in accordance with the present invention.

The main body 4 of the device 2 forms a closed loop having a central opening 26 with the cervix C positioned in the central opening 26. The main body 4 may be substantially circular or may have substantially straight sides 28 as shown in FIG. 21. Of course, the main body 4 may take any other shape such as oval, elliptical, square, or even hexagonal. Although the main body 4 extends completely around the cervix, the main body 4 may extend only partially around the cervix. To this end, the main body 4 may extend around at least 180 degrees, or at least 270 degrees, around the cervix relative to a cervical axis 30 (which is the same as the central axis CA of the device) and may be, for example, C-shaped, V-shaped or U-shaped. As used herein, the central opening 26 does not need to be completely surrounded by the main body 4 so long as the main body 4 extends partially around the cervix and opening 26 as described herein. Thus, a substantially C-shaped or U-shaped main body still will include a central opening 26 with each central opening 26 defining a central axis of the main body 4 CAB. The nerve stimulating elements 6 (such as the electrodes 16) are also spaced apart at least 120 degrees, or even 180 degrees, relative to the cervical axis CVA (or the central axis of the main body CAB described further below when the cervix is absent) so that the various nerve plexuses may be stimulated as described herein. Of course, the nerve stimulating element(s) 6 may be positioned only along a posterior or anterior half of the vaginal canal for targeted use as described herein without departing from numerous aspects of invention.

The device 2 of the present invention may be positioned partially or entirely within the vaginal fornices VF. The nerve stimulating element 6 (and in some embodiments all of the nerve stimulating elements 6) contacts the exposed surface of the vagina 10 proximal to the distal end 46 of the cervix.

Figure 8:
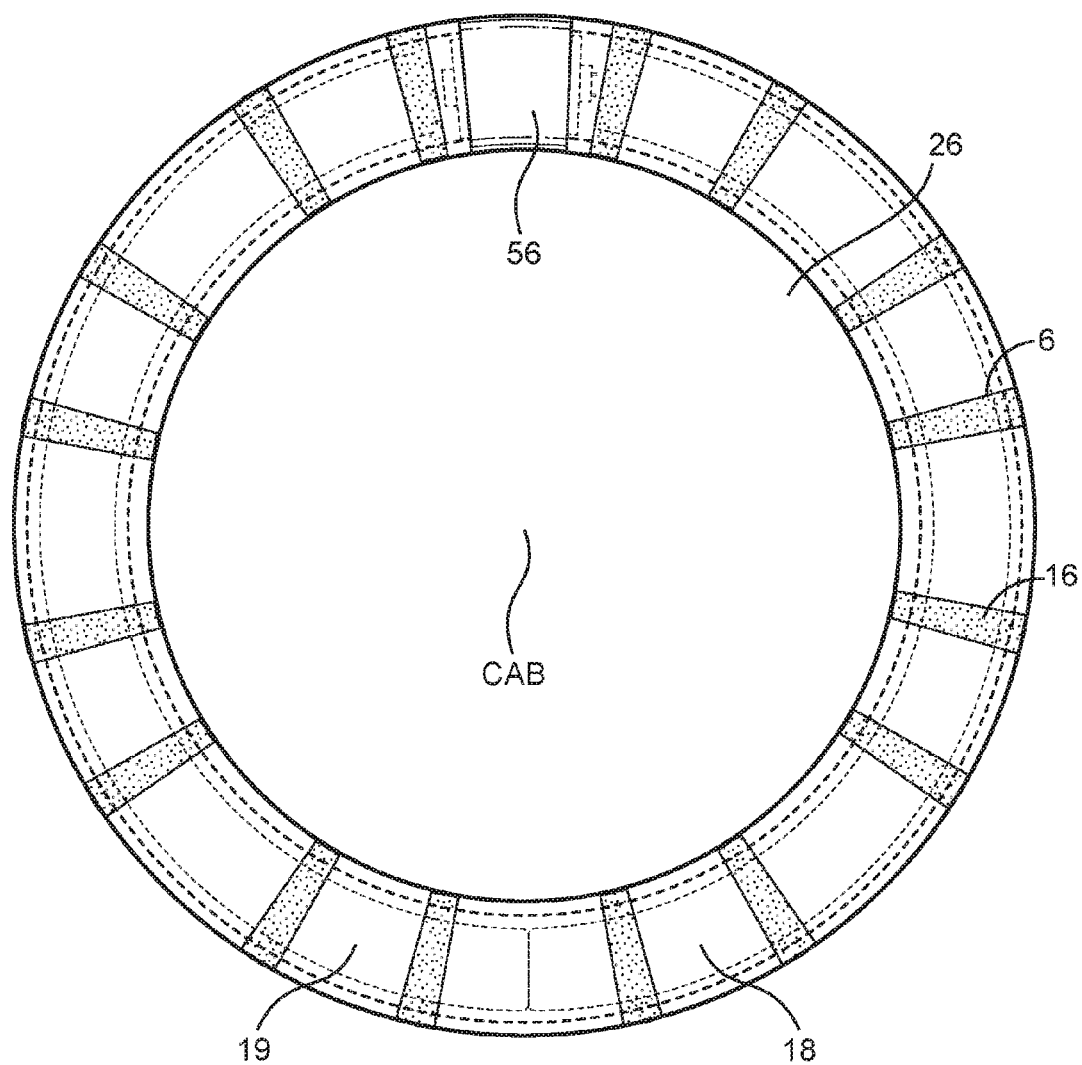
FIG. 8 is a top view of the device showing the electrodes.

The main body 4 has an elongate cavity 48 (see FIGS. 14A and 14B) in which the control system 18 and the battery 20 are positioned as shown in FIG. 8. The battery 20 and control system 18 are directly coupled together. The electrodes 16 are coupled to the control system 18 with a wire 52 (or other suitable conductive element) electrically coupled to each of the electrodes 16. The wires 52 extend through a sidewall 54 of the main body 4 and are directed toward a hub 56 which electrically couples each of the wires 52 to the control system 18. The hub 56 is positioned between a first connector 58 and a second connector 60. Half of the wires 52 are directed to each of the first and second connectors 58, 60 (eight wires 52 for each of the connectors 58, 60 in the preferred embodiment of FIG. 8). The wires 52 terminate at wire contacts 62 which are used to electrically couple the wires 52 to the hub 56 and, in turn, to the control system 18 as now described. Referring to FIGS. 14A and 15A, the electrode 16 may wrap around from a radially outer surface 53 to a radially inner side 55. An alternative electrode 57 is shown in FIGS. 14B and 15B in which the electrode 57 does not wrap around to a radially inner side 59 thereby potentially minimizing stimulus transmitted through the cervix. All features, devices, embodiments and methods described herein may use either the electrode 16 or electrode 57.

Figure 13:
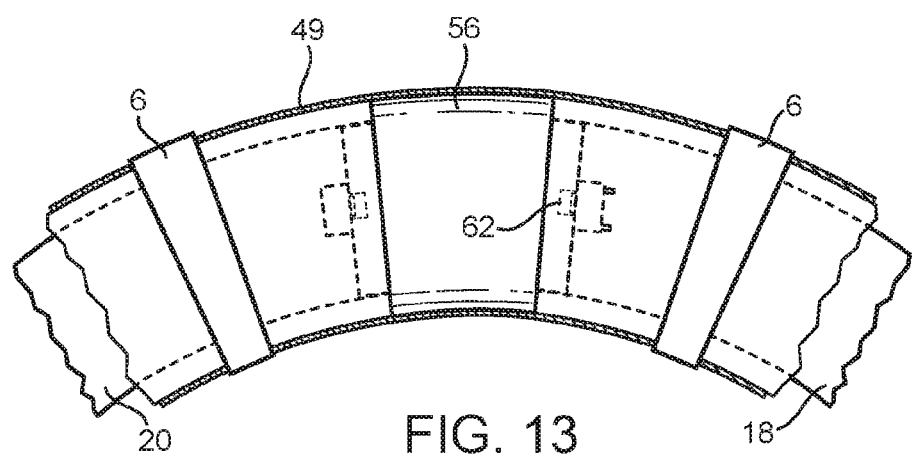
FIG. 13 shows a layer applied over the main body to seal the battery and control system within the main body.
Figure 16:
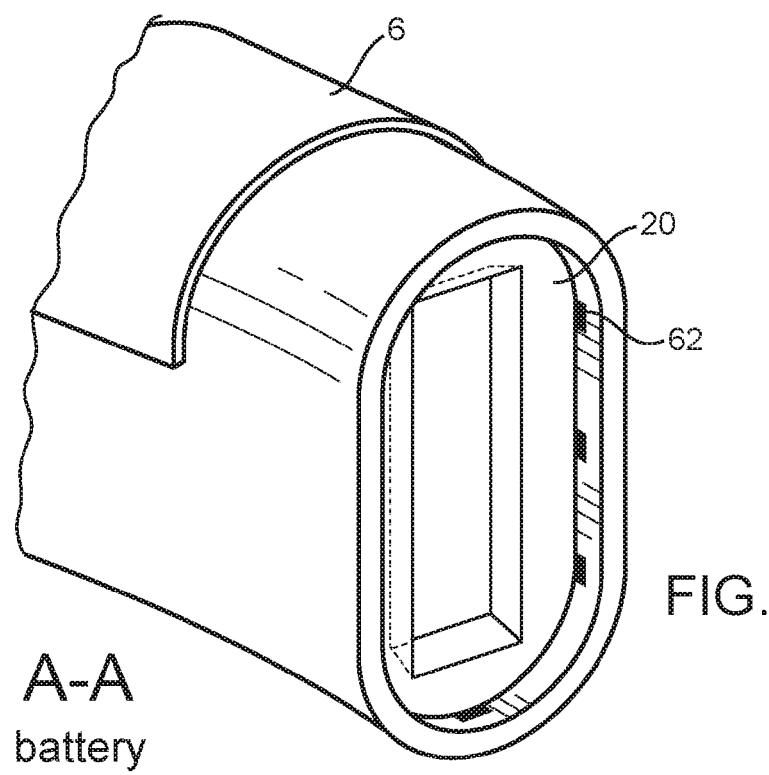
FIG. 16 is a perspective view of the end of the main body with the battery positioned in the main body.
Figure 17:
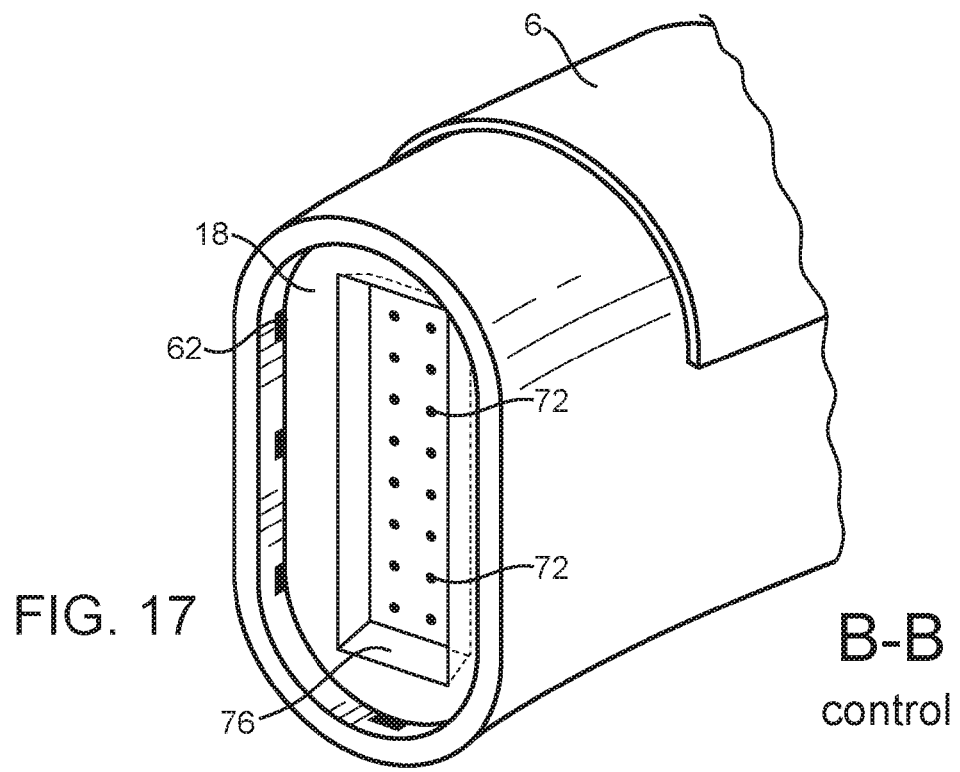
FIG. 17 is a perspective view of the end of the main body with the control system positioned in the main body.

Referring to FIGS. 10-19, the hub 56 has a protrusion 64 on each end that fits within the cavity 48 in the main body 4. The protrusion 64 on the battery 20 side abuts directly against the battery 20 (see FIGS. 16 and 18) and the other protrusion 64 abuts against the control system 18 (see FIGS. 17 and 19). The protrusion 64 includes hub contacts 66 on a radially outer wall that are aligned and electrically coupled to the wire contacts 62 at each of the first and second connectors 58, 60. Wires (not shown) leading from the hub contacts 66 are directed through the hub 56 to the control system 18. Each of the wires terminates at an electrical connector 70 (FIG. 19) that engages electrical connectors 72 on the control system 18 (FIG. 17). The electrical connectors 72 may be formed on a first extension 74 of the hub 56 that forms a snap fit connection with a recess 76 in the control system 18. A second extension 77 on the other side of the hub 56 may form a snap fit connection with the battery 20 (FIG. 18). Of course, the device 2 may prevent access to the battery 20 and control system 18 rather than providing the snap fit connection. For example, the entire device 2 may be encased in a polymer 49 to remove spaces and voids and to seal all connections to the hub 56 while leaving the electrodes 16 exposed as shown in FIG. 13.

Figure 9:
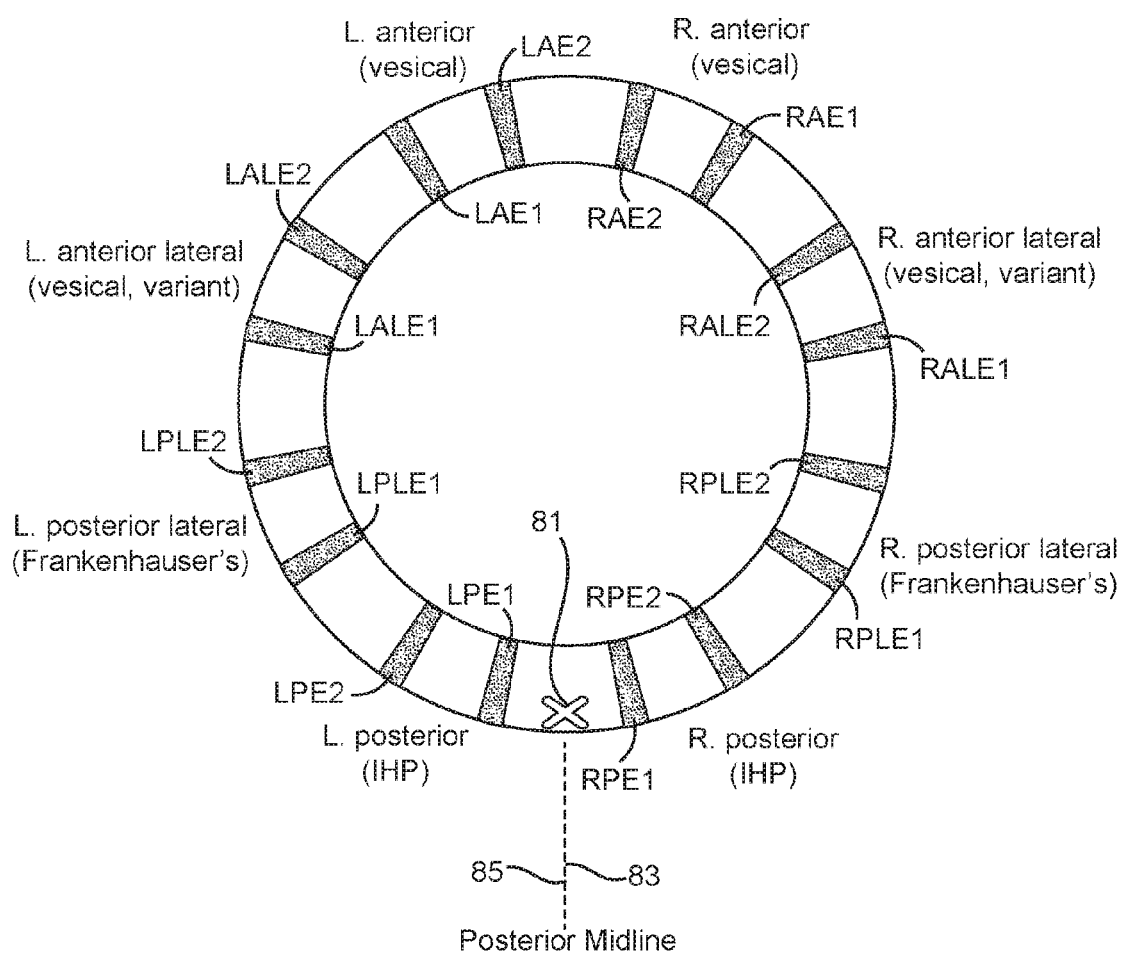
FIG. 9 shows the orientation of the electrodes.
Figure 10:
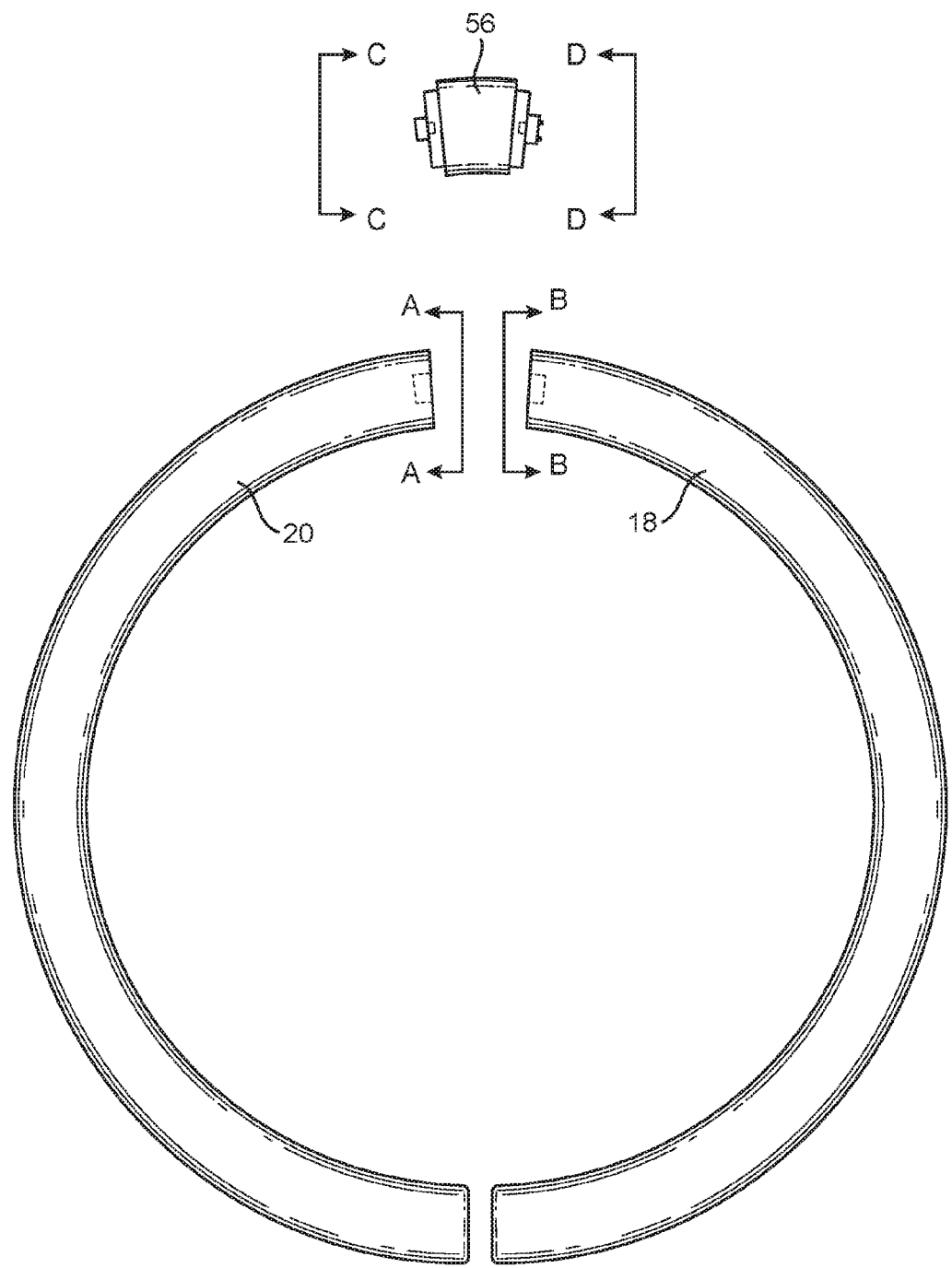
FIG. 10 shows a battery, control system and hub, which interconnects the control system with the electrodes.
Figure 11:
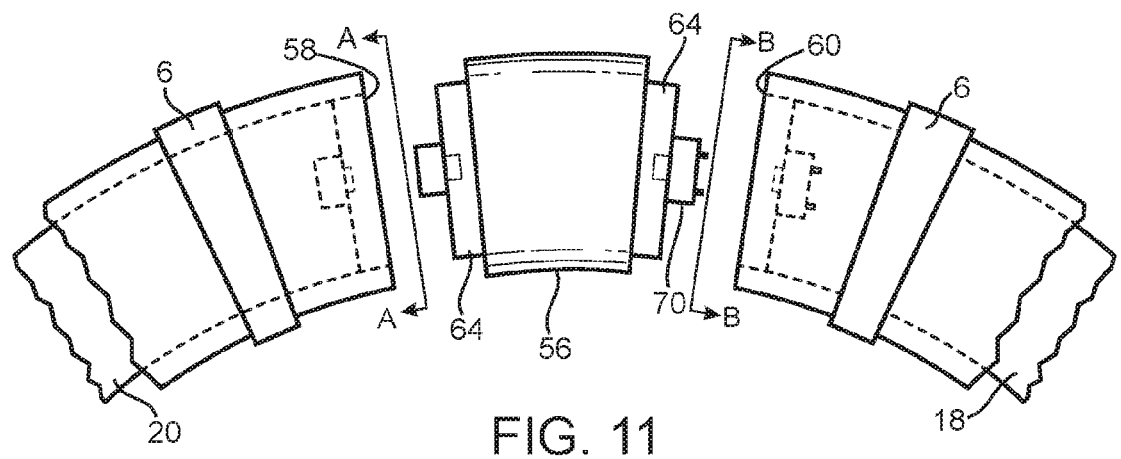
FIG. 11 is an exploded view of the hub, battery and control system.
Figure 12:
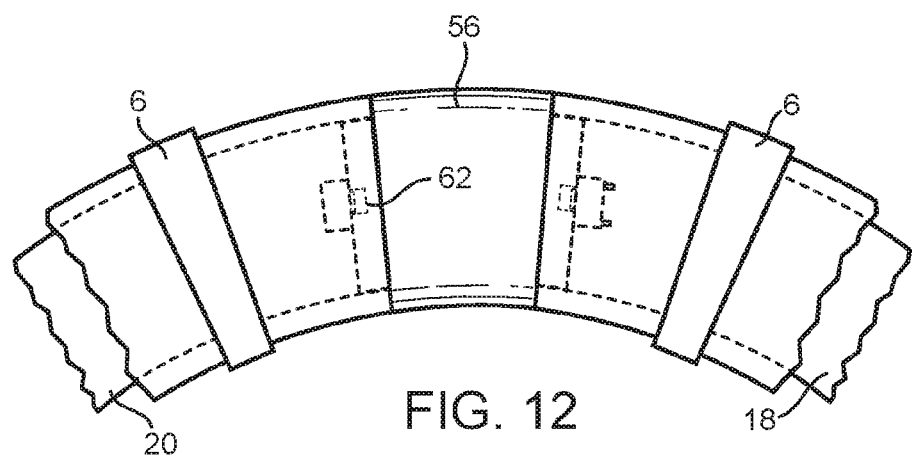
FIG. 12 shows the hub connected to the battery and control system.

Referring now to FIG. 9, the electrodes 16 may be paired together to stimulate a specific nerve plexus, and even a specific side of the plexus, as now described. The device 2 includes a marker 81 to orient the device 2 along a midline 85 which generally corresponds with a midline 83 of the user. Adjacent the marker 81 is a left posterior electrode pair LPE1, LPE2 and a right posterior electrode pair RPE1, RPE2. The left and right posterior electrode pairs are positioned to lie adjacent to the left and right sides of the inferior hypogastric plexus. A left posterior lateral electrode pair LPLE1, LPLE2 and a right posterior lateral electrode pair RPLE1, RPLE2 are positioned to lie adjacent the left and right Frankenhauser's plexuses, respectively. Finally, the vesical plexus may be targeted on the left side with a left anterior lateral electrode pair LALE1, LALE2 and a left anterior electrode pair LAE1, LAE2 while the right side of the vesical plexus may be stimulated with a right anterior lateral electrode pair RALE1, RALE2 and a right anterior electrode pair RAE1, RAE2. Thus, the present invention may be useful in stimulating the same plexus from the right side and the left side simultaneously, independently and/or at different times. Of course, the user may only actuate the left or right side rather than alternating sides for stimulation if the therapy is tolerated better or more successful on one side or the other. The control system 18 may change the laterality periodically such as every few days.

Although the above description presents distinct electrode 16 pairings, it is understood that any of the electrodes 16 may be grouped together by the control system 18 for generating nerve stimulus. For example, the two electrodes 16 on opposite sides of the marker 81 may be used to stimulate the inferior hypogastric plexus along the midline 85 rather than preferentially on the left or right sides. In another example, the left hypogastric nerve (and the junction of this nerve and the IHP) may be stimulated using the LPE2 and the LPLE1 electrodes while the right hypogastric nerve (and the junction of this and the IHP) may be stimulated using the RPE2 and the RPLE1 electrodes. Although the independent stimulation of different regions of the same plexus has been described with respect to left and right sides of the midline of a particular target plexus, the stimulation may take place at any two different regions of the same plexus rather than simply left and right sides as described in further detail below.

Although only one electrode 16 is used on each side of the circuit described above, two or more electrodes 16 may be used to create either side of the electrical circuit rather than using only one for each side as described above. In another aspect of the present invention, the device 2 may include at least twelve electrodes 16 and in the preferred embodiment sixteen electrodes 16. The nerve stimulating element 6 may be formed by any two electrodes 16 (or groups of electrodes 16) and, thus, the device 2 could easily have at least twenty nerve stimulating elements formed by sixteen electrodes 16 by grouping electrodes together, and "skipping" over one or two electrodes 16 (or more) to form the electrode pair rather than using adjacent electrodes 16 to form the pair. An advantage of forming at least twenty different nerve stimulating elements 6 the device 2 may provide greater flexibility of treatment, reduce habituation and targeting different sides of the same plexus at different times as described herein. Skipping electrodes 16 to form a particular nerve stimulating element 6 will increase a spacing between the electrodes 16 (compared to adjacent pairs of electrodes 16) thereby providing the ability to potentially alter the depth of penetration of the stimulus. The control system 18 is configured to independently actuate each of the nerve stimulating elements 6. In this manner, the device 2 of the present invention may operate in at least twenty different modes with each mode being represented by a distinct nerve stimulating element 6 formed by a unique group of electrodes 16 in any manner described herein. Thus, the present invention not only is able to target numerous plexuses with a single device 2 but each of these plexuses may be stimulated in a variety of independent modes. For example, the IHP may be stimulated with the four posterior electrodes 16 (LPE1, LPE2, RPE1, RPE2) in at least four modes (or stated another way by forming at least four different nerve stimulating elements) to stimulate the IHP. In fact, the four posterior electrodes 16 may form at least eight different modes (or stated another way by forming at least eight different nerve stimulating elements 6) to stimulate the IHP by simply grouping electrodes 16 in the manner described herein (adjacent pairs, skipping one, skipping two, grouping two or more electrodes on one side of the circuit or on both sides of the circuit). In this manner, different regions or portions of the same plexus may be stimulated. Of course, the regions stimulated will have overlapping portions but use of different electrode 16 configurations described herein will create different stimulus patterns and regions. Although the device 2 of the present invention may form numerous independent nerve stimulating elements 6, simultaneous actuation may produce fewer nerve stimulating elements 6 (such as eight when using sixteen electrodes 16), nevertheless, the device 2 still may form far more nerve stimulating elements 6 for independent actuation as described herein. The nerve stimulating elements 6 are also preferably formed by more than mere modification of power, frequency or another parameter for the same nerve stimulating element 6. As such, the nerve stimulating element 6 may each have a unique position in that the electrodes 6 are grouped, paired or otherwise organized in a unique manner for each of the nerve stimulating elements 6 formed. As such, each nerve stimulating element 6 formed has a unique position even if a grouping or pair share one or more electrodes 6 so long as the groups or pairings are not identical. Each unique position provides a different focus unlike a single nerve stimulating element that can only change power, frequency or some other characteristic while leaving the stimulation pattern substantially the same.

Although numerous nerve stimulating elements 6 may be formed with the electrodes 16 forming numerous different nerve stimulating elements, in some aspects of the invention the device 2 may have at least four, or at least eight, nerve stimulating elements 6 as described above. Each of the nerve stimulating elements 6 may be actuated independently (or simultaneously, of course) to stimulate different regions of tissue (although these regions may overlap). In another aspect of the invention, the nerve stimulating elements 6 are advantageously distributed around the main body 4 to independently stimulate the various target plexuses. To this end, the device 2 may include at least three nerve stimulating elements 6 which are angularly spaced at least 70 degrees from adjacent nerve stimulating elements relative to the cervical axis CVA or central axis of the main body 4 CAB. If more regions are targeted, the device 2 may include at least four nerve stimulating elements which are angularly spaced at least 50 degrees from adjacent nerve stimulating elements relative to the cervical axis CVA or central axis of the main body 4.

Although the nerve stimulating element 6 has been described with respect to pairs of electrodes 16, the nerve stimulating element 6 may be formed by a single element or even a single electrode 16 without departing from the scope of the invention. For example, a single piezoelectric element may be used to deliver ultrasound energy or the device 2 may include a single electrode 16 with the other electrode carried by another element (even an implantable element) without departing from the scope of the invention.

As mentioned above, many conventional devices introduced into the vagina suffer from the drawback that they often stimulate somatic nerves since these devices are typically positioned in the distal (lower) half of the vagina. These devices also often intend to stimulate pelvic muscles, which may lead to further disadvantages described herein. The present invention avoids these drawbacks by positioning the device 2 in the proximal half of the vagina and, in some embodiments, may have all of the nerve stimulating elements 6 (or electrodes 16) in the proximal half of the vagina. To this end, the present invention provides nerve stimulating elements 6 that are positioned close to the target plexuses; the vesical plexus, left and right Frankenhauser's plexuses, the inferior hypogastric plexus and the intersection of junction between the inferior hypogastric plexus and the left and right hypogastric nerves. These nerve plexuses travel close to the proximal end of the vagina as shown in FIGS. 1-3 and typically have branches within 1-2 cm from the exposed surface ES of the vagina and, as such, the preferred embodiments are described with the nerve stimulating element 6 being no more than 3 cm from the target nerve plexus. Stated another way, the nerve stimulating element 6 may be positioned no more than 3 cm from the uterosacral ligaments which are adjacent the target nerve plexuses. Stated still another way, the nerve stimulating element 6 is positioned to stimulate the vesical plexus, Frankenhauser's plexus, or inferior hypogastric plexus without intervening nerves, and in particular without intervening somatic nerves. Stated yet another way, the nerve stimulating element 6 may be positioned to contact the exposed surface 10 of the vagina closer to the vesical plexus, left or right Frankenhauser's plexus, left and right hypogastric nerves or the inferior hypogastric plexus, than to the pelvic floor. Stated still another way, the nerve stimulating element 6 (and in some embodiments all of the nerve stimulating elements 6) is positioned to contact the exposed surface ES of the vaginal canal within 3 cm from a proximal end of the vagina or proximal to a distal end of the cervix C. The entire device 2 may be positioned proximal to a midpoint between the proximal and distal ends of the vagina. Stated another way, the entire device 2 may be positioned within 5 cm from the proximal end of the vagina. Stated still another way, the nerve stimulating elements 6 are all positioned proximal to a midpoint between the proximal and distal end of the vaginal canal.

The electrodes 16 are also oriented and organized so that they will form nerve stimulating elements 6 that will generally direct stimulus proximally. To this end, the electrodes 16, and the nerve stimulating elements 6, are organized so that a proximal surface 13 are at the same longitudinal position relative to the central axis of the body CAB and the cervical axis CA. Although the electrodes 16 and nerve stimulating elements are preferably oriented in this manner, they may be longitudinally separated without departing from numerous aspects of the present invention. For example, the electrodes 6 (and in one aspect all of the electrodes 16 or nerve stimulating elements 6) may be longitudinally spaced so that the proximal surface 13 of the electrodes 6 (and the nerve stimulating element 6 formed by the electrodes 16) relative to the central axis of the body CAB or the cervical axis CVA by no more than one cm.

Figure 20:
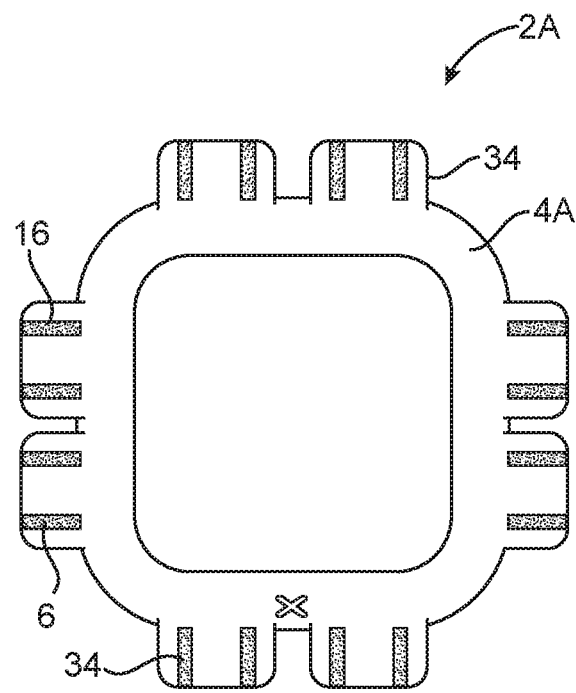
FIG. 20 shows a top view of another device in accordance with the present invention.

Referring now to FIG. 20, another device 2A is shown including a main body 4A having one or more tabs 34 extending radially outward relative to a central opening 26A. The tabs 34 may help secure the device 2A in place and maintain the intended orientation of the device 2A once positioned. The electrodes 16 may be positioned on the tabs 34 so that the electrodes 16 are on the radially outer surface of the main body 4A.

Referring to FIG. 21, still another device 2B is shown which has an extension 36 extending radially outward from the main body 4. The extension 36 has a first curved tip 38 and a second curved tip 40 which help anchor the device 2 in position and help maintain the intended orientation. The main body 4B may also be flared outwardly which also may help retention. The main body 4B is flared outwardly to become larger as the body 4B extends distally in the vagina. It is understood that all of the devices 2, 2A, 2B described herein shall incorporate all methods of using the other devices 2, 2A, 2B and such use is expressly incorporated for each device described herein. Furthermore, all devices 2, 2A, 2B shall share the same inventive features described herein and such features are also expressly incorporated for all devices described herein. For example, the position and use of the electrodes 16 of device 2 shall be applicable to use of device 2A and device 2B.

The device may also be used to stimulate the vesical plexus together with either the Frankenhauser's plexus or with the inferior hypogastric plexus (or both). The vesical plexus may be stimulated independently or simultaneously with one or both of the other two plexuses. In another aspect, an anterior side may be stimulated simultaneously or independently with a posterior side.

As can be appreciated, the present invention provides the ability to target more than one plexus and, alternatively, the same plexus from a different position. For example, a plurality of nerve stimulating elements 6 are positioned to stimulate the same plexus for each of the plexuses described herein. Switching to different stimulating elements 6 may reduce habituation and/or provide other therapeutic benefits. Furthermore, the user may simply select, based on efficacy determined by the user, which of the areas is most beneficial for the particular treatment. Of course, a computer-controlled algorithm may also be used to target particular areas due to set parameters or from feedback data. The control system 18 may control the device 2 to stimulate a target plexus with a first nerve stimulating element 6 for a first period of time, then stimulate the target plexus with a second nerve stimulating element 6 for a second period of time and independent of the first nerve stimulating element 6. In this manner, habituation may be addressed without changing the target plexus but changing the position of stimulation by changing the nerve stimulating element. Of course, the target plexus(es) may also be changed from any one (or more) of the target plexuses described herein to another target plexus(es) to address habituation or as otherwise desired.

Figure 22:
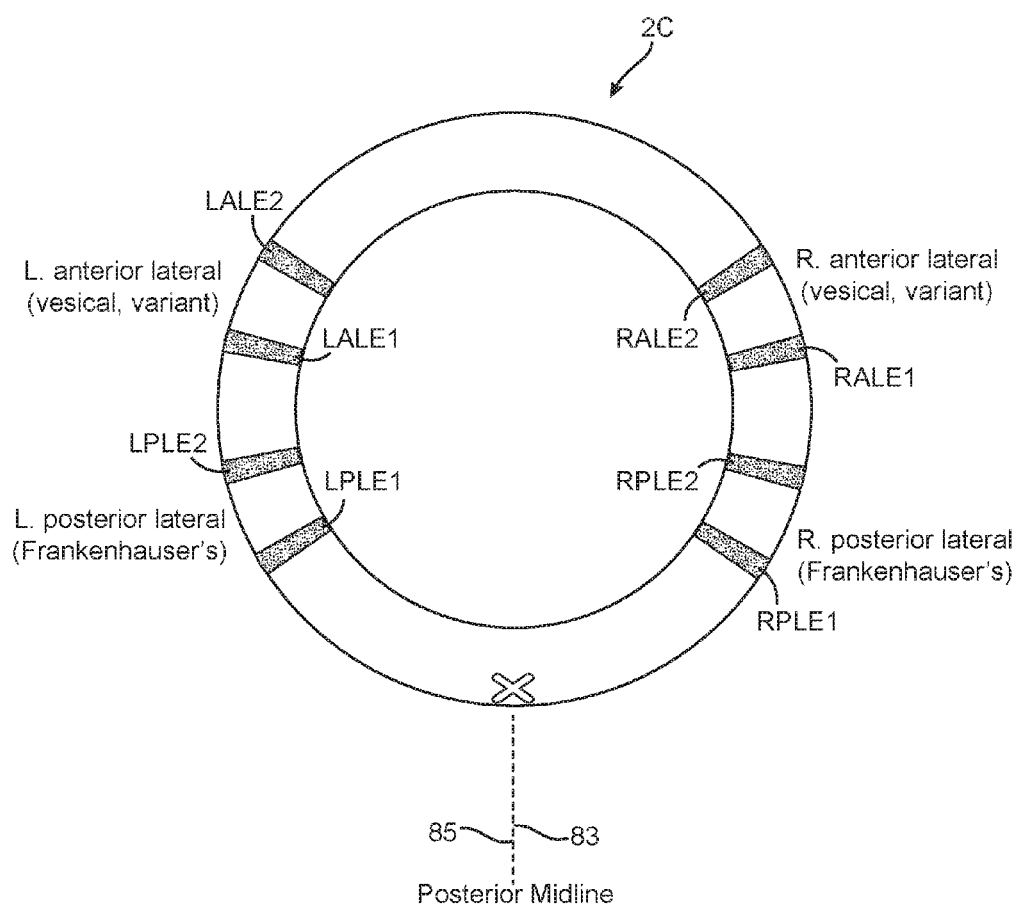
FIG. 22 shows another device for stimulating nerves.
Figure 23:
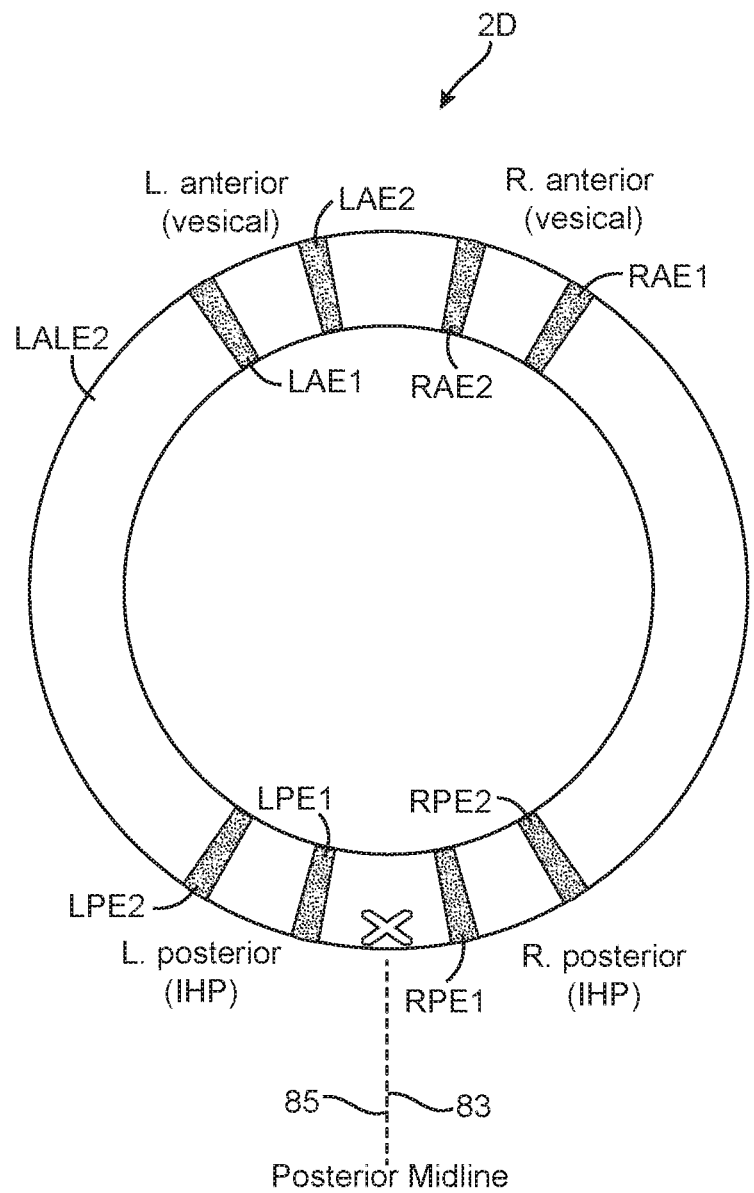
FIG. 23 shows another device for stimulating nerves for use with the device of FIG. 22.
Figure 24:
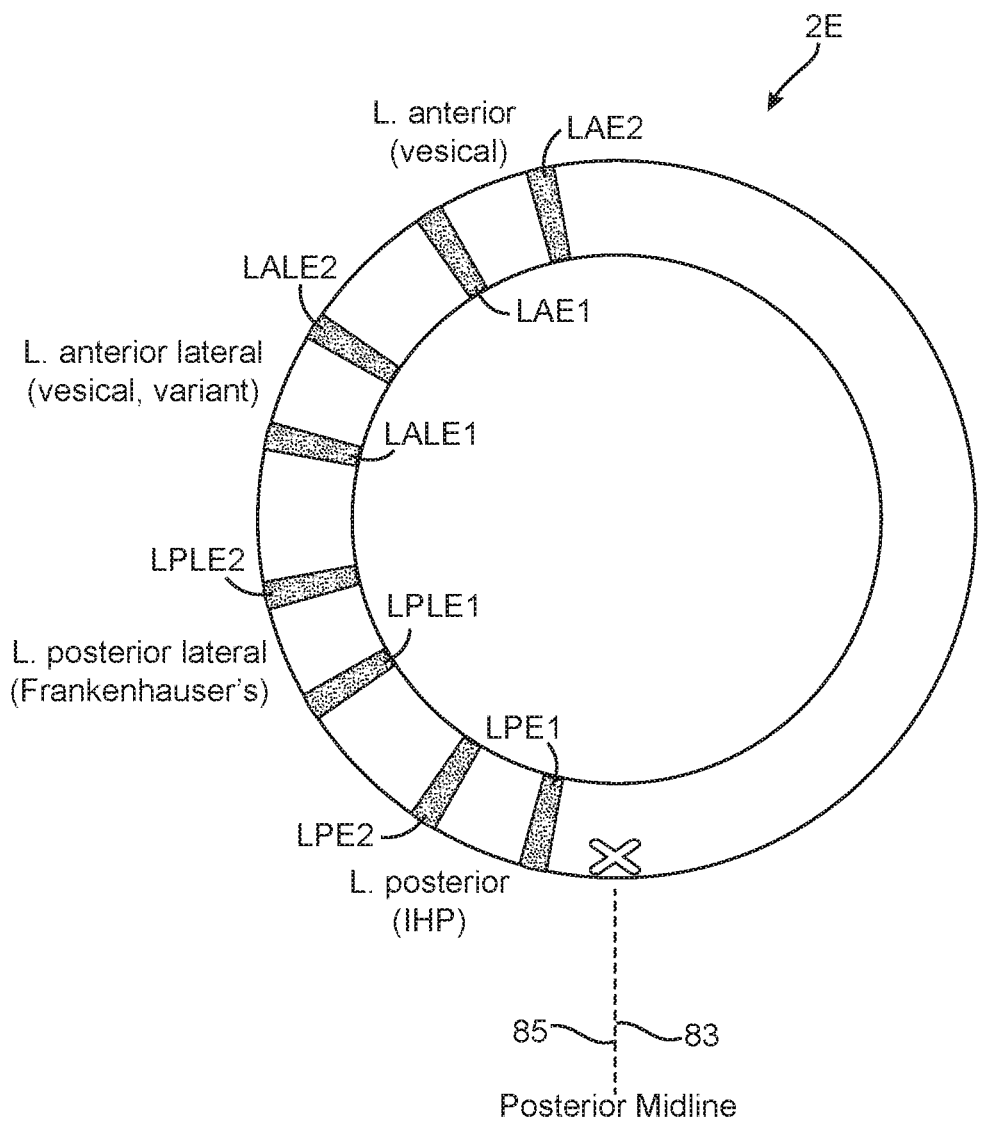
FIG. 24 shows another device for stimulating nerves.

In one aspect, a plurality of devices 2C, 2D, 2E, such as at least three, having different patterns of stimulating elements 6 may be provided as shown in FIGS. 22-24. Of course, any other suitable division of plexuses among the plurality of devices 2C, 2D, 2E may be provided. The user may switch between the devices 2C, 2D, 2E (or others with different patterns of elements) as desired. All aspects and methods of using the devices 2, 2A, 2B are incorporated here for use with the plurality of devices 2C, 2D, 2E as applicable.

Figure 25:
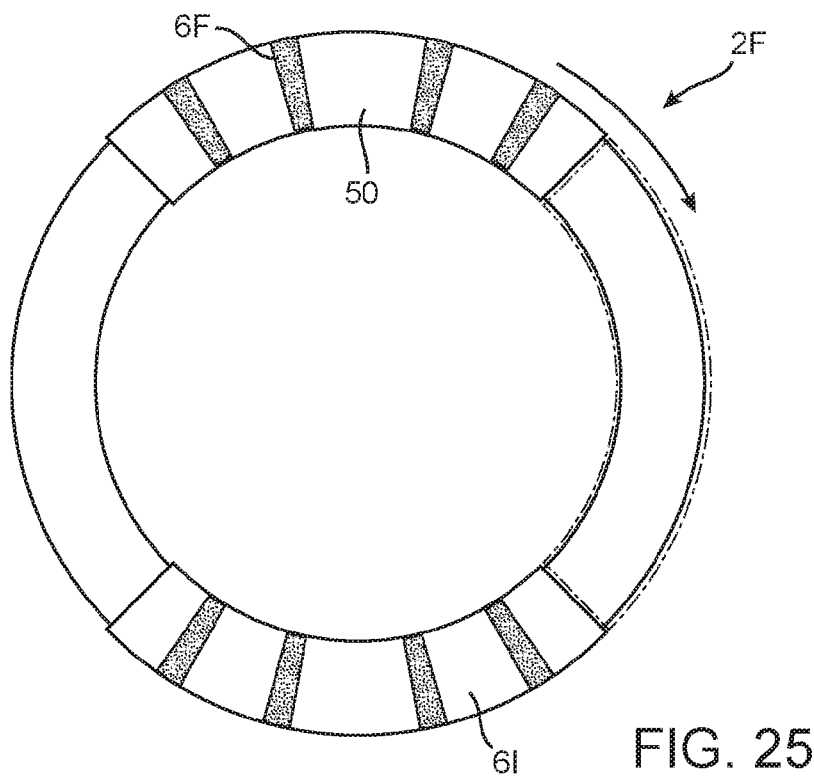
FIG. 25 shows another device for stimulating nerves with the nerve stimulating element mounted to a movable element on the main body of the device.
Figure 26:
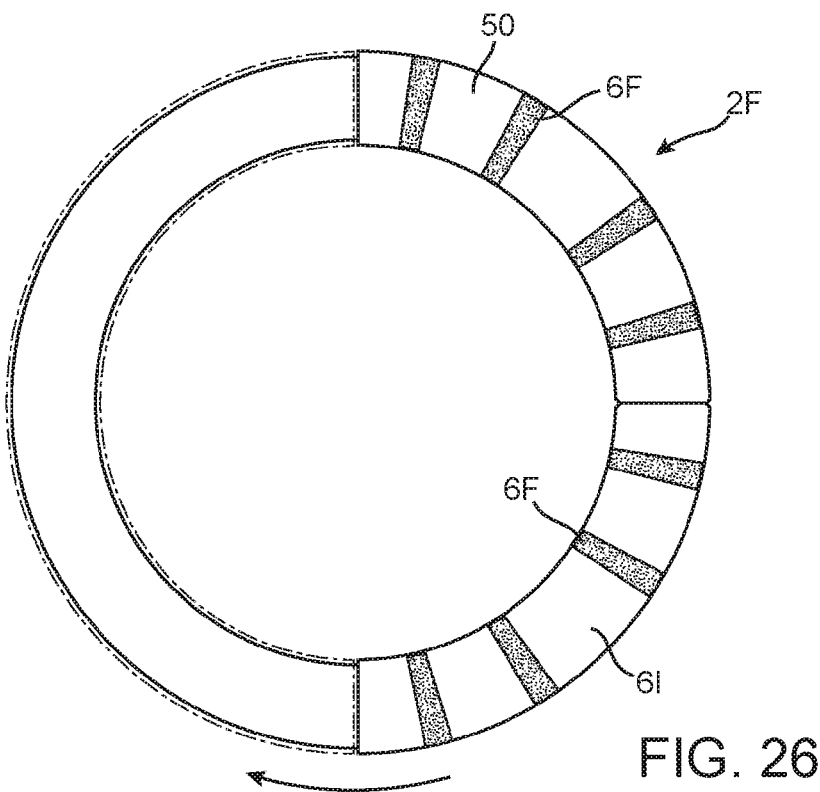
FIG. 26 shows the movable elements of FIG. 25 moved together.

Referring to FIGS. 25 and 26, the ability to select areas for stimulation may also be provided using device 2F having first and second movable elements 50,61. The first and second movable elements 50, 61 are coupled to a support body 4F which may extend in an arc of at least 270 degrees for positioning around the cervix. Each of the movable elements 50, 61 includes elements 6F for stimulating nerves and all aspects described herein of the devices 2, 2A, 2B, and 2C-2E are incorporated here. The first and second movable elements 50, 61 permit the user to move the elements 6F to desired positions for stimulating target plexuses. FIG. 25 shows the movable elements 50, 61 positioned to stimulate nerves when positioned on opposing sides of the cervix (any opposing regions). FIG. 26 shows the movable elements 50, 61 moved together to form a section, which permits stimulating half of the regions discussed herein and such uses are expressly incorporated here.

Figure 27:
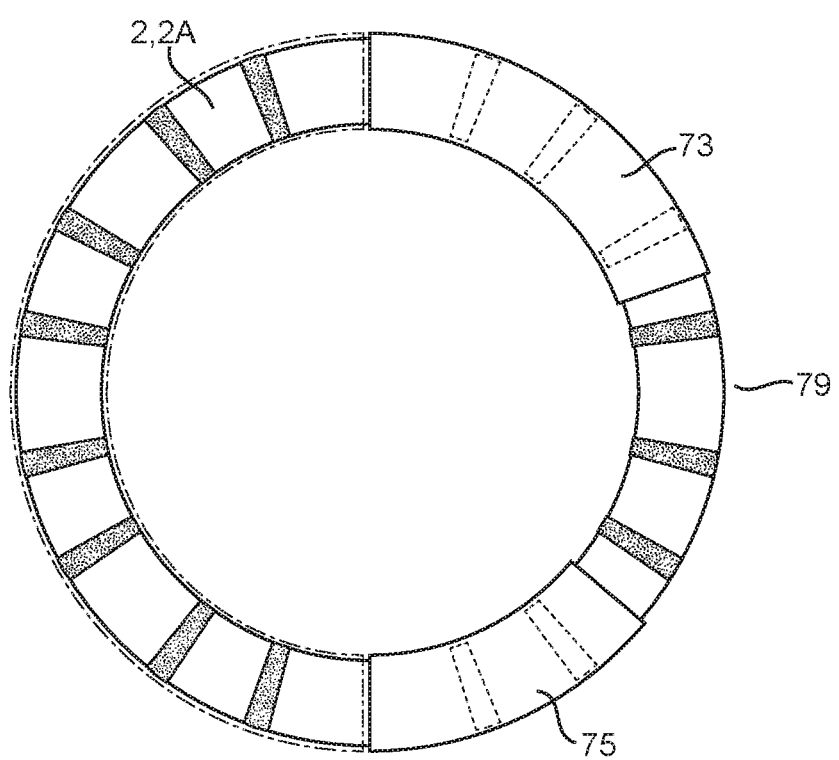
FIG. 27 shows a first cover and a second cover for covering parts of the devices described herein.
Figure 28:
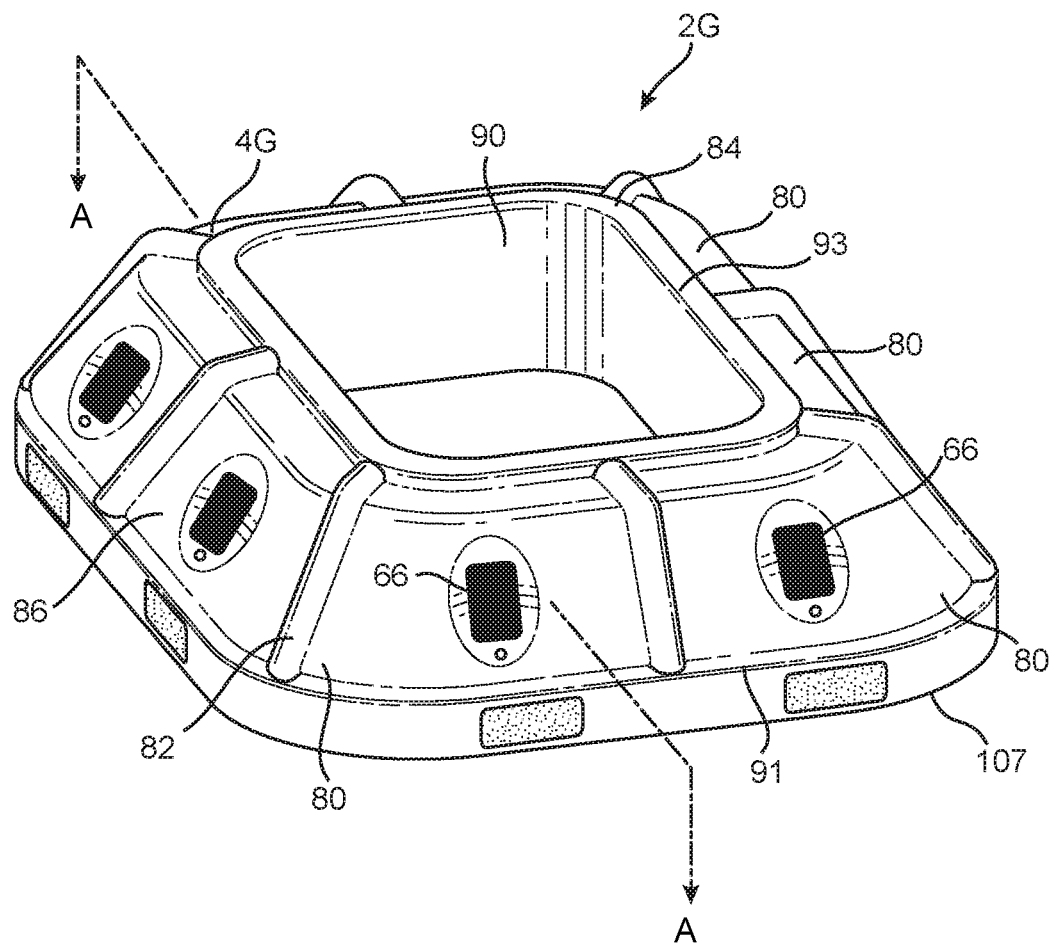
FIG. 28 shows another device for stimulating nerves.
Figure 29:
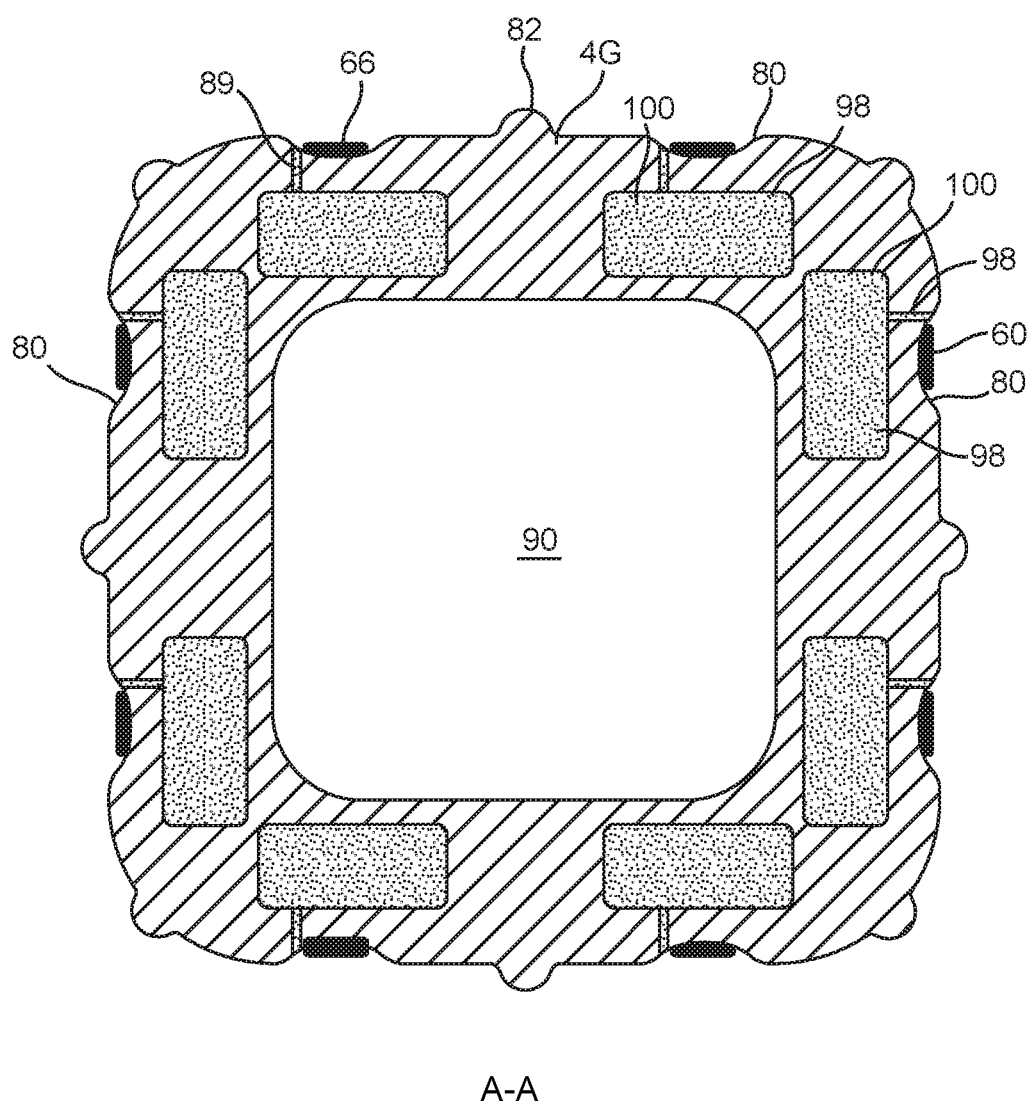
FIG. 29 shows a cross section of the device of FIG. 28.
Figure 30:
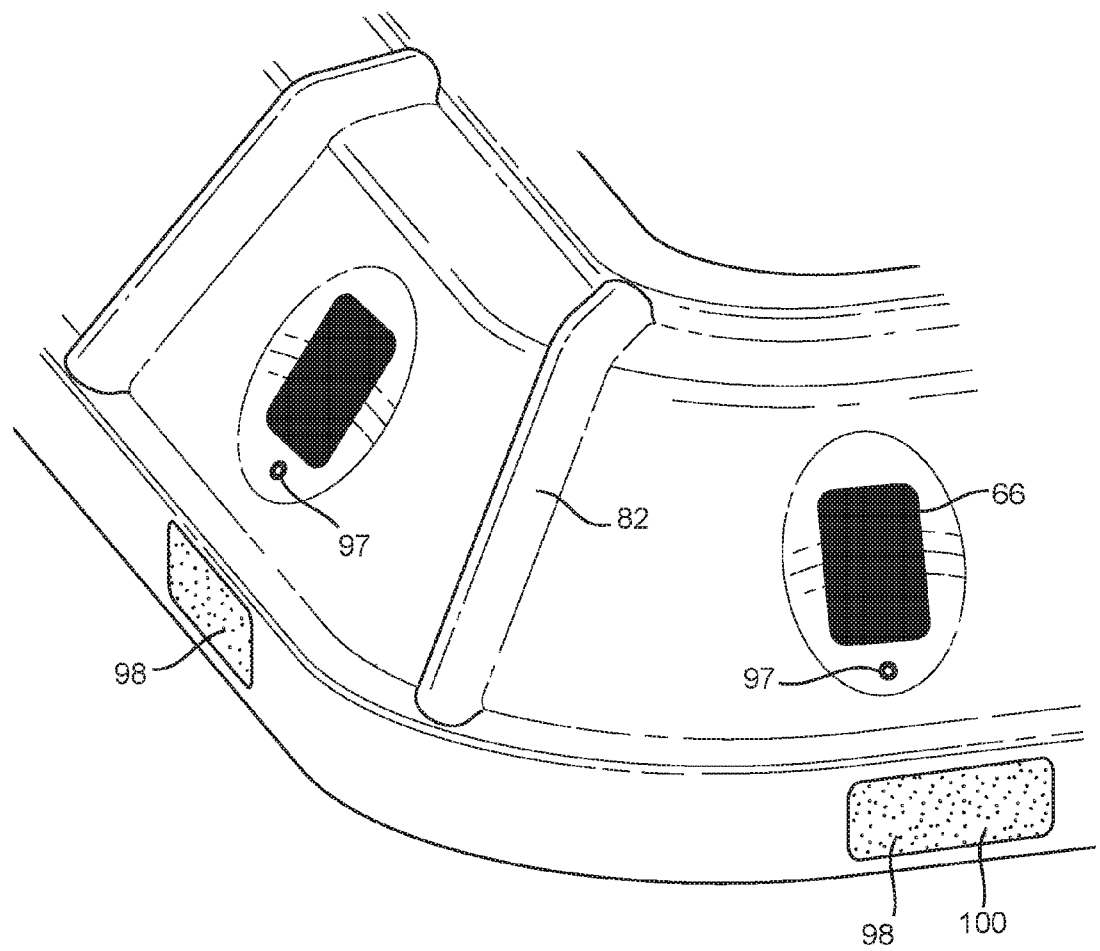
FIG. 30 shows an enlarged view of a recess of the device of FIG. 28.

Referring to FIG. 27, a first cover 73 and a second cover 75 are provided to prevent or reduce stimulating some areas for use with any of the devices 2, 2A-2F described herein. The first and second covers 73, 75 are movable along the body to cover elements 6 as desired. The first and second covers may 73, 75 may also be spaced apart to form a window 79 for stimulating tissue within the window 79.

In still another aspect of the present invention, the device 2 is now referred to again with reference to FIGS. 1-22. The device 2 itself may be used to orient the device 2 within the patient using the nerve stimulating elements 6 themselves. For example, when one of the nerve stimulating elements 6 emits energy, another of the nerve stimulating elements 6 may measure energy received from the emitting element 6. The control system 18 monitors the energy received at the other nerve stimulating element 6 and records data regarding the energy received. The control system 18 may then recognize the orientation of the device 2 relative to the cervix by recognizing a pattern in the energy received. In another aspect, the control system 18 may simply measure impedance between two or more nerve stimulating elements. The resulting impedance data may also be subsequently used to orient the device 2 with the control system 18 recognizing a pattern of data to orient the device 2. Stated another way, the control system 18 may be used to orient the device with at least one of the nerve stimulating elements emitting energy and at least one other of the nerve stimulating elements measuring the energy emitted. The control system 18 may save a pattern of a parameter and compare the pattern to current data to orient the device about the cervix. For example, RF energy or ultrasound energy may be emitted by one or more elements 6 and received at others with the control system 18 monitoring and storing the data. In another aspect, impedance between nerve stimulating elements 6 may be used with the control system 18 monitoring and storing the impedance and matching a pattern of saved impedance data to orient the device 2, 2A. The device 2 may then change the pattern of stimulation using the nerve stimulating elements 6 in accordance with the orientation determined by the control system 18. Of course, an angular shift of the device 2 around the cervix may orient different elements 6 adjacent different targets but, of course, such a shift and change of nerve stimulating elements 6 is clearly contemplated with the present invention and, as such, the particular elements 6 used to stimulate the target area (plexus) may change.

Referring to FIGS. 28-51, various additional devices are shown. As with all other embodiments in this application, all methods of use and physical characteristics mentioned herein for one embodiment are equally applicable to all other embodiments. Thus, for the embodiments of FIGS. 28-51, all methods of stimulating any of the target nerves or plexuses, or for any other therapeutic use mentioned herein, are incorporated here. For example, all devices described herein may include a first nerve stimulating element stimulating nerves adjacent the vagina, a second nerve stimulating element positioned to stimulate nerves on an opposing side of the cervix from the first nerve stimulating element when viewed along a cervical axis (independently or simultaneously and without moving the device). Similarly, all other applicable methods may be used specifically with every other embodiment. Furthermore, all physical characteristics, such as size, orientation, number and position of nerve stimulating elements, are also all incorporated here and for all embodiments described herein. Finally, although not specifically shown for each embodiment, each device includes the power supply, such as the battery, and the control system described herein and the characteristics of each are applicable to all embodiments.

Referring now to FIGS. 28-31, another device 2G for stimulating nerves is shown wherein the same or similar reference numbers refer to the same or similar structure. As mentioned above, all features of corresponding structures and methods shall be incorporated here. For example, the nerve stimulating element 6G, although shaped uniquely compared to the other nerve stimulating elements, nevertheless may incorporate any of the features of the nerve stimulating elements described above such as the nerve stimulating element 6G may be an electrode 16G. The nerve stimulating elements 6G are positioned on an exterior surface 8G of a main body 4G. The main body 4G may form a closed ring 88 having a central opening 90 in which the cervix is positioned. The term "closed ring" or "closed loop" as used herein shall mean any closed shape regardless of shape and, as such, all of the closed shapes described herein shall constitute closed rings or closed loops.

The exterior surface 8G of the main body 4G forms a truncated pyramid having four sides 92 and rounded edges. At least one nerve stimulating element (or at least two) is positioned on each side 92. Alternatively, at least three of the four sides 92 may each have at least two nerve stimulating elements 6G.

The main body 4G includes a recess 80 in which the nerve stimulating element 6G is positioned. The main body 4G may include at least four recesses 80 and at least four nerve stimulating elements 6G each positioned in one of the recesses 80. The main body 4G may also include a non-conductive wall 82 extending between the recesses 80. The wall 82 may be electrically insulated (non-conductive) to isolate the nerve stimulating elements 6G from one another. The wall 82 may also help to contain a conductive material within the recess 80 as explained further below. The main body 4G may also have another wall 84 that extends around the opening 90. The wall 84 may also be a non-conductive material to help isolate the nerve stimulating elements 6G from one another (particularly when electrodes 16 are used) and to contain a conductive material. The wall 84 is positioned between the nerve stimulating elements 6G and a radially inner edge 93 (smaller end) of a central opening 95 in the main body 4G. Another wall 91 is positioned at a radially outer edge 107 (larger end of the opening) of the central opening 90.

Figure 31:
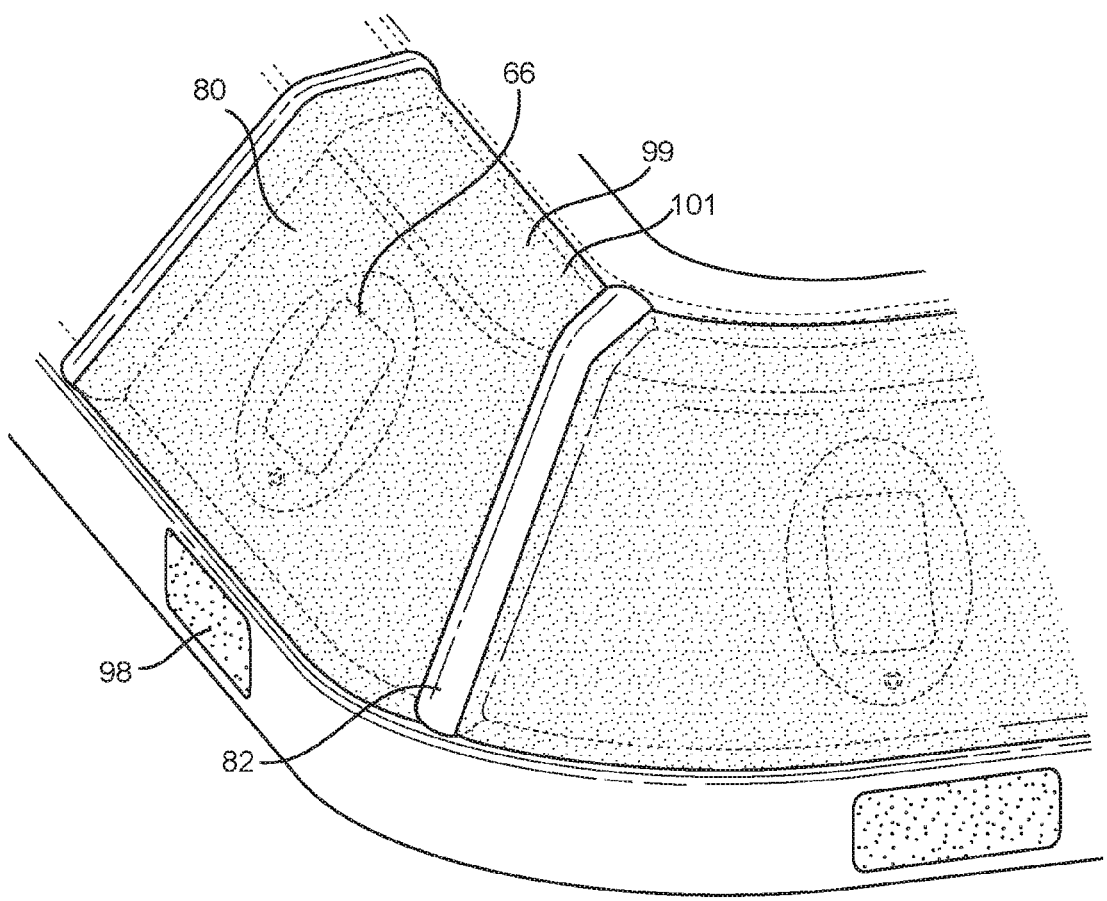
FIG. 31 shows the recess filed with a porous material, which holds an electrically conductive substance.

The main body 4G may also include a reservoir 94 which contains a flowable substance 96 such as saline or a hydrogel. The reservoir 94 has a lumen 89 fluidly coupled to the recess 80 and a permeable and/or porous structure 98 (depending on application) such as an open cell foam exposed and positioned in the recess 80. The structure 98 has pores 100 that hold the flowable substance 96 which may be electrically conductive (such as saline or a hydrogel). The flowable substance 96 may continue to weep from the structure 98, depending on the physical characteristics of the structure 98, lumen 89 and flowable substance 96, to position the flowable substance 96 in the recess 80 adjacent the nerve stimulating element 6G. The structure 98 may automatically draw the flowable substance 96 from the reservoir 94 thereby automatically replenishing the flowable substance 96 as necessary. Of course, the flowable substance 96 may also be forced from the reservoir 94 without departing from the scope of the invention. The flowable substance may be a conductive substance to enhance electrical contact between the nerve stimulating element 6G and tissue. A fill hole 97 may be used to fill the reservoir 94 as necessary. The reservoirs 94 may each deliver to a single recess 80 but may, of course, deliver to multiple recesses 80 without departing from the scope of the invention. Referring to FIG. 31, the flowable substance is shown filling the recess 80. The recess 80 may also be filled with a permeable material 99 which holds the flowable substance 96 in pores 100 therein as describe in connection with other embodiments described herein.

Figure 32:
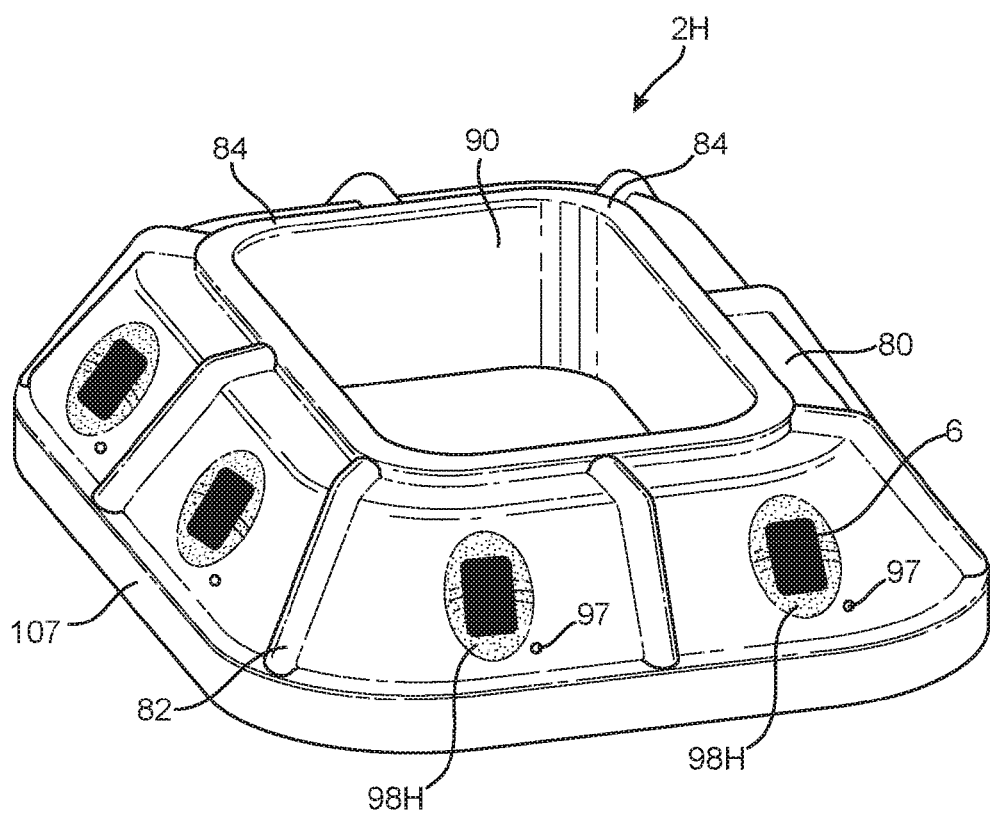
FIG. 32 shows another device for stimulating nerves.

Referring to FIG. 32, another device 2H for stimulating nerves is shown wherein the same or similar reference numbers refer to the same or similar structure. The device 2H includes a permeable and porous structure 98H surrounding the nerve stimulating element 6H. In this manner, the flowable substance 96 is delivered directly to the area around the nerve stimulating element 6H. The flowable substance 96 weeps from the permeable structure 98 and is contained within the recess 80 with the walls bounding the recess 80 helping to contain the substance 96. The walls also provide a non-conductive barrier to reduce the likelihood of a short circuit between adjacent elements 6 (particularly when using electrodes).

Figure 33:
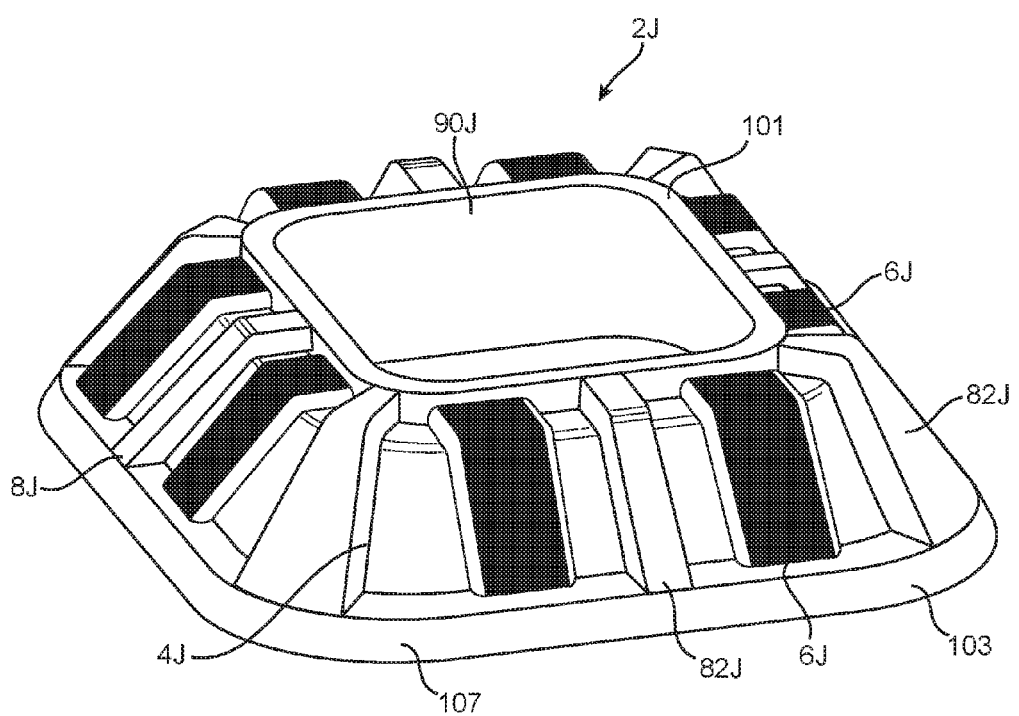
FIG. 33 shows still another device for stimulating nerves.
Figure 34:
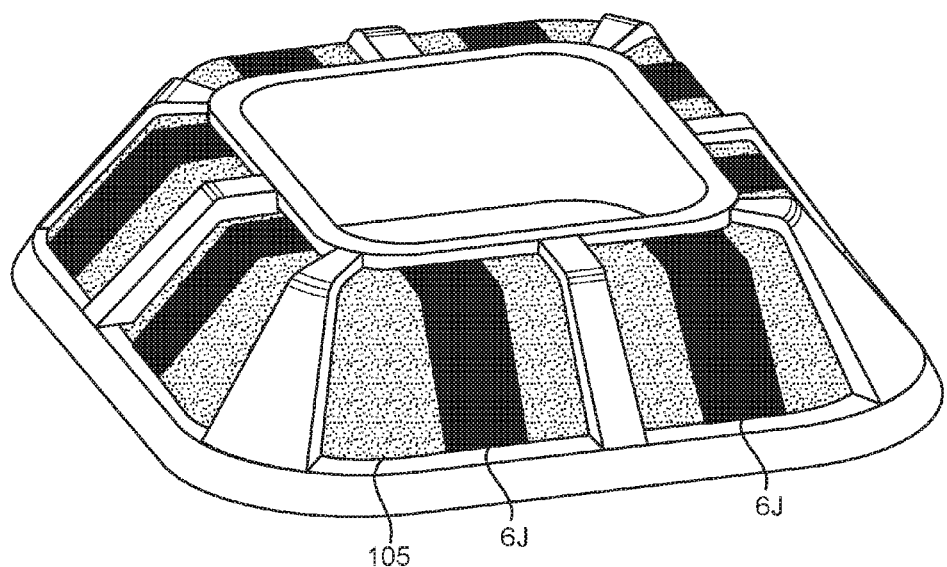
FIG. 34 shows the device of FIG. 33 with the recess filled with an electrically conductive, pliable material.
Figure 35:
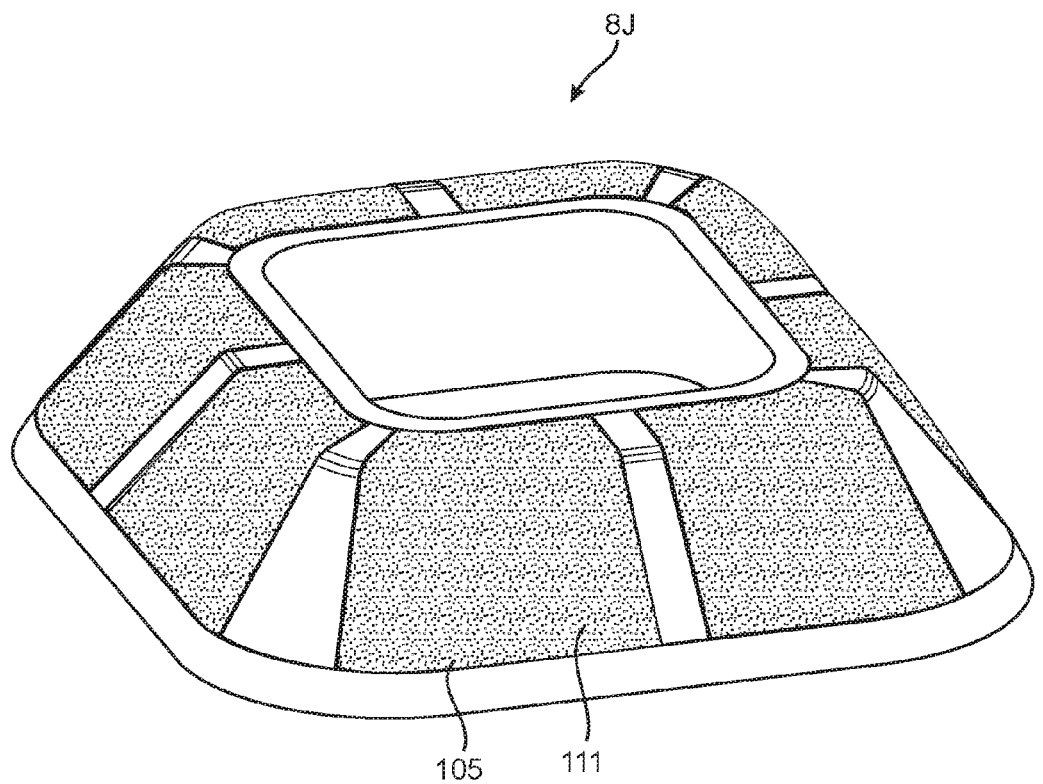
FIG. 35 shows the nerve stimulating element covered by an electrically conductive material.

Referring to FIGS. 33-35, another device 2J for stimulating nerves is shown wherein the same or similar reference numbers refer to the same or similar structure. The device 2J has nerve stimulating elements 6J on an exterior surface 8J of a main body 4J. The main body 4J may have the shape of a truncated four-sided pyramid and may include the features associated with this shape described above.

The main body 4J includes a wall 82J extending between recesses 80J. The wall 82J may be electrically insulated (non-conductive) to isolate the nerve stimulating elements 6J from one another. The wall 82J may also help to contain a conductive material 105 within the recess 80J as explained further below. The main body 4J may also have another wall 84J that extends around a smaller end 101 of central opening 90J. The wall 84J may also be a non-conductive material to help isolate the nerve stimulating elements 6J from one another (particularly when electrodes 16 are used) and to contain a conductive material. A lip 103 forms another wall 107 that extends around the larger end (radially outer side) of the central opening 90J thereby surrounding each recess 80J with walls 82J, 84J and wall 107. A conductive material 105 is positioned in the recess. The material 105 may be a soft, pliable, electrically conductive structure such as any of those described herein including a porous material or substance (using saline or a gel such as a hydrogel). In this manner, the conductive material 105 may conform somewhat to the shape of the tissue to enhance contact with tissue and electrical conduction.

Referring to FIG. 35, the nerve stimulating element 6J may be covered by a pliable, electrically conductive material 109. The conductive material 109 may also be pliable so that the conductive material 109 also conforms somewhat to the shape of the tissue. The conductive material 109 may be a permeable open cell foam element 111 with a conductive fluid, such as saline, contained in the pores of the element 111.

Figure 36:
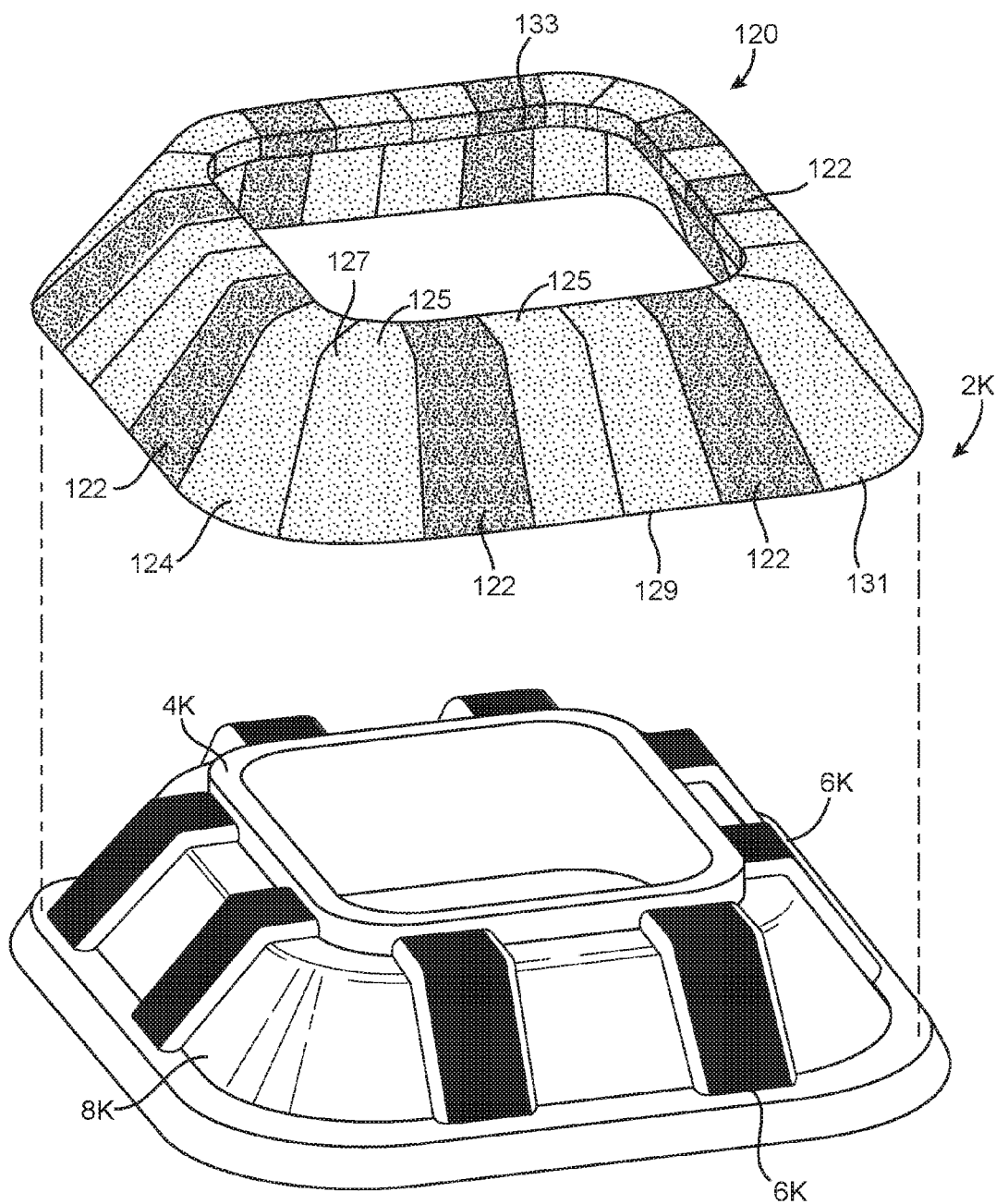
FIG. 36 shows another device for stimulating nerves having an insert with conductive and non-conductive regions.
Figure 37:
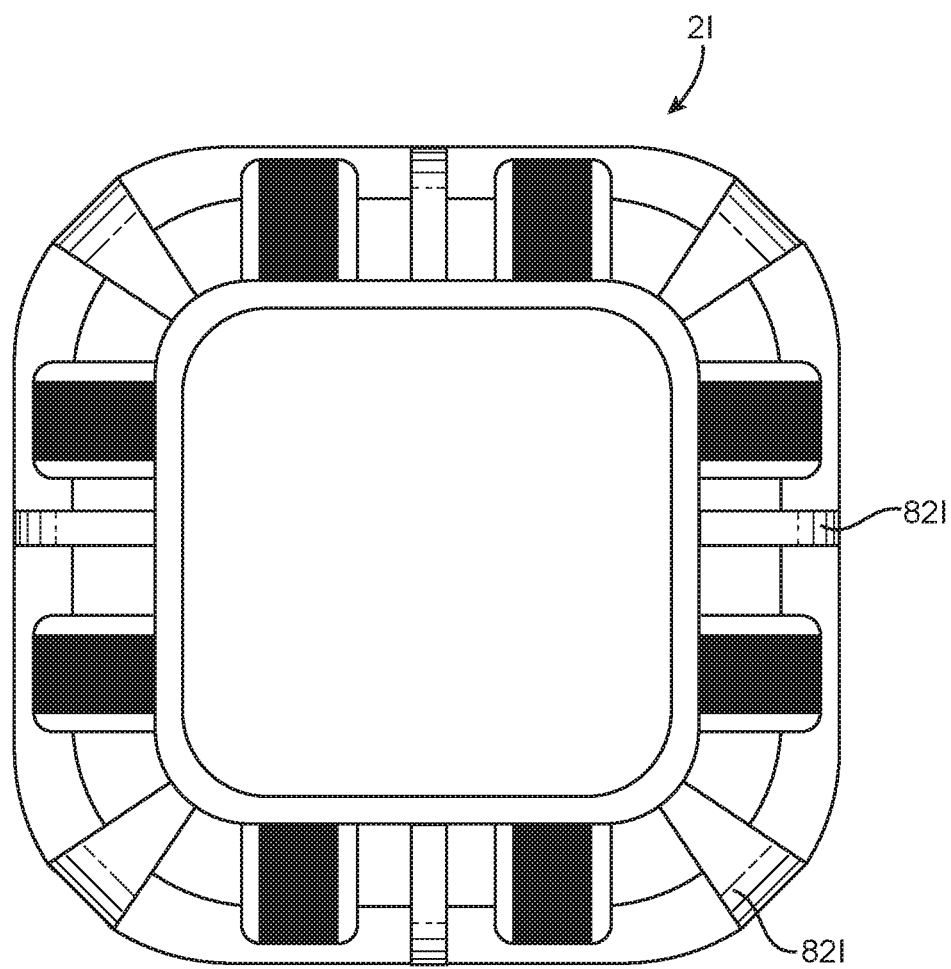
FIG. 37 is a plan view of another device.
Figure 38:
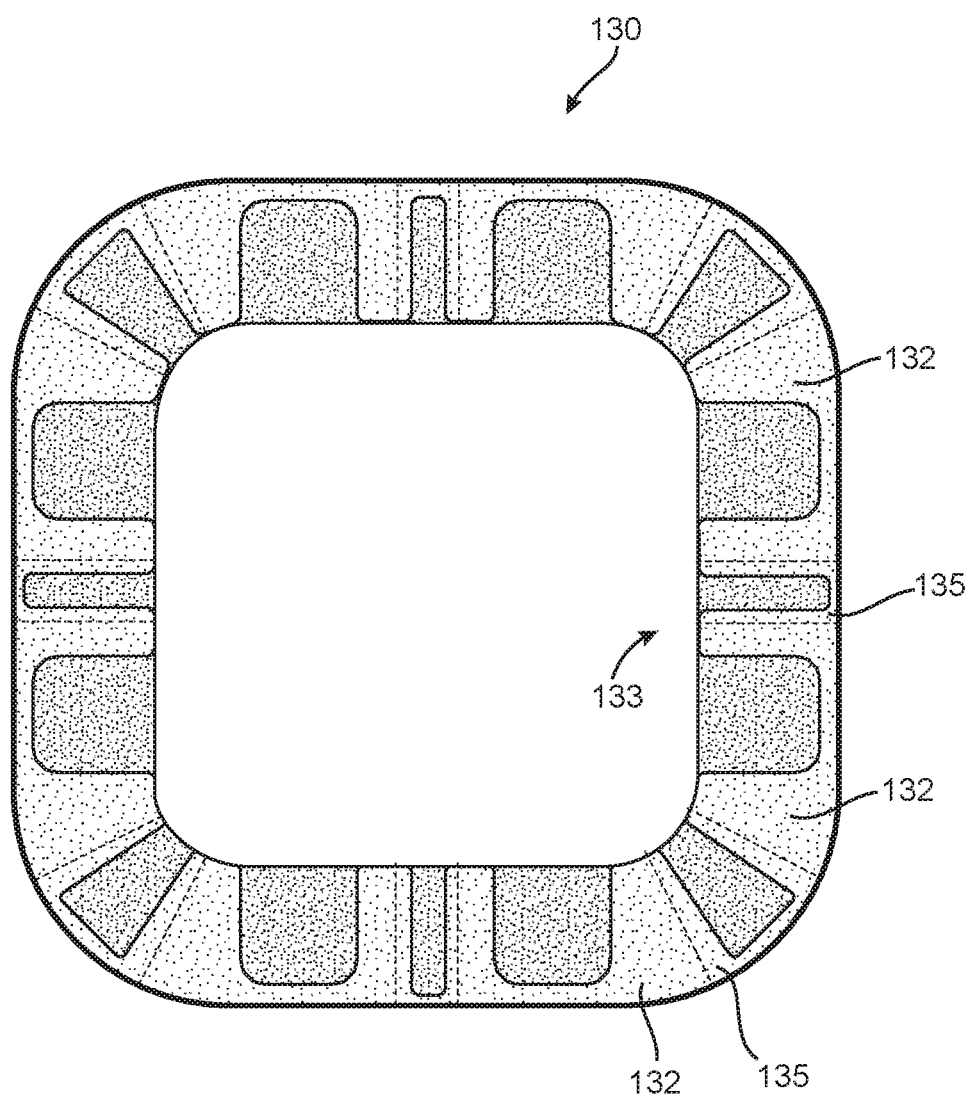
FIG. 38 is a bottom view of the insert used with the device of FIG. 37.
Figure 39:
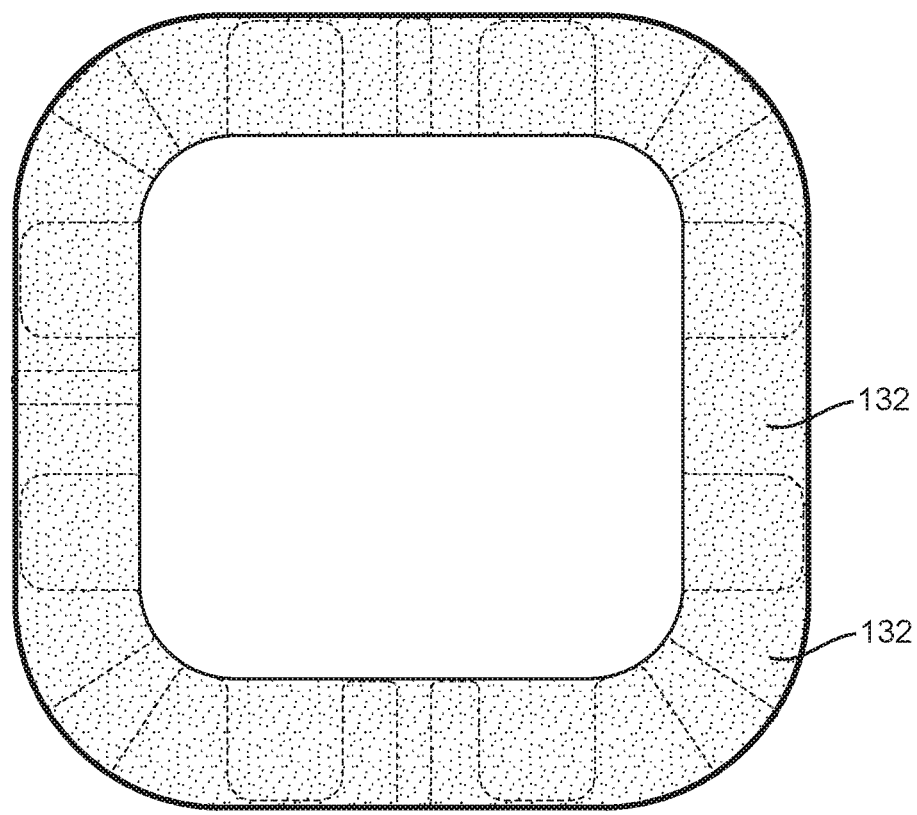
FIG. 39 is a top view of the insert of FIG. 37.
Figure 40:
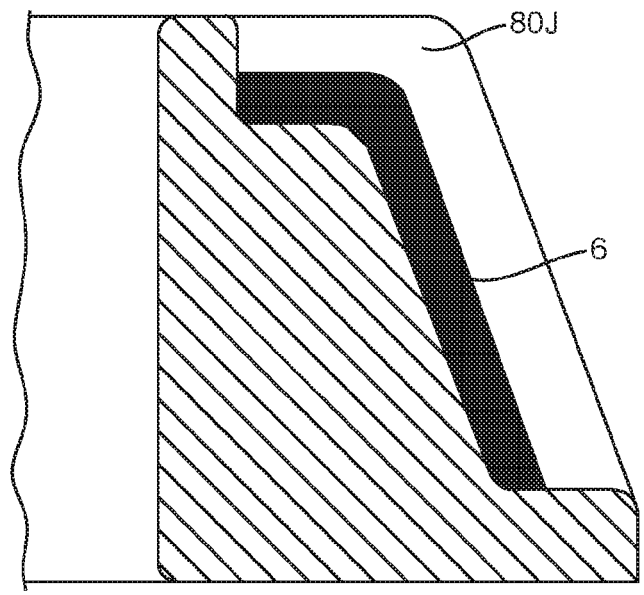
FIG. 40 is a partial cross-sectional simplified view showing the nerve stimulating element positioned in the recess.

Referring to FIG. 36, still another nerve stimulating device 2K is shown wherein the same or similar reference numbers refer to the same or similar structure. Nerve stimulating elements 6K are positioned on a main body 4K having an exterior surface 8K having a shape similar to a truncated four-sided pyramid and all characteristics of this shape described herein are incorporated here. The device 2K includes an insert 120 which may be a separate device that is attached to the main body 4K by the user. Alternatively, the insert 120 may be integrated into the device 2K without departing from the scope of the invention.

The insert 120 has conductive elements 122 positioned over the nerve stimulating element 6K which may be pliable to conform to tissue and thereby enhance electrical conduction. The plurality of conductive elements 122 are coupled to and separated by non-conductive elements 124 which may also be pliable. The electrically conductive element 122 may be a gel, such as a hydrogel, or a porous material 126 having a flowable material, such as saline, contained in the pores of the porous material 126. To this end, the term electrically conductive shall include porous materials that are not electrically conductive but can conduct electricity when the pores are filled with an electrically conductive material. The non-conductive element 124 may also be a thin layer of material such as a closed cell structure made of a non-conductive material. Alternatively, the non-conductive element 125 may simply be a pliable layer 127 of non-conductive material such as silicone. The pliable nature of the layer 127 may help to conform to tissue to create a barrier to electrical conduction between adjacent nerve stimulating elements 6K. The insert may include a main body 129 that may simply be an elastic band 131 at a radially outer (larger end) of a central opening 133. The band 131 may be coupled to one or both of the non-conductive elements 125 and/or conductive elements 122.

Figure 41:
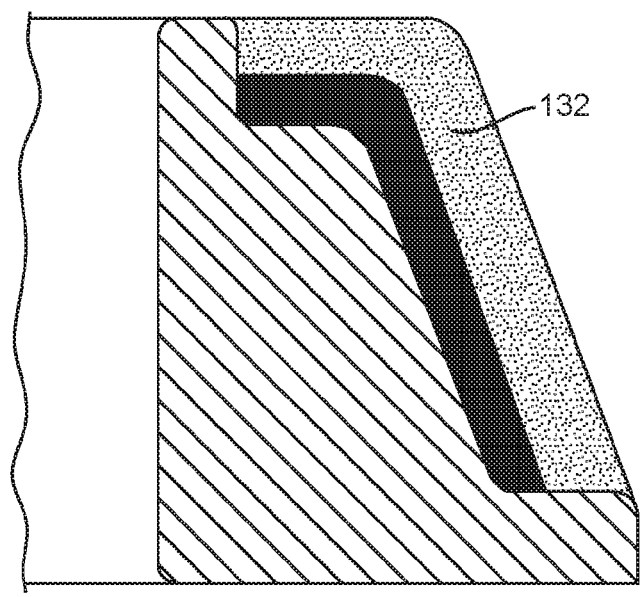
FIG. 41 is a partial cross-sectional simplified view showing the nerve stimulating element positioned in the recess with the conductive material positioned over the nerve stimulating element.
Figure 42:
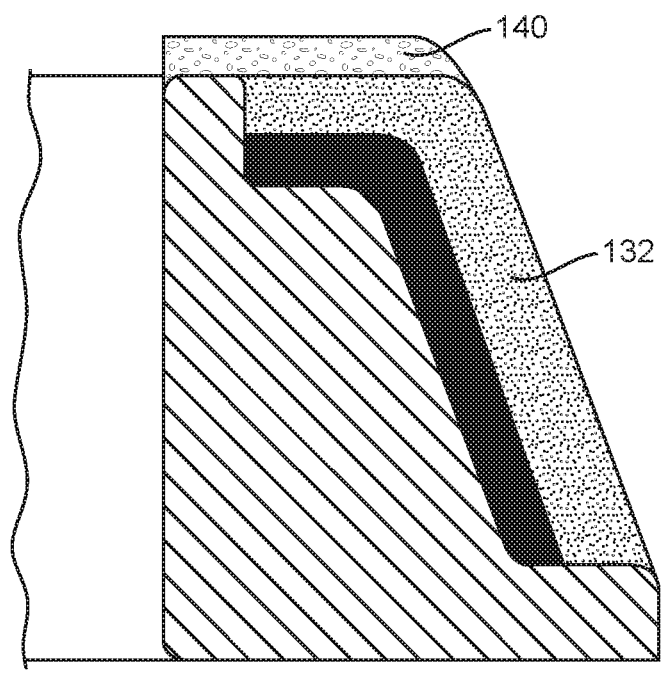
FIG. 42 shows a dissolvable portion forming part of the main body of the device of FIG. 37.
Figure 43:
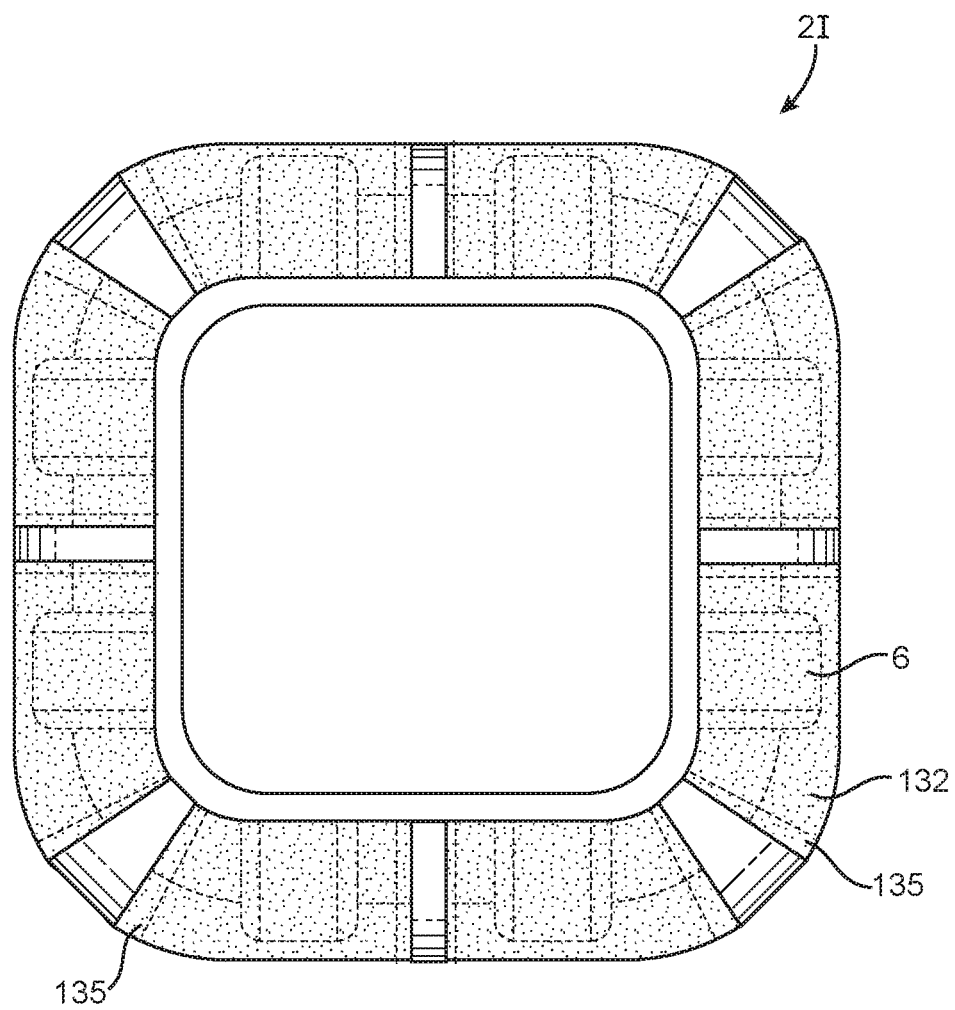
FIG. 43 is a plan view of the device with the dissolvable portion removed.
Figure 44:
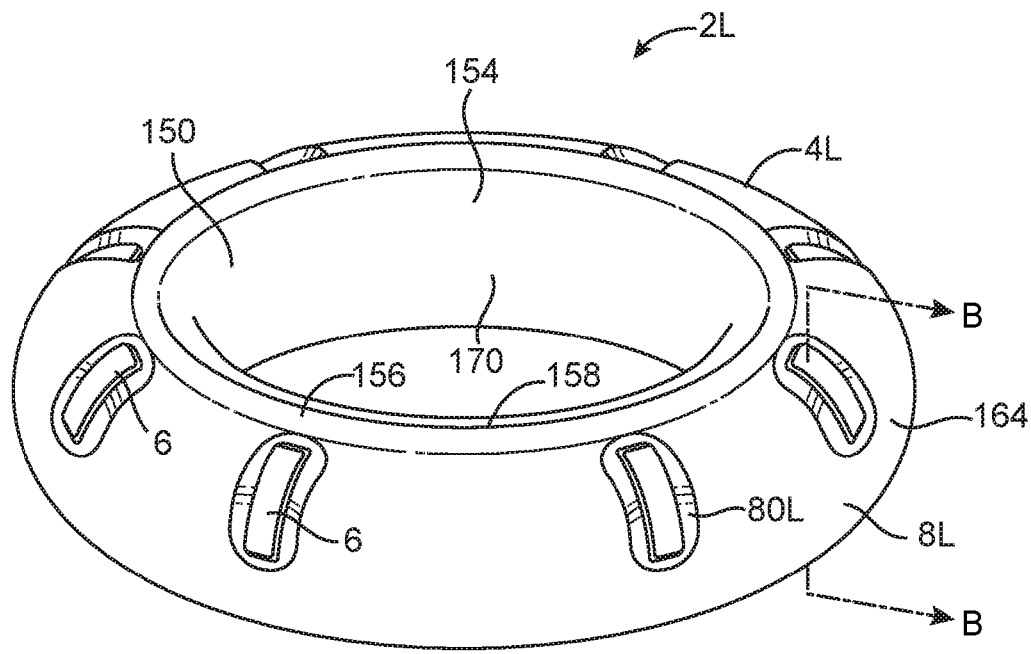
FIG. 44 shows a device having a torus-shaped exterior surface with a wall positioned near the central opening.
Figure 45:
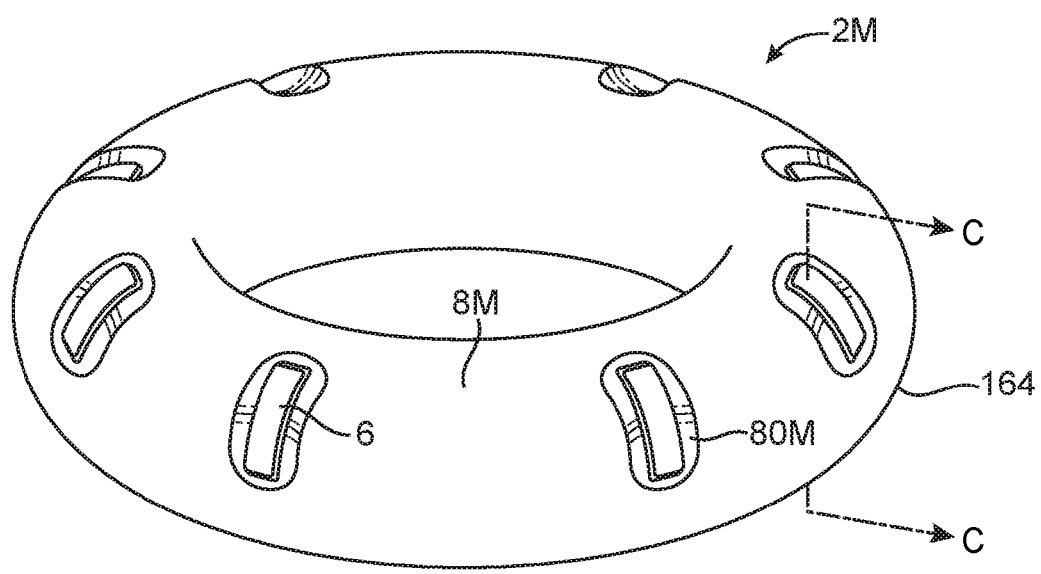
FIG. 45 shows a device having a torus-shaped exterior surface with the nerve stimulating element positioned in a recess.
Figure 46:
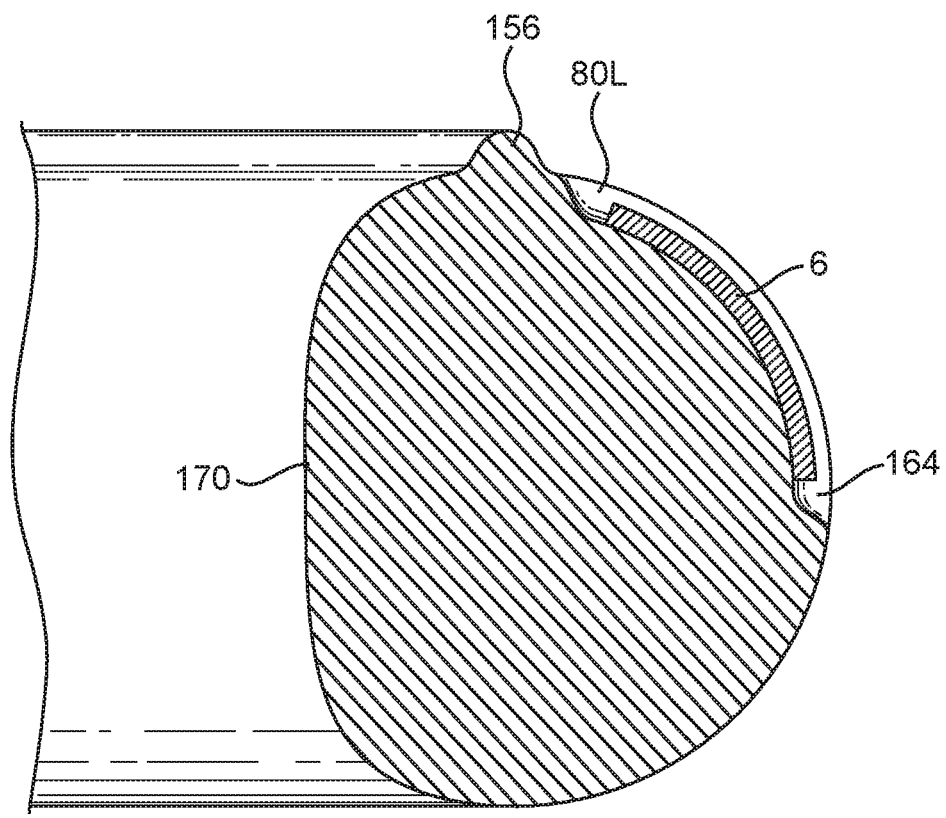
FIG. 46 is a simplified cross-sectional view showing the nerve stimulating element of FIG. 44 contained in a recess.
Figure 47:
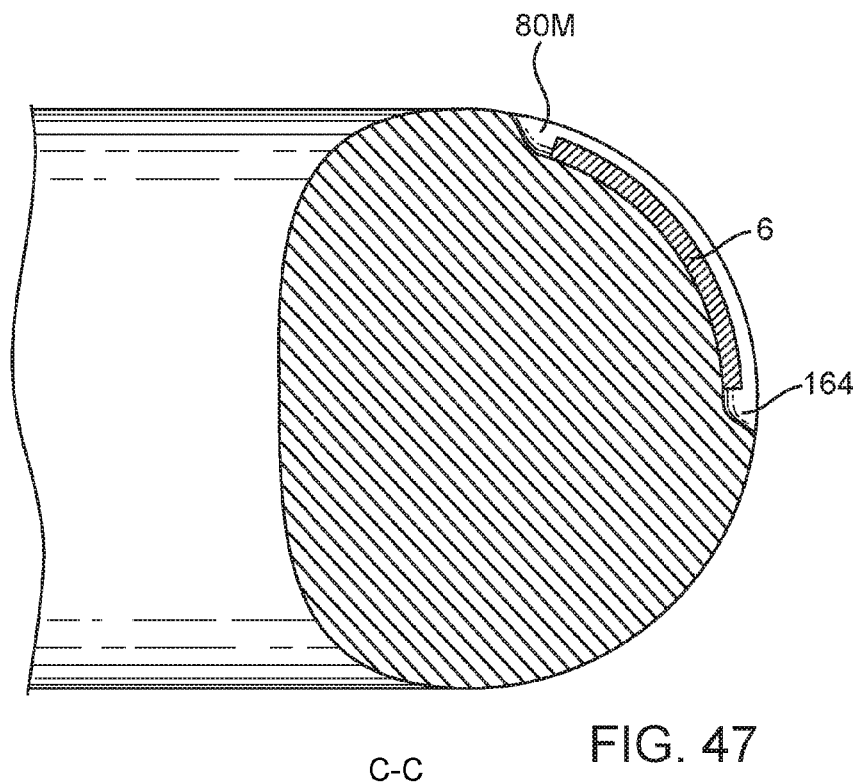
FIG. 47 is a simplified cross-sectional view showing the nerve stimulating element of FIG. 45 contained in a recess.
Figure 48:
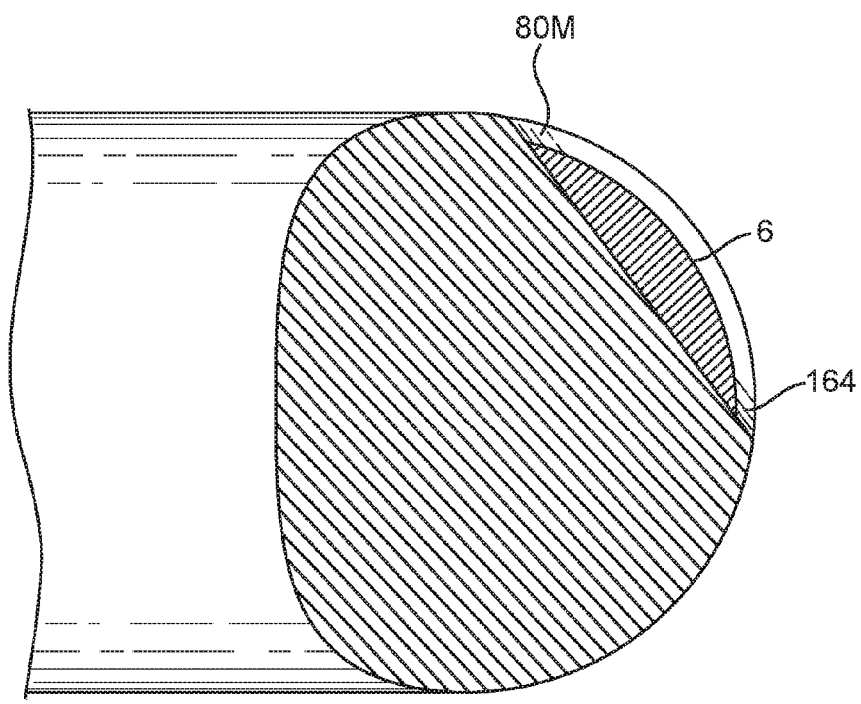
FIG. 48 is an alternative cross-sectional view for FIG. 47.
Figure 49:
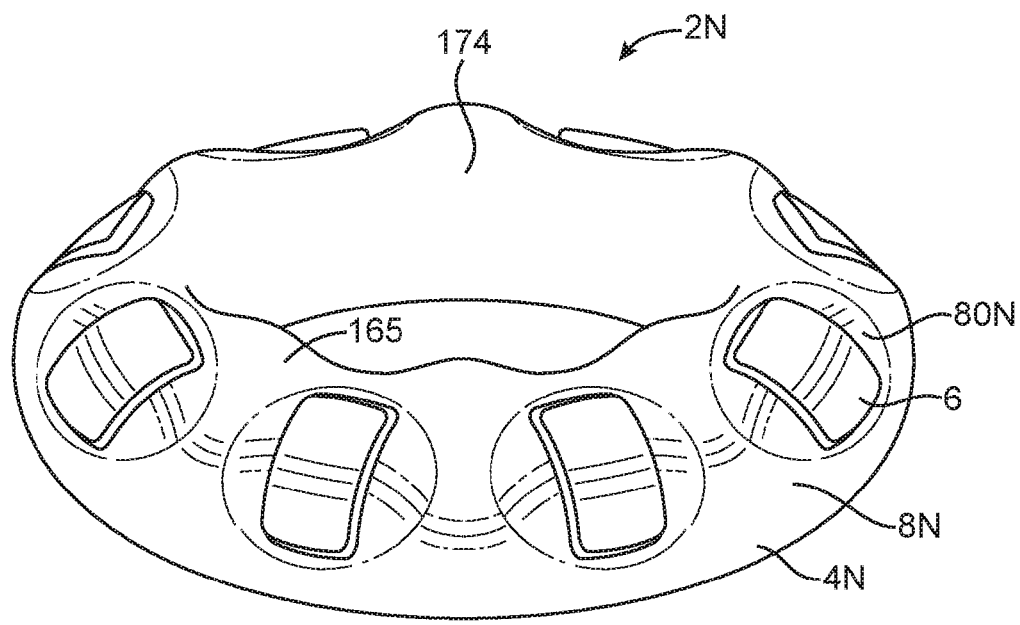
FIG. 49 shows still another device for stimulating nerves having a torus shaped exterior surface with recesses forming a scalloped appearance.
Figure 50:
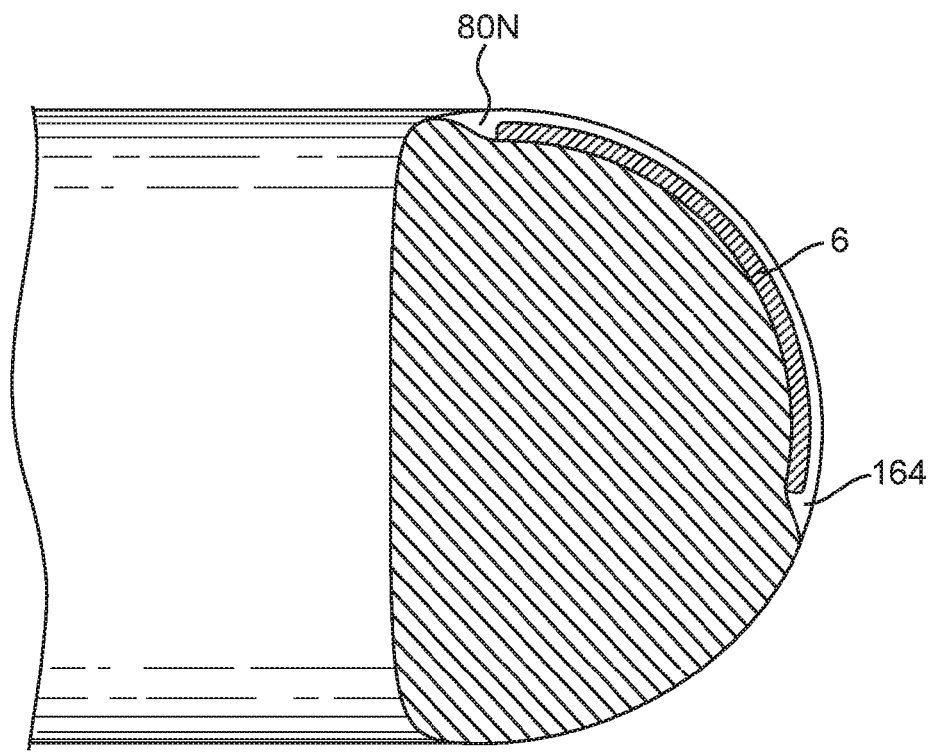
FIG. 50 shows a simplified cross-sectional view showing the nerve stimulating element of FIG. 44 contained in a recess.

Referring to FIGS. 37-43, another device 2I is shown for use with an insert 130 wherein the same or similar reference numbers refer to the same or similar structure. The device 2I is substantially the same as the device 2K and all aspects of device 2K are incorporated here. The insert 130 has conductive elements 132 mounted to a main body 137, which may form a closed loop 145, at spaced apart locations. The conductive elements 132 may be any of those described herein including the pliable structures described above. The main body 137 includes non-conductive elements 135, such as a thin layer, positioned between the conductive elements so that the conductive elements 132 are coupled to and separated by non-conductive elements 135. The main body 137 may include a dissolvable portion 142 that dissolves within the body under normal conditions (vagina in this application). Referring to FIGS. 41 and 43, the dissolvable portion 142 may include the non-conductive elements 135 thereby leaving only the electrically conductive elements 132.

Referring to FIGS. 44-51, a device 2L, a device 2M and a device 2N are shown having bodies 4L, 4M, 4N with an exterior surface 8L, 8M, 8N that each form a torus. As used herein "torus" shall apply to shapes that are torus-like or generally torus-shaped. The devices 2L, 2M and 2N also form a closed ring 150 like other embodiments described above. The nerve stimulating elements 6 are positioned in recesses 80L, 80M, 80N as shown in the cross-sectional view of FIGS. 46, 47, 48 and 50. The main body 2L of the device 2L has a central opening 154. The main body 4L has a non-conductive wall 156 which may be a closed loop 158 adjacent the opening 154 and positioned between the nerve stimulating element 6 and a radially inner side 170 of the torus. The recesses 80L, 80M, 80N and nerve stimulating elements 6 are positioned predominantly on a radially outer side 164 of the torus. The device 2N includes recesses 80N which form a scalloped shaped wall 165 extending around the central opening 174 and positioned between the nerve stimulating element 6N and the radially inner side 170 of the torus. As shown in the various cross-sectional views, the exterior surface 8L, 8M, 8N at the radially inner side 170 of the torus may be somewhat flattened.

Figure 51:
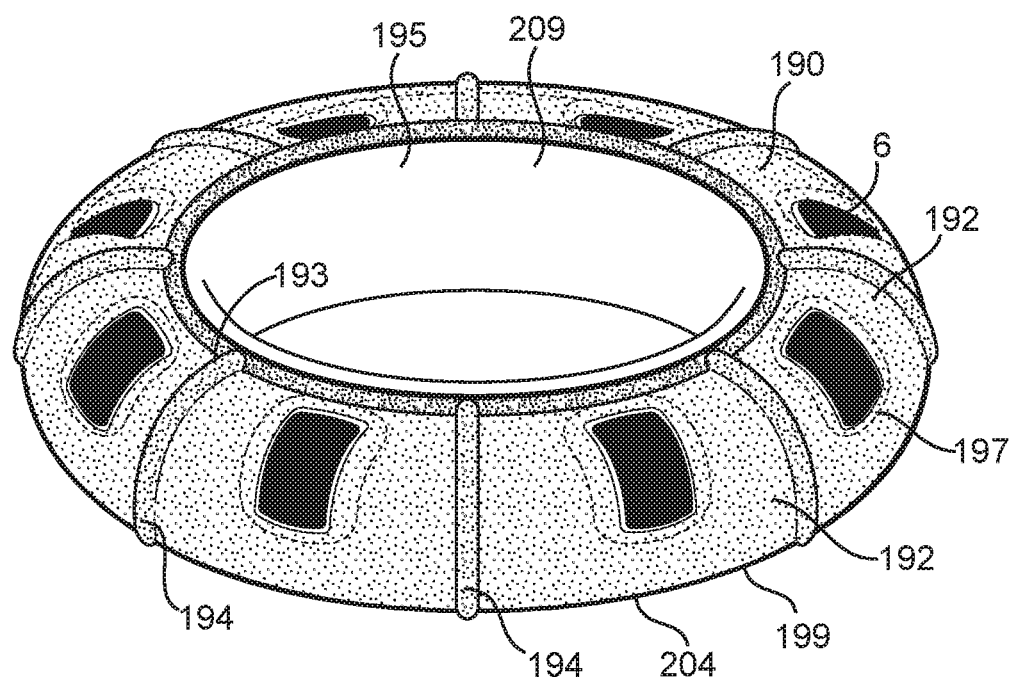
FIG. 51 shows an insert that may coupled to any of the devices described herein.

Referring to FIG. 51, another insert 190 is shown which may be applied to any of the devices 2L, 2M, and 2N. The insert 190 may be integrated with the devices 2L, 2M, 2N or may be a separate, disposable device that is applied by the user. The insert 190 has conductive elements 192 separated by non-conductive elements 194 similar to the other inserts described above and all discussion above is equally applicable and incorporated here concerning the conductive element 192 and non-conductive element 194. The non-conductive element 192 may, for example, be a layer 193 of non-conductive material such as silicone. The insert 190 may include a body 204 which may simply be an elastic band 199 extending around one end to secure the insert 190 onto the devices 2L, 2M, 2N. The body 190 may form a closed loop 195 (as broadly described herein) with the elastic band 199 circumscribing the closed loop 195 around the central opening 209. The non-conductive element 194 may also form a raised wall 211 relative to the conductive element 192. The raised wall 211 may also be a thin layer of silicone. The insert 190 may include openings 197 through which the nerve stimulating element 6 is exposed. The openings 197 are positioned to expose the nerve stimulating elements 6 with at least one nerve stimulating element 6 in each opening 197. The term "insert" as used herein is used to describe a disposable device used with a reusable part although the insert may, in fact, not be "inserted" into any part of the device and, as shown, may in fact simply surround the other reusable device. Of course, at times the insert is introduced into another object (such as a recess) yet such interaction is not required. The term "system" as used herein may refer to an integrated, single piece device and does not imply or require multiple parts (other than those integrated into a system). Of course, the system may still be provided in separate parts, such as separate controller, control system or battery external to the vagina, without departing from the invention as well since a system may still include separate components coupled together wirelessly or with wires.

Figure 52:
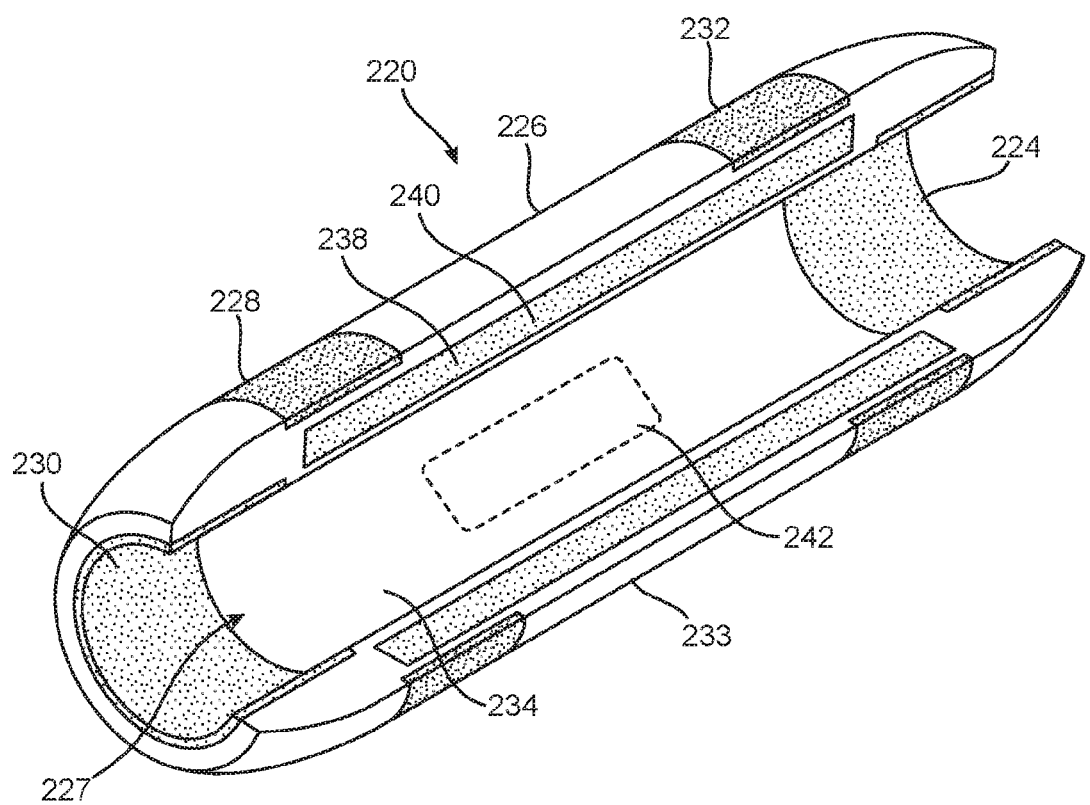
FIG. 52 shows an implant.

Referring now to FIG. 52, an implant 220 in accordance with the present invention is shown. The implant 220 is used to stimulate nerves independently, in conjunction with other implants 220 or in conjunction with any of the devices 2, 2A-2N. The implant 220 is surgically placed and secured adjacent to the uterosacral ligament so that a first nerve stimulating element 224 (coupled to an implant body 226) is positioned in contact with the uterosacral ligament. The implant body 226 may be secured directly to the uterosacral ligament with the uterosacral ligament positioned in a throughhole 227 extending through the implant body 226. Alternatively, the implant 220 may be secured to another structure with the nerve stimulating element 224 positioned in contact with the uterosacral ligament. A second nerve stimulating element 228 may be positioned on an outer surface 233 of the implant body 226 so that it is in contact with the peritoneum after placement. A third nerve stimulating element 230 (also coupled to the implant body 226) may also be provided and positioned in contact with the uterosacral ligament at an opposite end of the throughhole 227 from the first nerve stimulating element 224. A fourth nerve stimulating element 232 may also be in contact with the peritoneum and spaced apart from the second nerve stimulating element 228. For the purpose of defining the invention and in particular the claims, the numerical nomenclature associated with the nerve stimulating elements and other structures, such as the "fifth nerve stimulating element" shall not carry numerical significance in that reciting the "fifth nerve stimulating element" does not necessitate four additional nerve stimulating elements and the numerical significance shall not be taken into account. Thus, the "fifth nerve stimulating element" may, in accordance with the claims, be the second recited nerve stimulating element with only two recited. Use of the "fifth nerve stimulating element" may, in fact, be the first (and possibly only) nerve stimulating element for a particular implant but is used since another implant recites (at times in subsequent dependent claims) the second, third and fourth nerve stimulating elements. All aspects of the nerve stimulating elements described herein are applicable to the nerve stimulating elements of the implant 220 and all features and characteristics are incorporated here for the nerve stimulating elements of the implant 220.

The uterosacral ligament passes through a slot 234 when introduced into the throughhole 227. The implant body 226 is movable from an open position, which permits the uterosacral ligament to enter the throughhole 227 to a locked position which prevents the uterosacral ligament from moving out of the throughhole 227. The locked position may also be provided in any suitable manner such as with a separate structure including as a suture, clasp, cinch, clamp, or a sliding door or gate over the slot 234 without departing from the scope of the invention.

Figure 54:
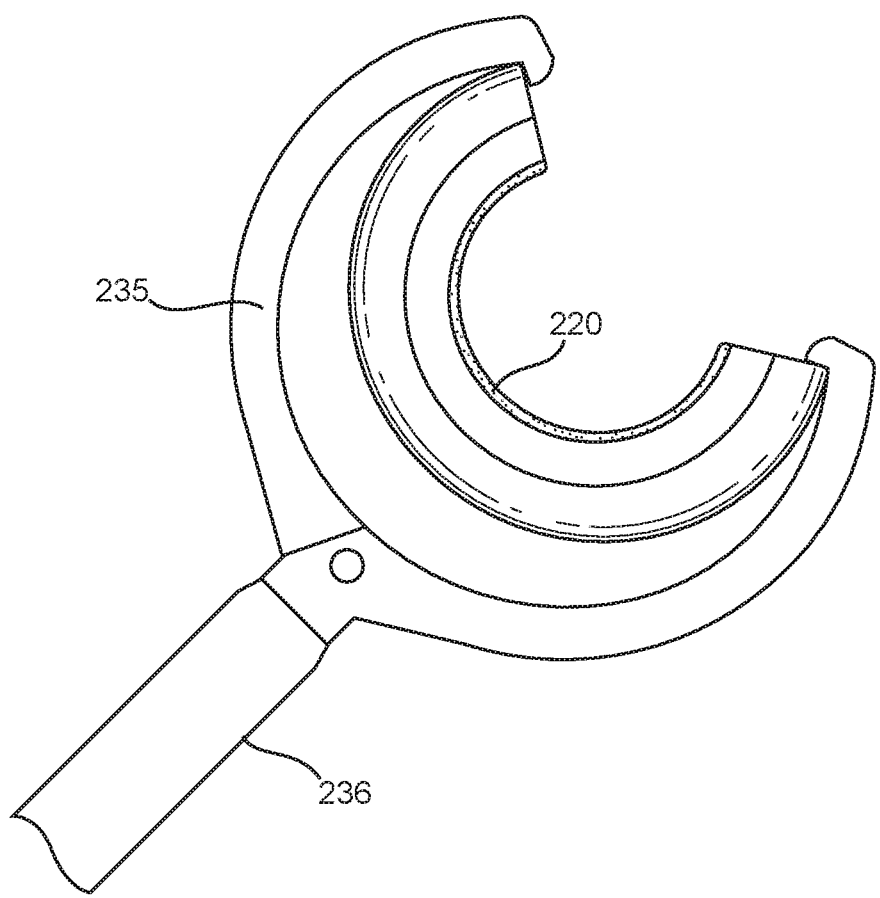
FIG. 54 shows a delivery tool holding the implant with the implant in an open position for introduction of the uterosacral ligament.

Referring to FIG. 54, the implant body 226 may also be held in the open position with a delivery tool 236. The delivery tool 236 has a movable jaw 235 so that the delivery tool 236 can hold the implant 220 in the open position of FIG. 54 and release the implant 220 when desired. The implant body 226 is introduced into the abdomen in the open position and released when the uterosacral ligament is positioned in the throughhole 227. The implant 220 may naturally move to the locked position with the delivery tool 236 holding the implant 220 in the open position. Alternatively, the implant body 226 may be naturally biased to the open position and closed by the delivery tool 236 to clamp and secure the implant 220 to the ligament. Of course, the clamping force must be applied in a controlled manner to prevent excessive pressure on the uterosacral ligament while still adequately securing the implant 220. The implant 220 may include other securing features, such as one or more eyelets to receive suture passed through the uterosacral ligament, without departing from the scope of the invention.

The implant 220 also includes a power source 238, such as a battery 240, coupled to the implant body 226. A control system 242 (positioned within the implant body 226) is coupled to the power source 238 and to the nerve stimulating elements in a conventional manner. The battery 240 may be rechargeable (not shown) without departing from the invention and may be charged with a charging device positioned in the vagina in the same position as the device 2 as described in greater detail below.

As mentioned above, the first and third nerve stimulating elements 224, 230 are in contact with the uterosacral ligament which itself is physically connected through various tissue paths to the target plexuses as described herein. Thus, the uterosacral ligament is used to transmit nerve stimuli to the target plexuses and nerves and the anatomic position of the uterosacral ligaments relative to the target areas is advantageous as described above. The nerve stimulating elements on the implant 220 may also be useful for stimulating other nerve plexuses such as the superior hypogastric plexus (SHP) which would be difficult to stimulate using the device 2. The nerve stimulating elements on the implant 220 may also be suitable for delivering stimulation to the middle rectal plexus to treat fecal urge, rectal conditions, and/or incontinence.

Figure 53:
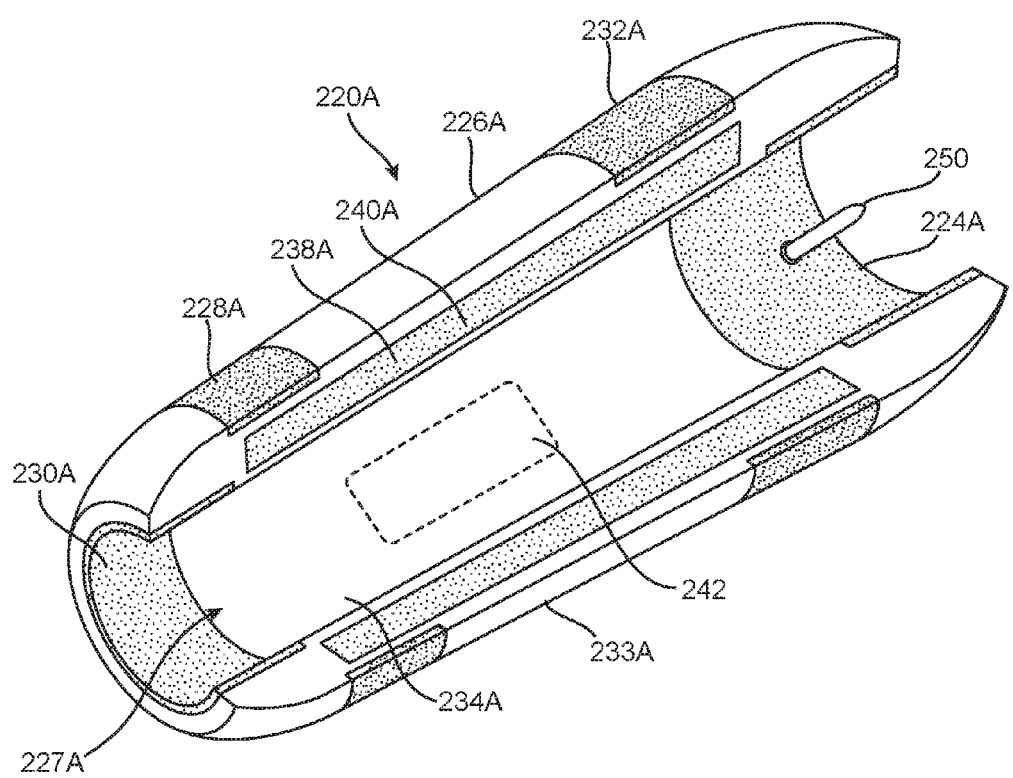
FIG. 53 shows another implant.

Referring to FIG. 53, another implant 220A is shown wherein the same or similar reference numbers refer to the same or similar structure. The implant has a throughhole 227A, a control system 242, and first, second, third and fourth nerve stimulating elements 224A, 228A, 230A, 232A. The throughhole 227A is tapered to accommodate a tapered geometry of the ligament. When sizing the implant 220A, the size may be taken at two positions so that a tapered geometry may also be considered when selecting the appropriate size of implant 220A. The first nerve stimulating element 224A has a piercing element 250 configured to extend into and pierce the uterosacral ligament when securing the first nerve stimulating element 224 to the uterosacral ligament. To this end, the piercing element 250, may be a barb, needle, spike or pin extending into the throughhole 227. When the implant 220A is placed around the ligament the piercing element 250 automatically extends into and pierces the ligament. The piercing element 250 may help prevent migration (slipping) of the implant 220A along the ligament and also may improve stimulation by improving contact between the first nerve stimulating element 224A and the uterosacral ligament and associated autonomic nerves. The piercing element 250 is preferably made of a conductive material so that the piercing element 250 forms part of the first nerve stimulating element 224. It is understood that whenever implant 220 is described that implant 220A may be substituted with all features and methods incorporated.

Figure 70:
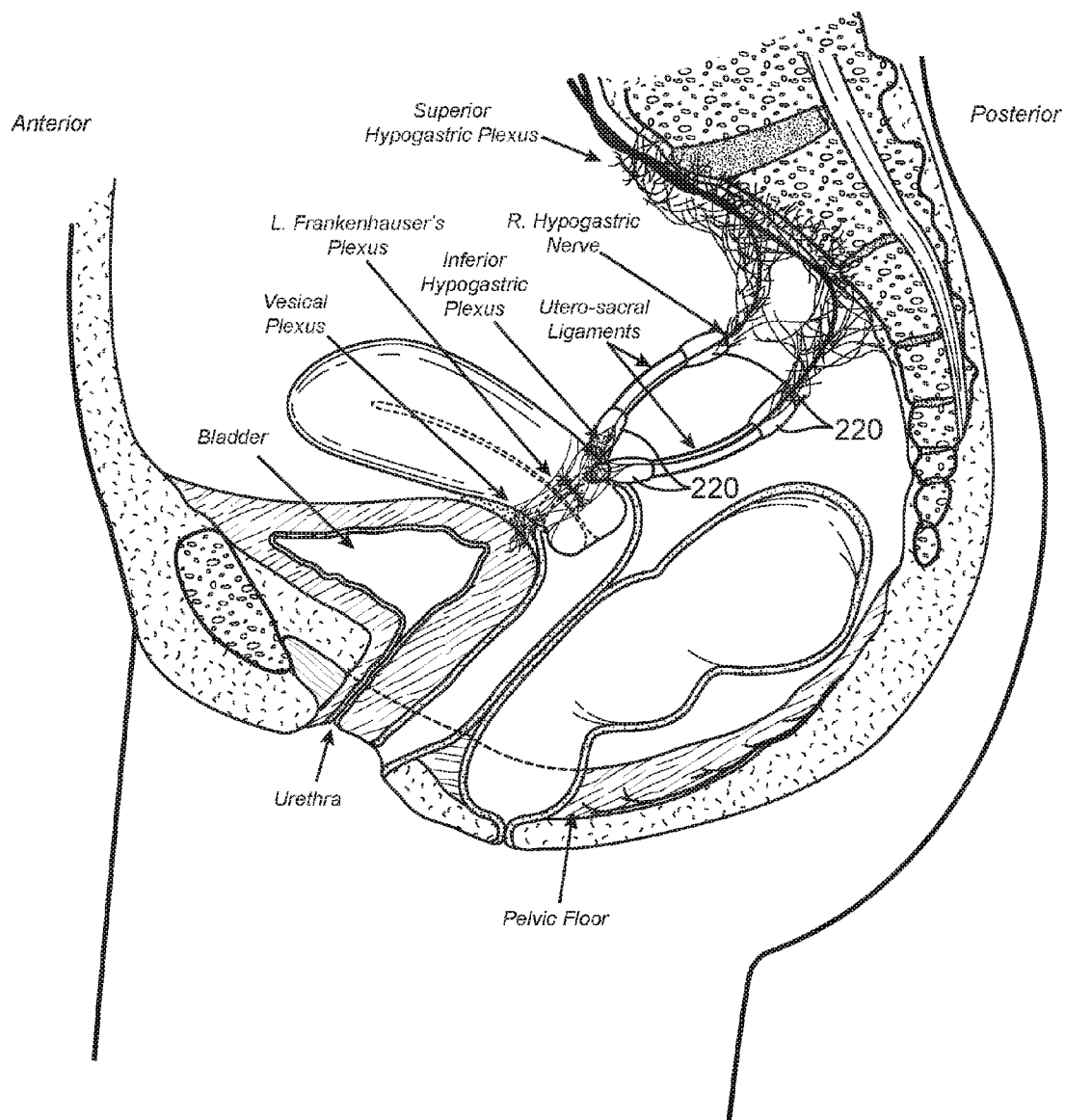
FIG. 70 shows two implants secured to each uterosacral ligament.

The implant 220 may also be small enough so that two implants 220 can be positioned adjacent (and even secured) to the same uterosacral ligament. If the implants 220 are separated with one positioned anteriorly on the uterosacral ligament and the other positioned posteriorly (as shown in FIG. 70) it is possible to primarily stimulate the IHP with one implant and the SHP with the other.

Figure 69:
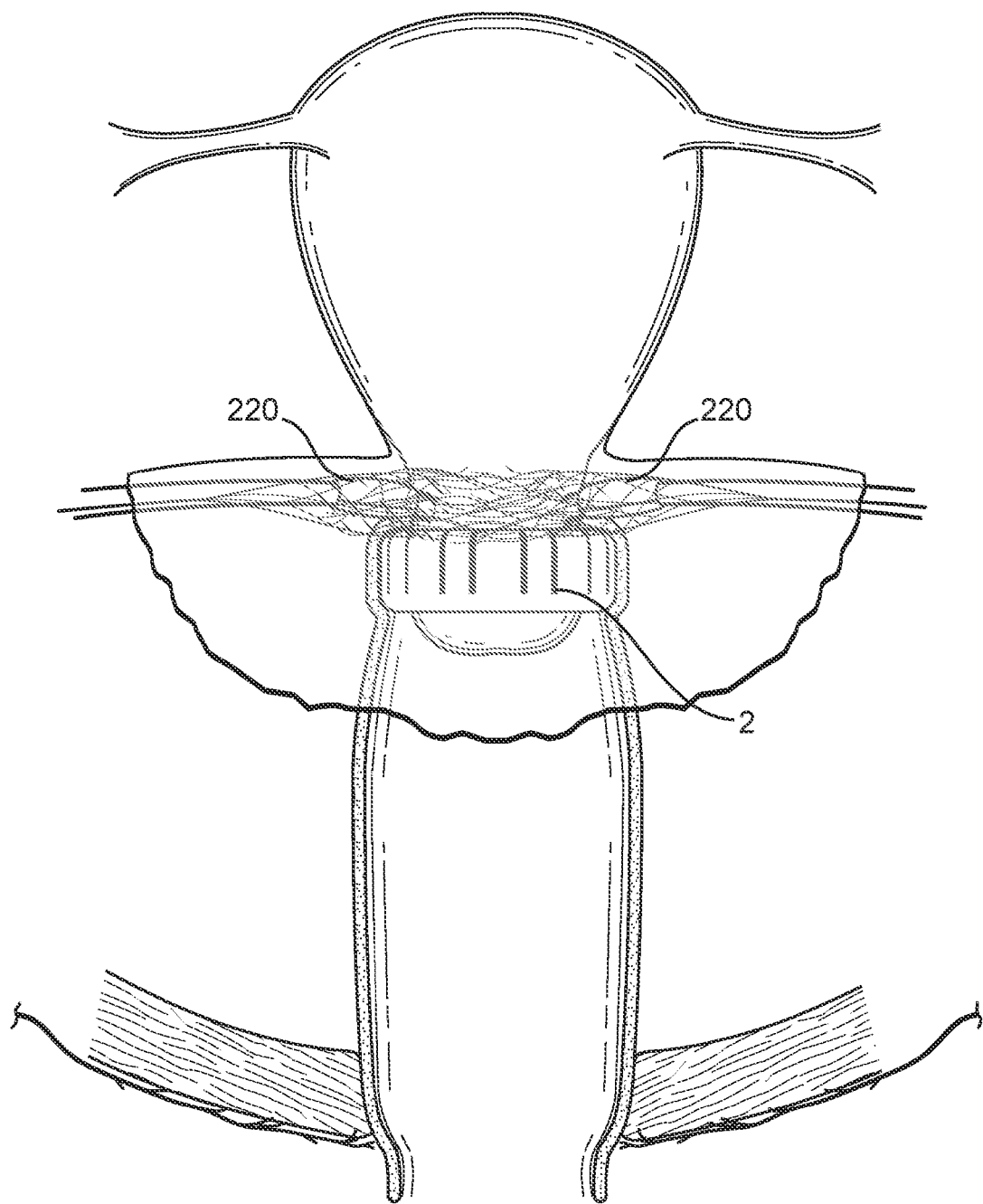
FIG. 69 shows the device positioned with the vaginal fornices and two implants.

The implant 220 may be used by itself, together with additional implants 220, 220A or in conjunction with any of the devices 2, 2A-2N positioned in the vagina described herein and shown in FIG. 69. It is understood that when device 2 is described for the combination with the implant 220 that any of the other devices 2A-2N may be used as a substitute and those features and methods of use, including all claims, are expressly incorporated. Furthermore, all aspects of the devices 2, 2A-2N positioned in the vagina and described herein may be used with the implant 220 of the present invention for stimulating nerves and nerve plexuses and all aspects, uses and characteristics of the nerve stimulating elements and methods for devices 2, 2A-2N are specifically incorporated here for combining with the implant 220 of the present invention.

The implant 220 and the devices 2, 2A-2N may work together to stimulate nerves to modulate the signal of the autonomic plexuses surrounding the cervix and uppermost aspect of the vagina, namely, the inferior hypogastric plexus (IHP), Frankenhauser's plexus (L and R) and the vesical plexuses (L and R). In this manner, the stimulation may alter systemic sympathetic discharge throughout the sympathetic chain. In a specific aspect, the device 2 may have two nerve stimulating elements 6. The two nerve stimulating elements 6 on the device 2 and the nerve stimulating element(s) on the implant 220 together stimulate at least three nerve plexuses from the following list; SHP, IHP, L vesical, R vesical, L Frankenhauser's, and R Frankenhauser's. For example, the implant 220 may stimulate the IHP (or the SHP) while the device 2 has at least one of the nerve stimulating elements 6 stimulating a side of the Frankenhauser's plexus (L or R) and another nerve stimulating element 6 stimulating the other side of the Frankenhauser's plexus relative to the midline 83 (see FIG. 22). Alternatively, the nerve stimulating elements 6 may be positioned with one nerve stimulating element 6 positioned on a side of the vesical plexus and another nerve stimulating element 6 positioned on the other side of the vesical plexus relative to the midline 83. The "other side" of a plexus as used herein shall mean any position on the opposing side of the midline to the other nerve stimulating element and, thus, the nerve stimulating elements positioned on "the other side" do not have to be 180 degrees from one another.

The device 2 may also communicate with the implant 220 to coordinate stimulation. For example, various therapies may require simultaneous stimulation while others require independent stimulation. The device 2 and the implant 220 may communicate by simply transmitting and receiving electrical signals through tissue using the nerve stimulating element 6 of the device 2 and the nerve stimulating element of the implant 220. For the purpose of the present invention, "communication" shall require either transmission or receipt of signals or information but does not require both. The controller 24 of the device 2 may be used to communicate with the control system 18 of the device 2 to control, for example, a duration of stimulation and an intensity of stimulation. The controller 24 may also be configured to communicate stimulation instructions for the control system 242 of the implant 220 to the device 2 which then communicates the instructions to the implant 220. Of course, the controller 24 may be configured to communicate instructions directly to the control system of the implant 220 as well. For example, the controller 24 (and/or the implant 220) may generate radiofrequency signals to communicate with one another in a conventional manner.

More than one implant 220 may be delivered and secured to the same uterosacral ligament. Each implant 220 may include all features related to the implants of the present invention. When more than one implant 220 is used, the control systems 242 of the implants 220 may also communicate with one another to coordinate stimulation (such as simultaneous stimulation or independent stimulation). The implants 220 may communicate using electrical signals transmitted to and from the nerve stimulating elements and transmitted through tissue. Alternatively, the nerve stimulating elements (or a separate antenna, not shown) may be used to transmit and receive radiofrequency signals. Of course, any other suitable method of communication between the implants 220 is within the scope of the invention including a physical connection between the implants 220 (such as a filament or wire) although wireless communication is preferred.

Figure 55:
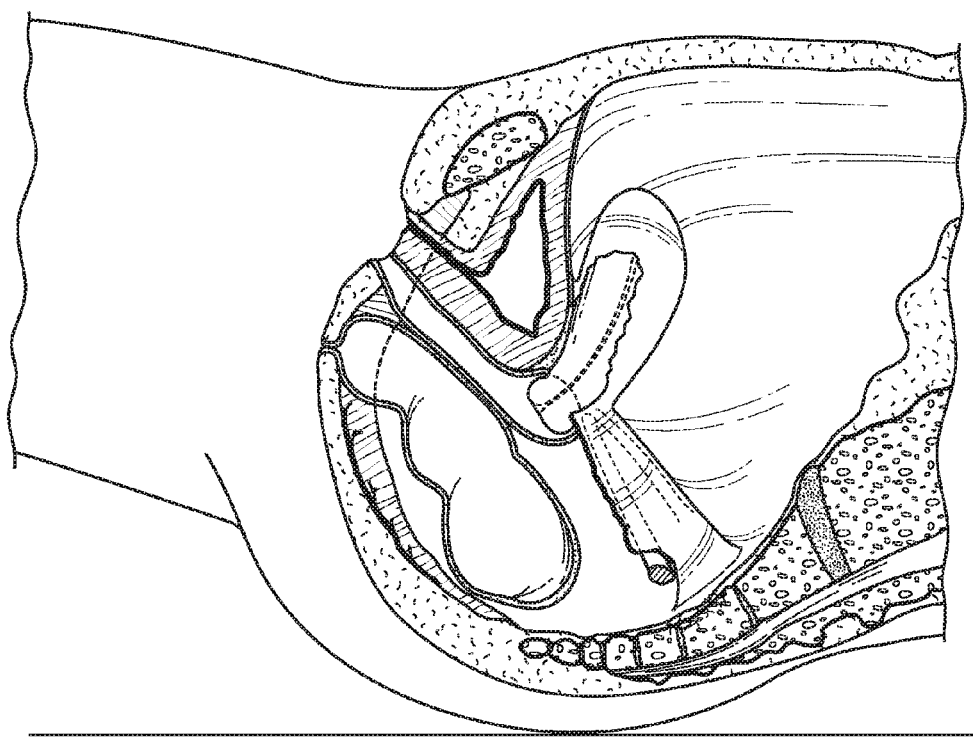
FIG. 55 shows a cross-sectional view of the abdomen and pelvic region.
Figure 56:
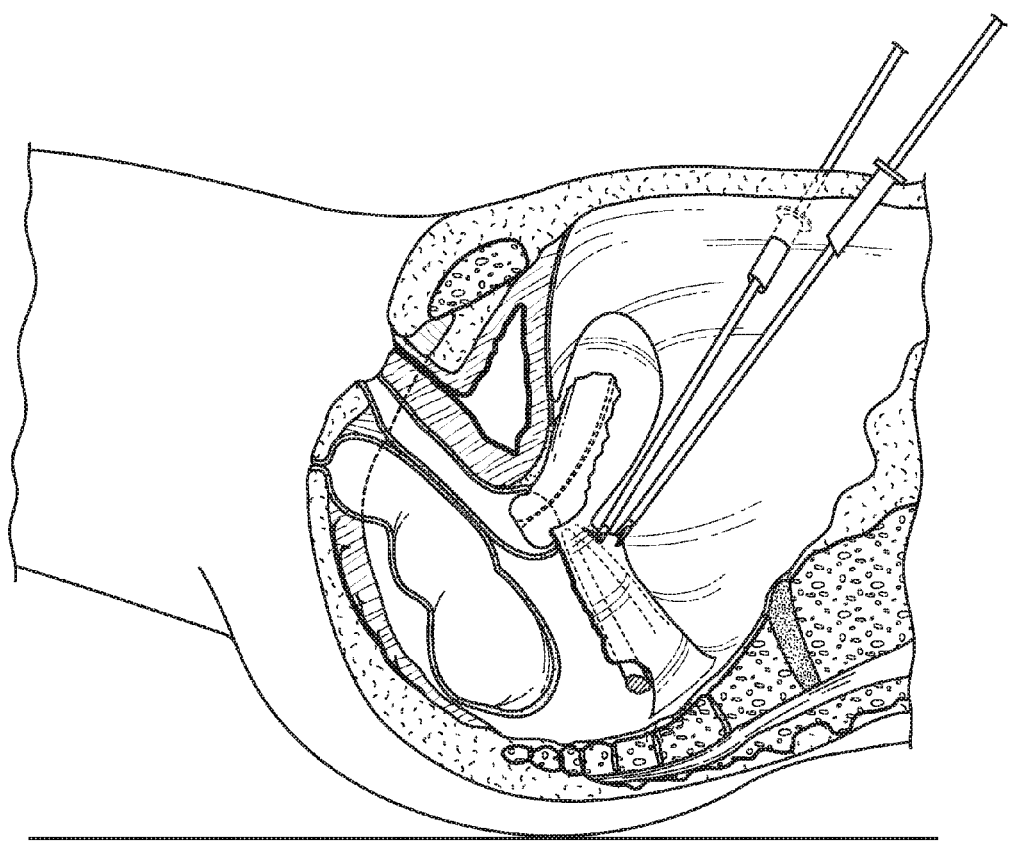
FIG. 56 shows a window formed in the peritoneum.
Figure 57:
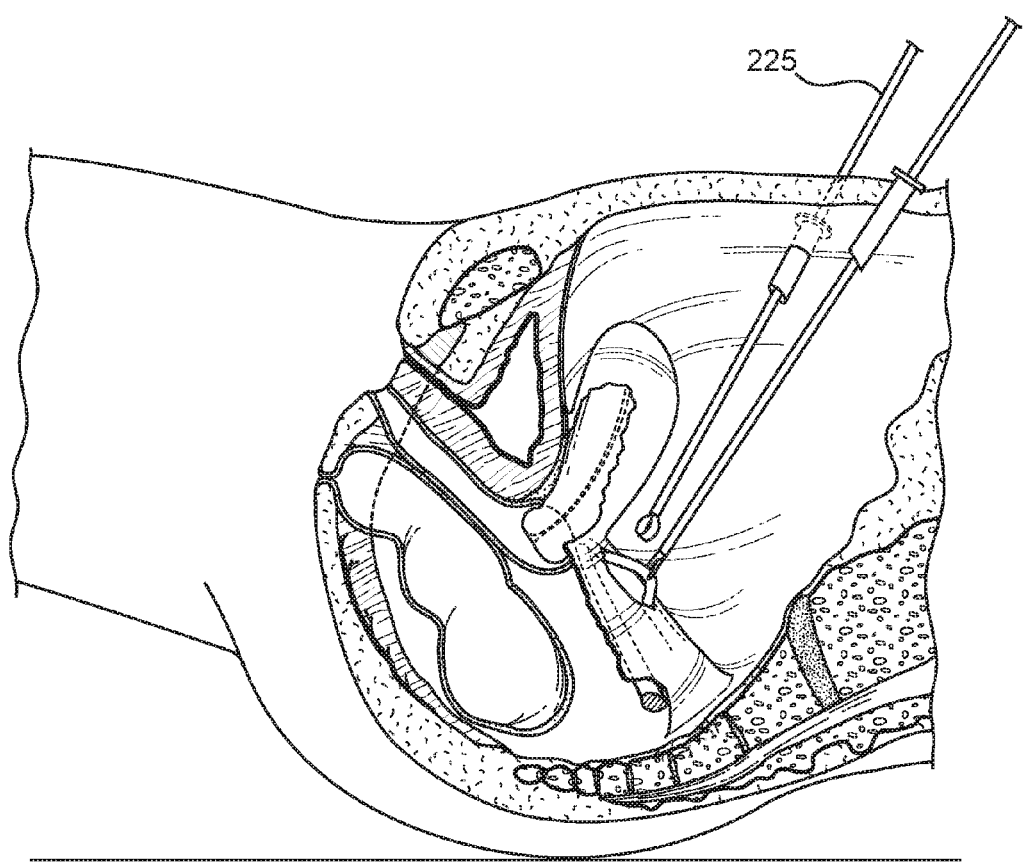
FIG. 57 shows a sizer introduced into the abdomen with the uterosacral ligament elevated.

Referring now to FIGS. 55-67, methods of delivering the implant 220 are now described. The implant 220 may be placed using traditional and/or robotic assisted laparoscopic techniques. A female patient is placed under general anesthesia and positioned for gynecologist laparoscopy in dorsal lithotomy and Trendelenberg position as shown in FIG. 55. Using laparoscopic and/or robotic technique with a camera and assisting port, the peritoneum over the intended portion of the uterosacral ligament is tented and an opening or window developed to gain retroperitoneal access as shown in FIG. 56. The ligament is then elevated with a grasper and mobilized medially as shown in FIG. 57.

Figure 58:
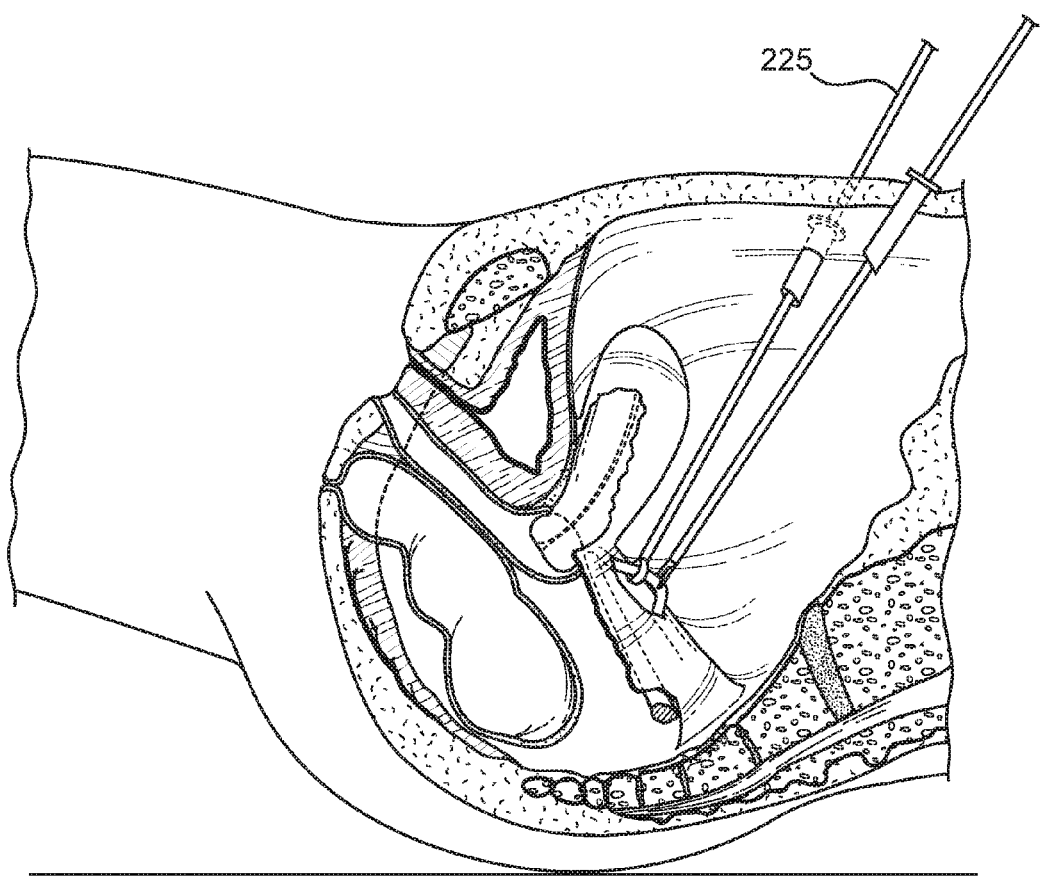
FIG. 58 shows the sizer extending around the ligament to size the ligament.
Figure 59:
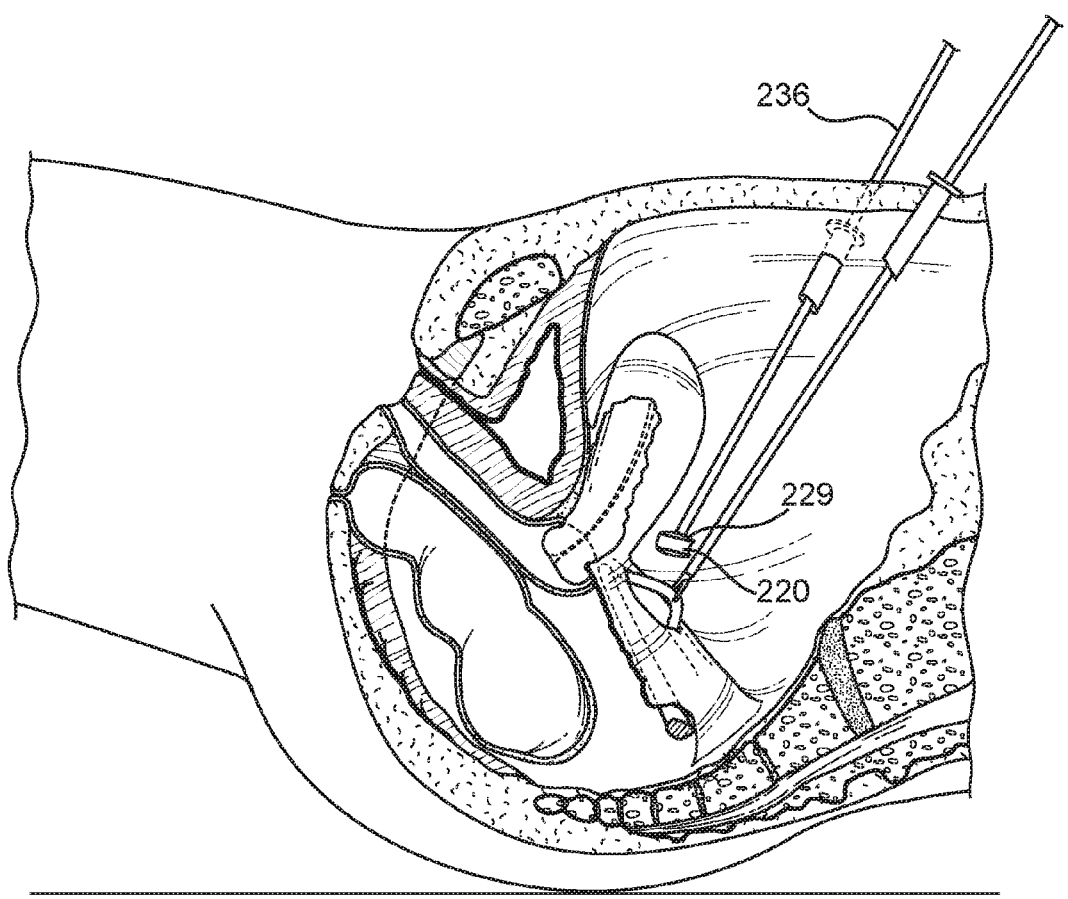
FIG. 59 shows the delivery tool with the implant approaching the ligament.
Figure 60:
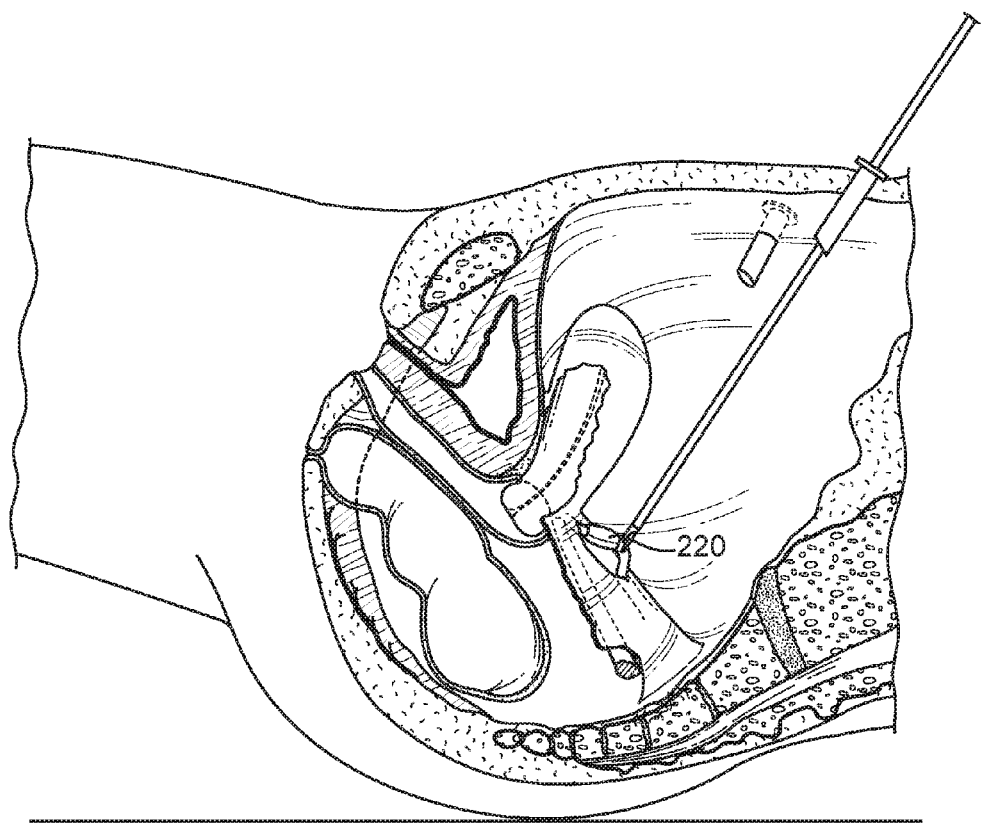
FIG. 60 shows the implant secured to the ligament.
Figure 61:
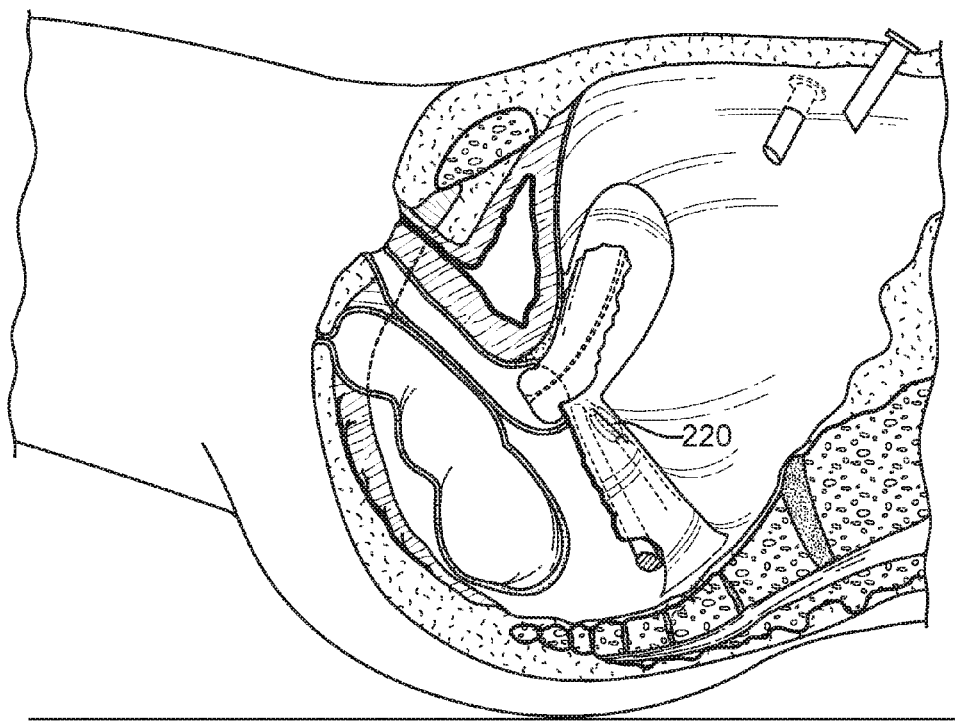
FIG. 61 shows the delivery tool removed and implant secured to the ligament.
Figure 62:
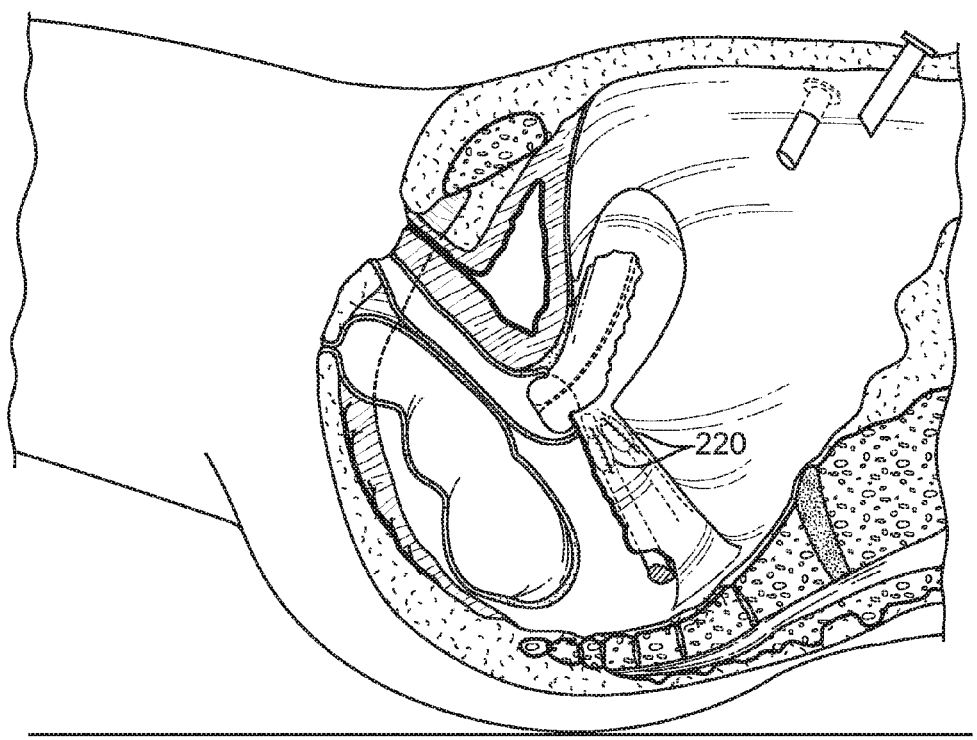
FIG. 62 shows another implant secured to the other uterosacral ligament.
Figure 63:
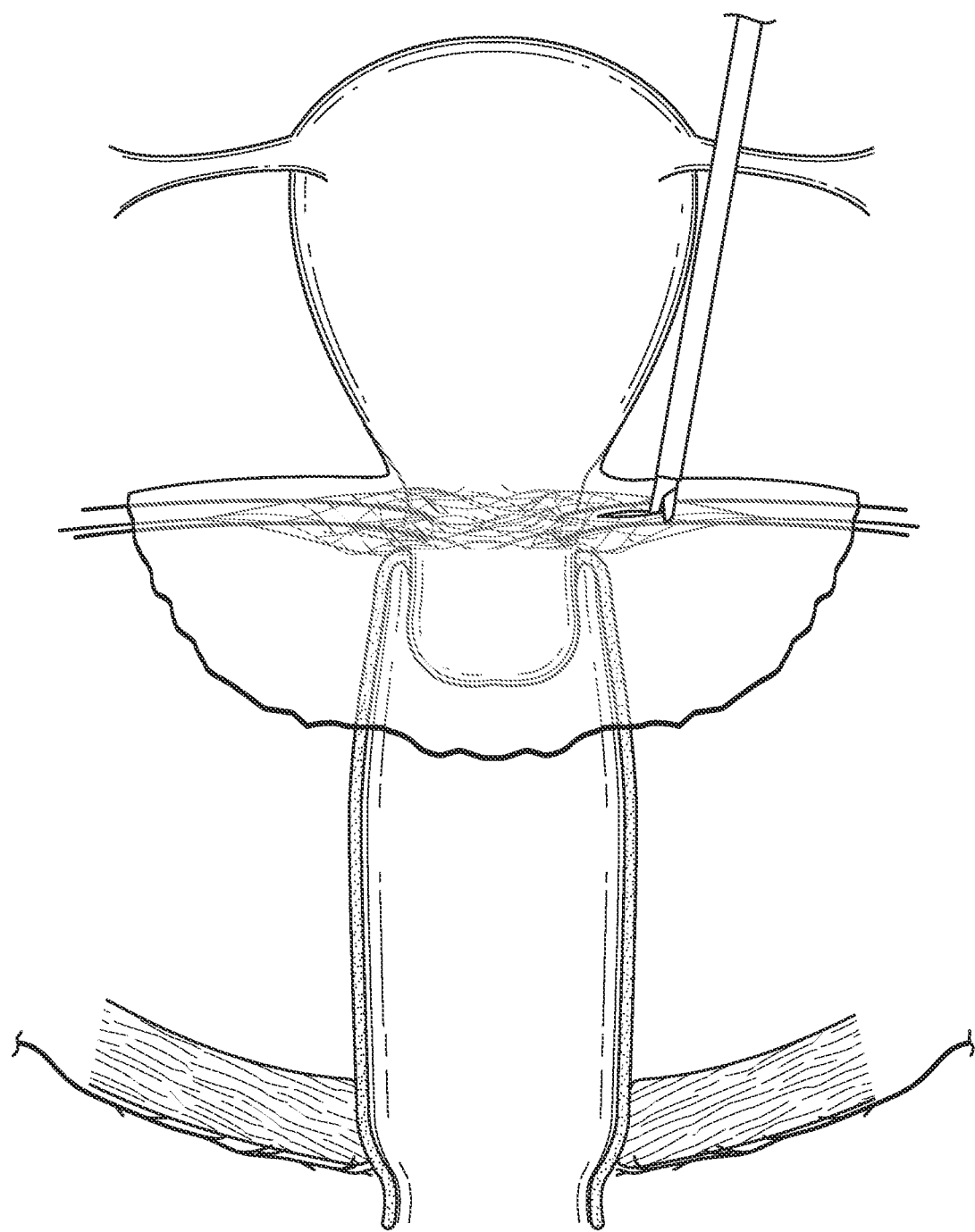
FIG. 63 shows another view of the window formed in the peritoneum.
Figure 64:
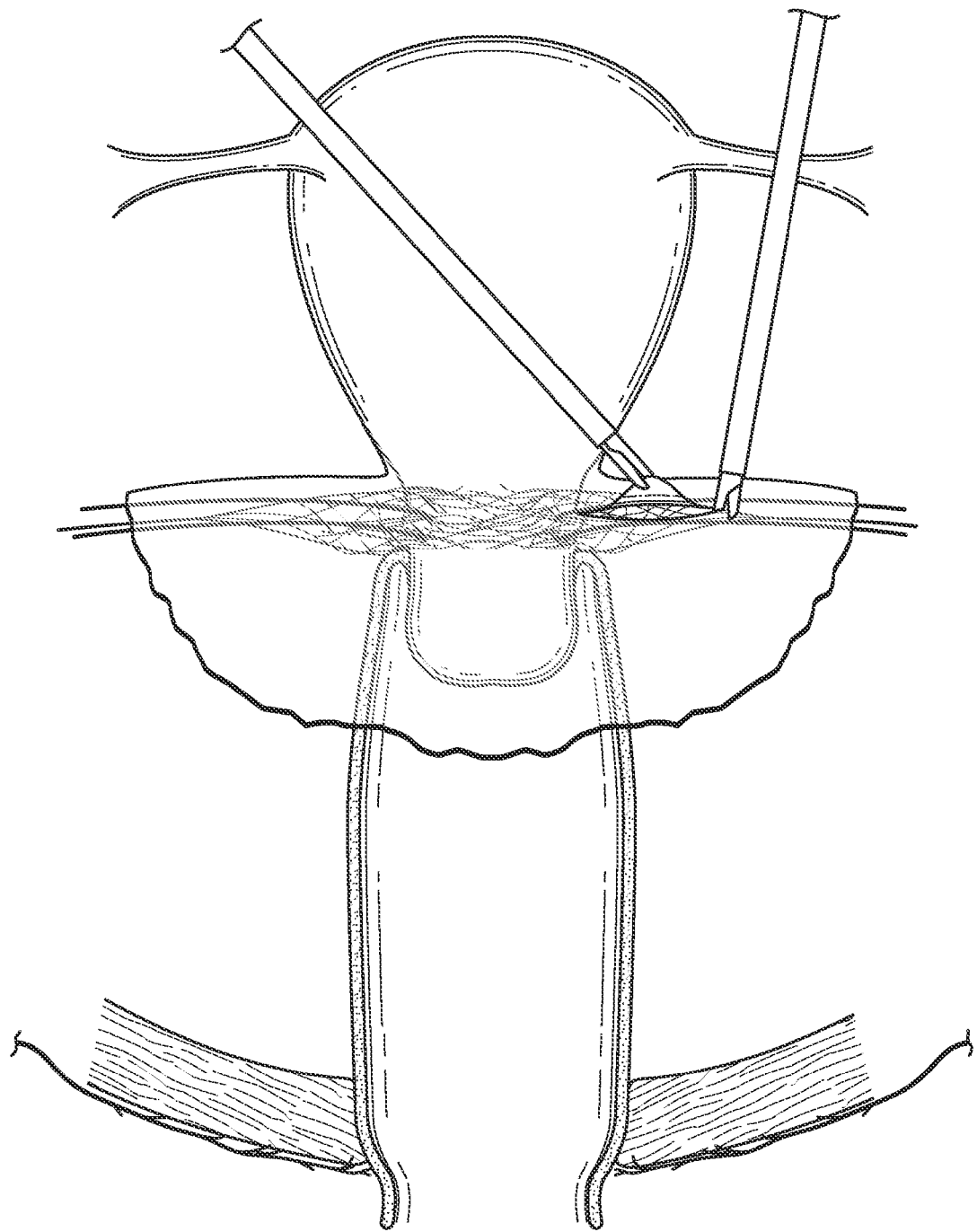
FIG. 64 is another view of showing the opening formed in the peritoneum.
Figure 65:
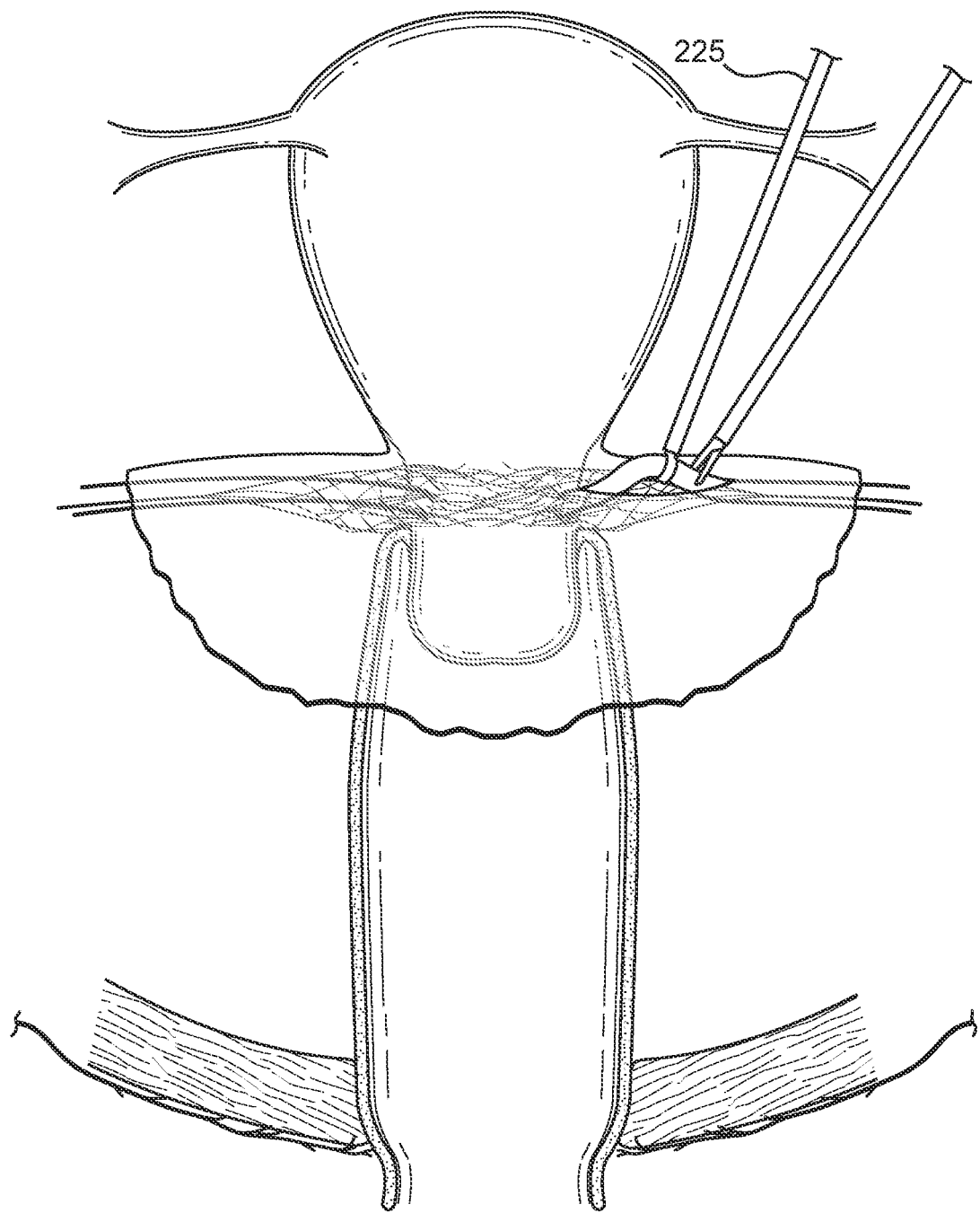
FIG. 65 is another view of the ligament being sized.
Figure 66:
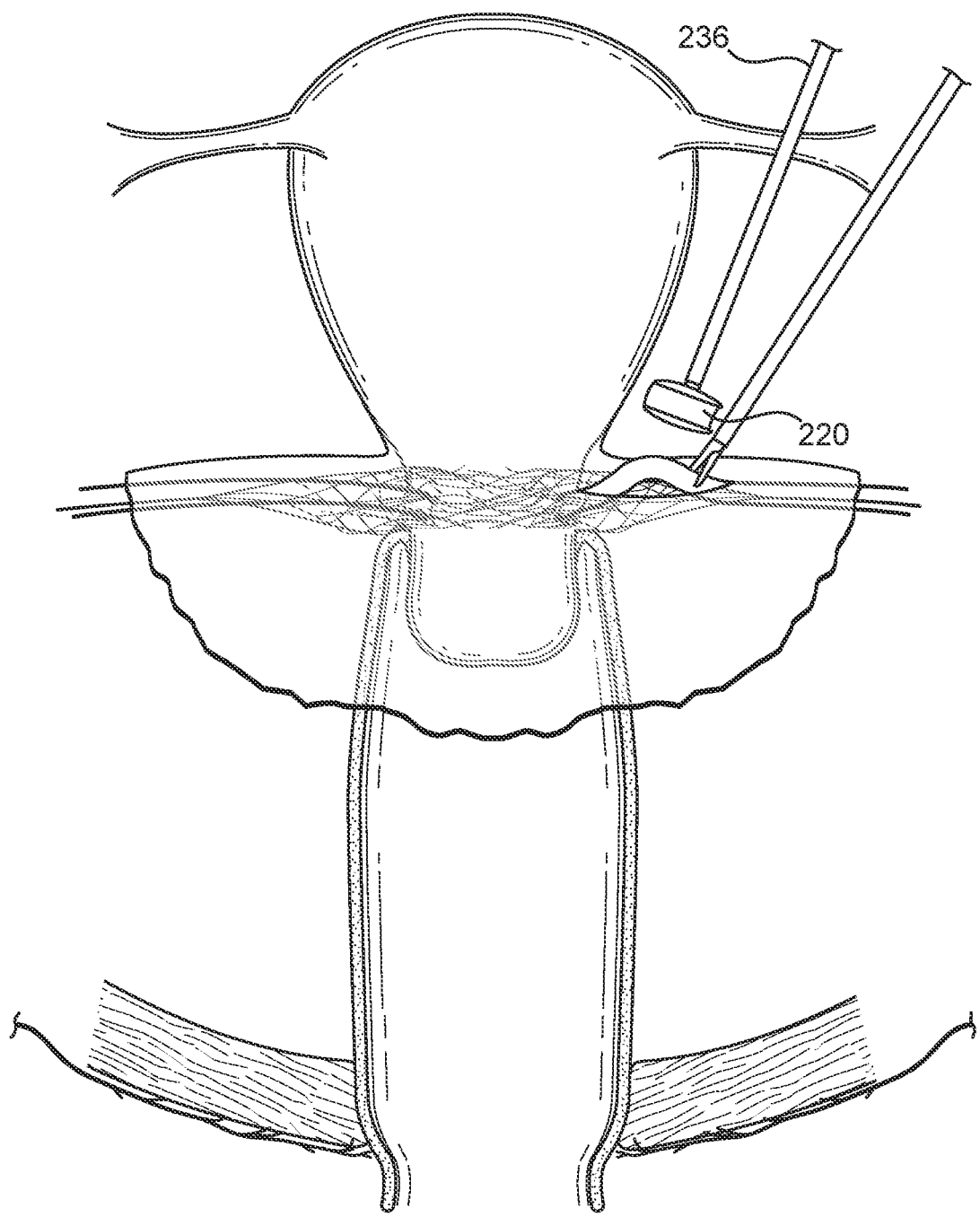
FIG. 66 is another view of the delivery tool introducing the implant into the abdomen.
Figure 67:
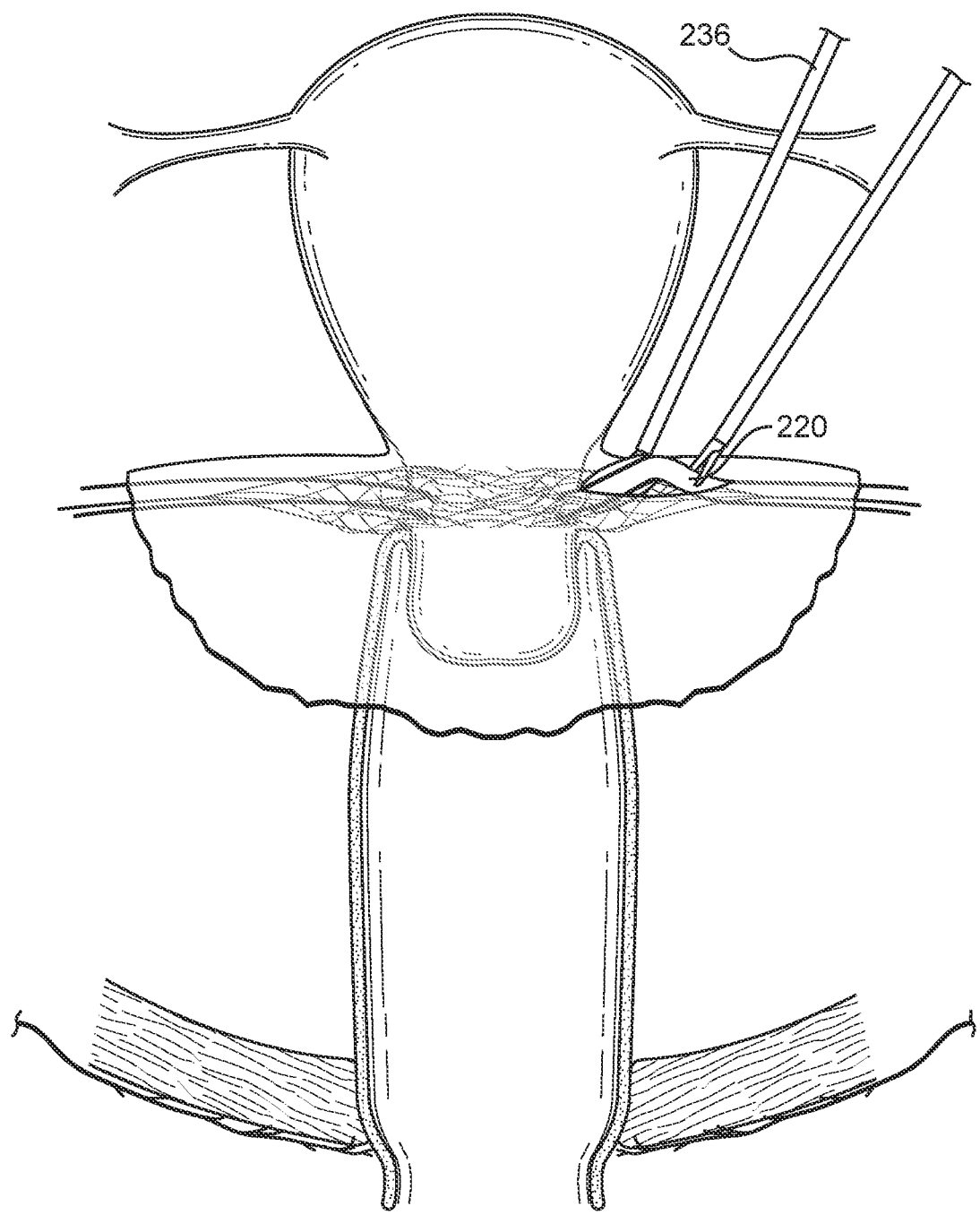
FIG. 67 shows the implant positioned around the ligament with the delivery tool.
Figure 68:
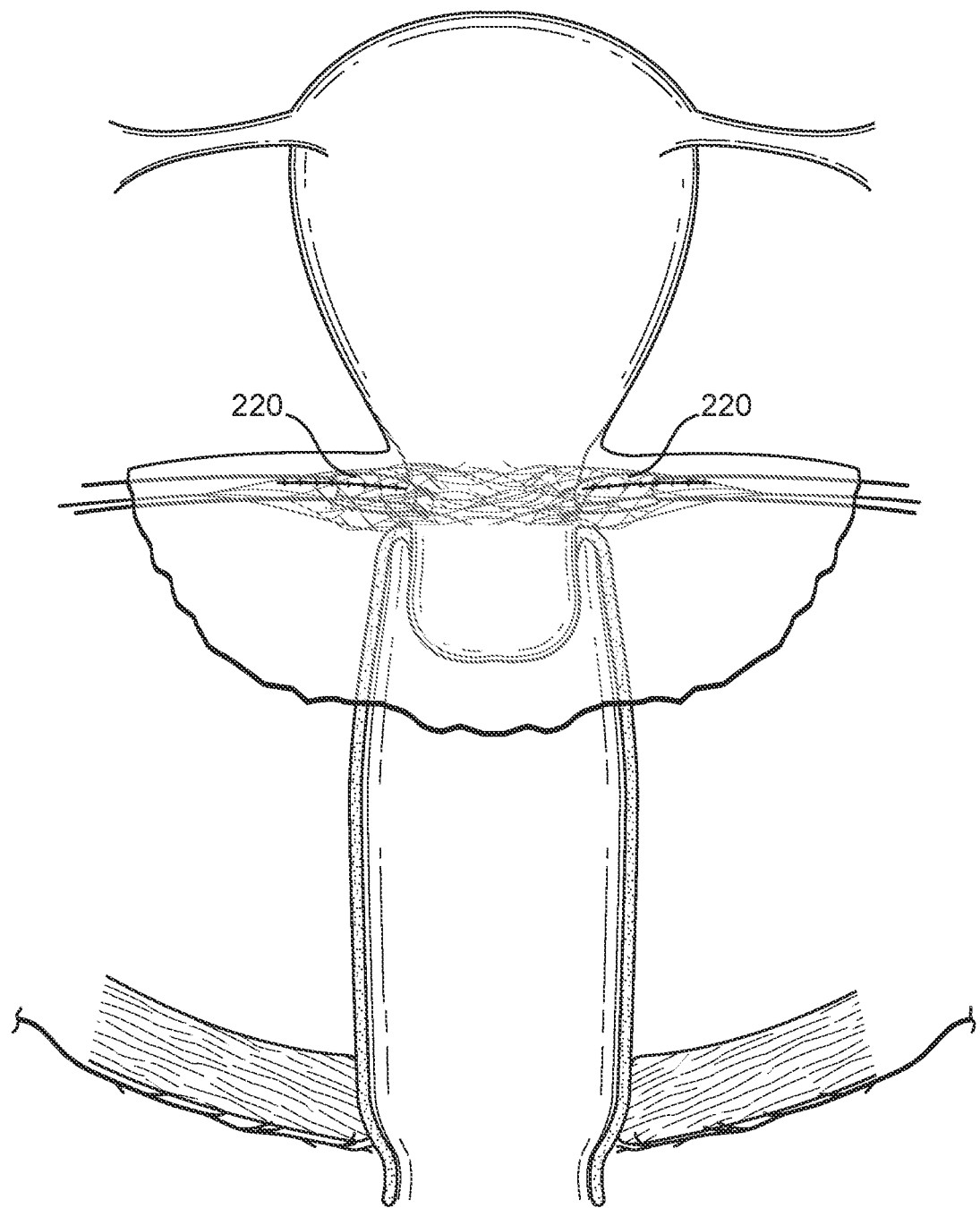
FIG. 68 shows an implant secured to each uterosacral ligament.

A ligament sizer 225 is introduced and the size of the ligament (circumference, diameter and/or thickness) is measured as shown in FIG. 58. When the implant 220A is used, at least two measurements are taken to provide an appropriately shaped tapered throughhole 227A. The sizer 225 may use any conventional method of determining thickness, for example, using magnetic, electromagnetic (not shown) objects to determine a spacing between the objects. The delivery tool 236, loaded with the implant 220 of proper size, is then introduced into the abdomen as shown in FIG. 59. The delivery tool 236 is then used to position the ligament within the throughhole 227 of the implant 220. The delivery tool 236 may include a pivoting holder 229 to facilitate positioning the implant 220 around the ligament. The surgeon will actuate the movable jaw 235 to simply release the implant 220 if the implant 220 is held open by the delivery tool 236. Alternatively, the delivery tool 236 may clamp the implant 220 to the ligament using the movable jaw 235. FIG. 60 shows the implant 220 secured to the ligament and FIG. 61 shows the peritoneum closed. FIG. 62 shows one implant secured to each uterosacral ligament. FIGS. 63-68 present an alternative view of the above-described procedure for placing the implant 220.

The implant 220 may be further secured to the ligament with permanent, monofilament sutures (not shown). Either end of the exposed longitudinal edges of the implant 220 may also include an arrow-like barb (not shown), attached to a fixed length of suture that is projected via an internal mechanism into the receiving opening on the opposing side of the throughhole 227. The arrow-like barb may be relatively large so that it becomes trapped and contained within the implant 220. The proximal and distal sutures may be delivered simultaneously with a fixed suture length. A properly fitted implant 220 will demonstrate two approximately 2-3 mm, exposed sutures on the medial surface. One or more suture(s) may be passed through the ligament to further prevent the implant 220 from traveling or slipping along the ligament. The implant 220 is then retroperitonealized surgically with absorbable suture. The profile of the implant 220 and the suture features are designed to prevent bowel adherence, in the case that the retroperitonealized implants become intraperitoneal.

Figure 71:
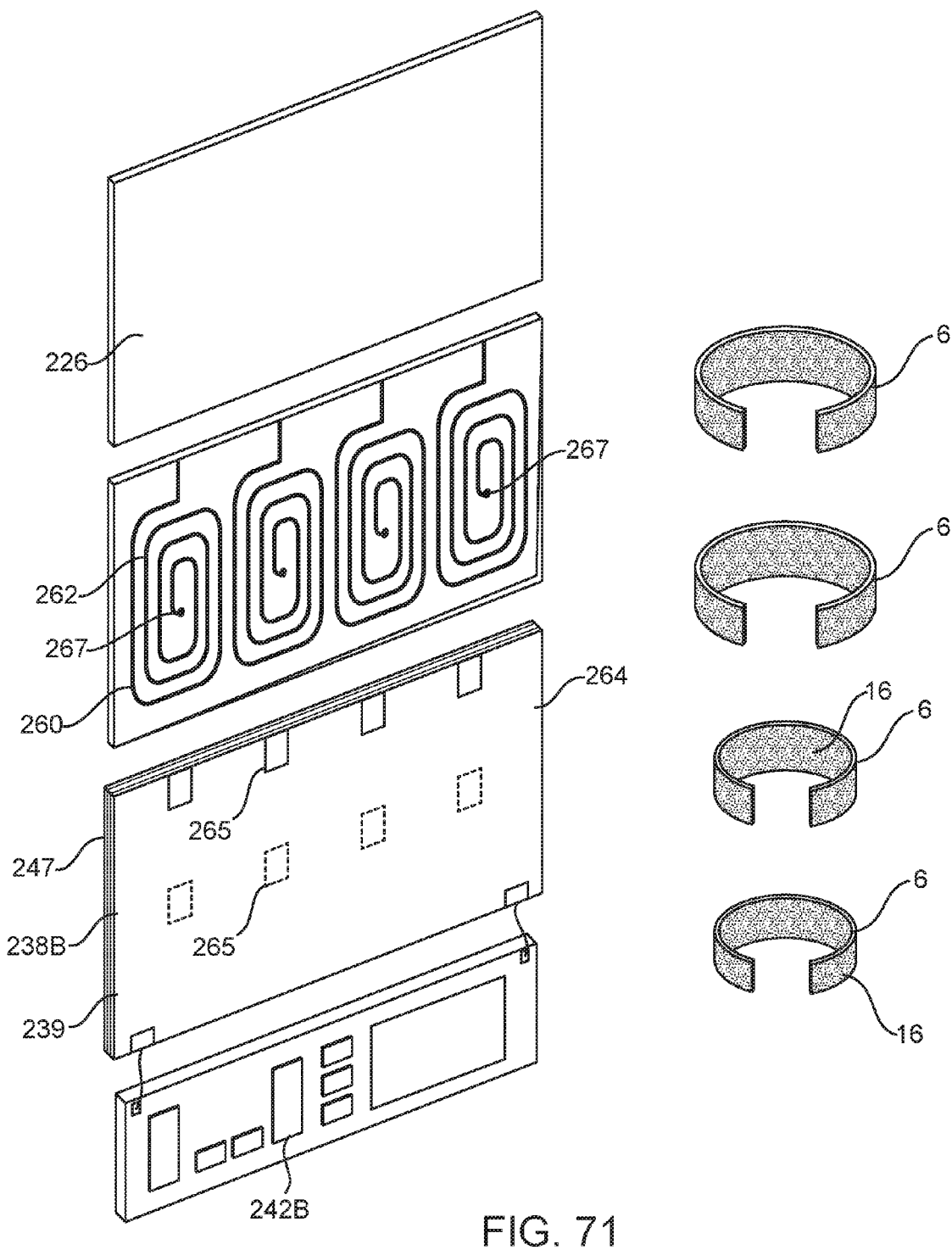
FIG. 71 shows an exploded view of another implant.
Figure 72:
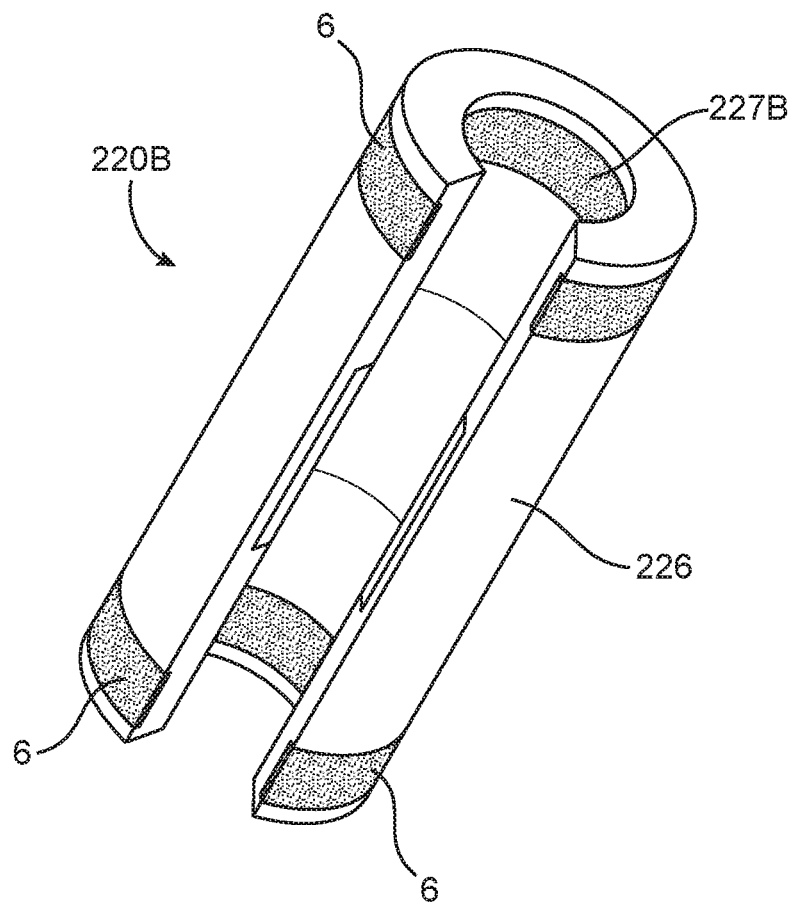
FIG. 72 shows the fully constructed implant of FIG. 71.

Referring to FIGS. 71 and 72, another implant 220B is shown which may be used in the same manner as any of the other implants 220, 220A (including combinations with any of the devices 2A-N described herein) and all such uses are expressly incorporated here. For example, the implant 220B may be positioned with a uterosacral ligament positioned in a throughhole 227B. The implant 220B has a power source 238B which is preferably a capacitor 239 but may be the battery 240 (see FIG. 52) without departing from numerous aspects of the present invention. Battery powered implants, including rechargeable batteries, suffer from several disadvantages. First, battery life is often the limiting factor in implant life. Implants are also often limited in size due to size constraints for many implant applications. Unfortunately, a smaller battery obviously results in a shorter battery life. Rechargeable batteries may extend the life of a conventional implant, however, rechargeable batteries are still limited in the number of recharge cycles they can typically withstand. Replacing the battery (or removing the implant) typically requires another surgical procedure. Finally, batteries also contain potentially toxic materials, complicating the design, manufacture and regulatory tasks for an implantable medical device.

The capacitor 239 may be made of any suitable capacitor materials with more recently developed materials offering high energy densities comparable to a battery. Another advantage of the capacitor 239 is a very high cycle life. One distinct advantage of the capacitor 239 over a rechargeable battery is that the capacitor 239 can be recharged thousands, even tens of thousands, of times. One such material for capacitor 239 is made of layers of graphene and polymer 247. The implant 220B includes an induction element 260, such as an induction coil 262, printed, etched or otherwise deposited or formed on a first flexible substrate 264. The implant 220B has four induction elements 260. A control system 242B is formed on a second substrate 266. The capacitor 239, the control system 242B and an implant body 226 are formed into a roll and bonded together and sandwiched between the nerve stimulating elements 6 to form the implant 220B of FIG. 72. During operation, the control system 242B regulates discharge of the capacitor 239 to power the implant 220B and generate nerve stimulating impulses as described herein. The control system 242B may include switches (not shown) to selectively isolate or couple the induction coil 262 to the capacitor 239 as necessary. In one mode of operation, the capacitor 239 is either being charged or energy is drawn from the capacitor 239 to power the implant 220B. The induction coils 262 are each coupled to a rectifier 267 which supplies DC current to charge the capacitor 239.

The capacitor 239 may also facilitate design of a smaller implant 220B compared to conventional battery-powered implants since some capacitor materials can be recharged tens of thousands of times and, therefore, the capacitor 239 does not require high storage capacity since it can be reliably recharged thousands of times (unlike batteries which can withstand a much more limited number of recharges). To this end, the capacitor 239 may be sized to provide at least 2 days of power under peak operating conditions, and may be no more than 60 days, under peak operating conditions thereby maintaining a small size. Sizing the capacitor 239 in this manner will facilitate design of smaller implants 220B than a comparable battery-operated implant while also providing longer implant life since the capacitor 239 can be recharged many more times than typical rechargeable batteries.

Figure 73:
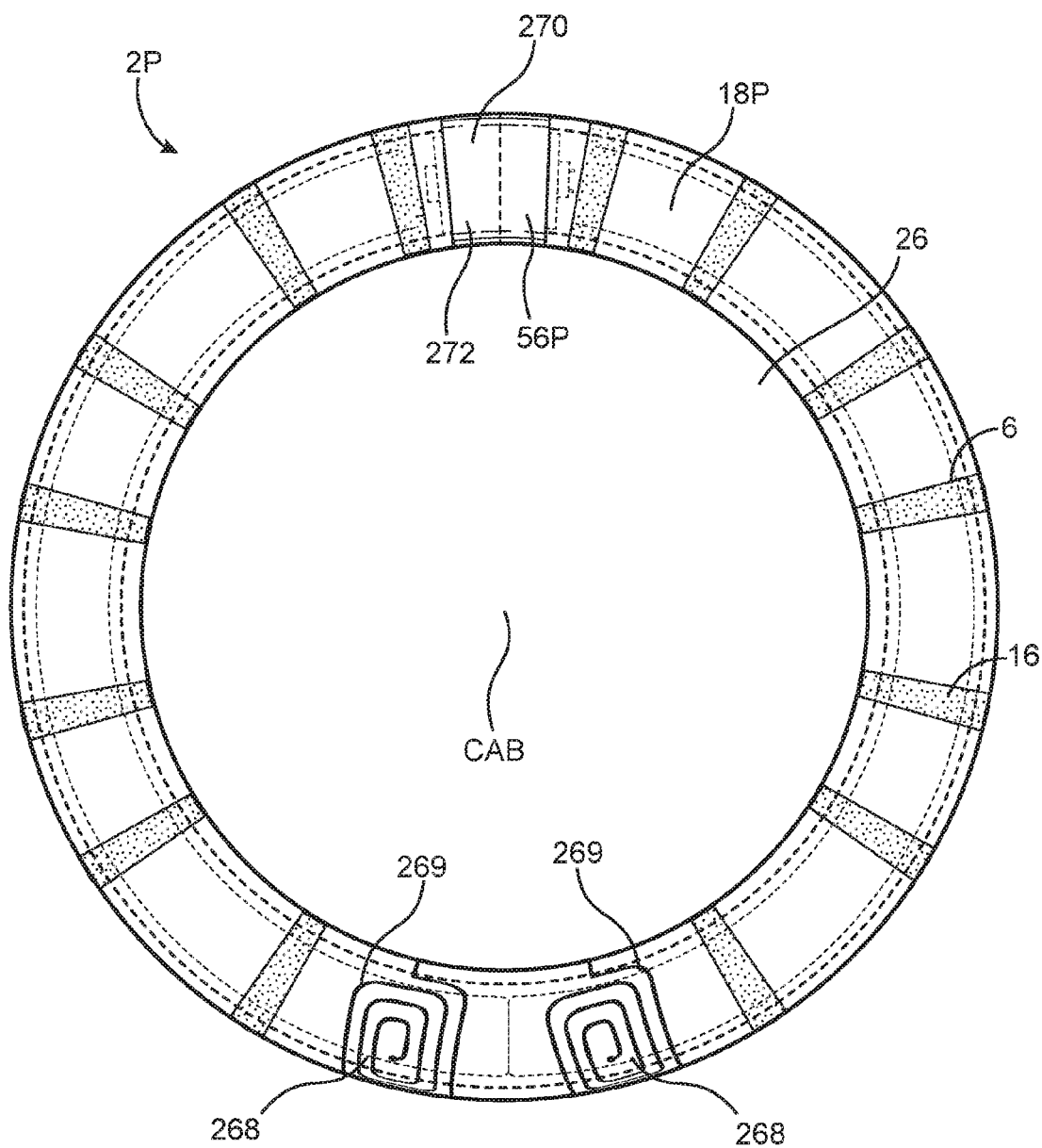
FIG. 73 shows another device which may be positioned in the vagina to stimulate nerves.
Figure 74:
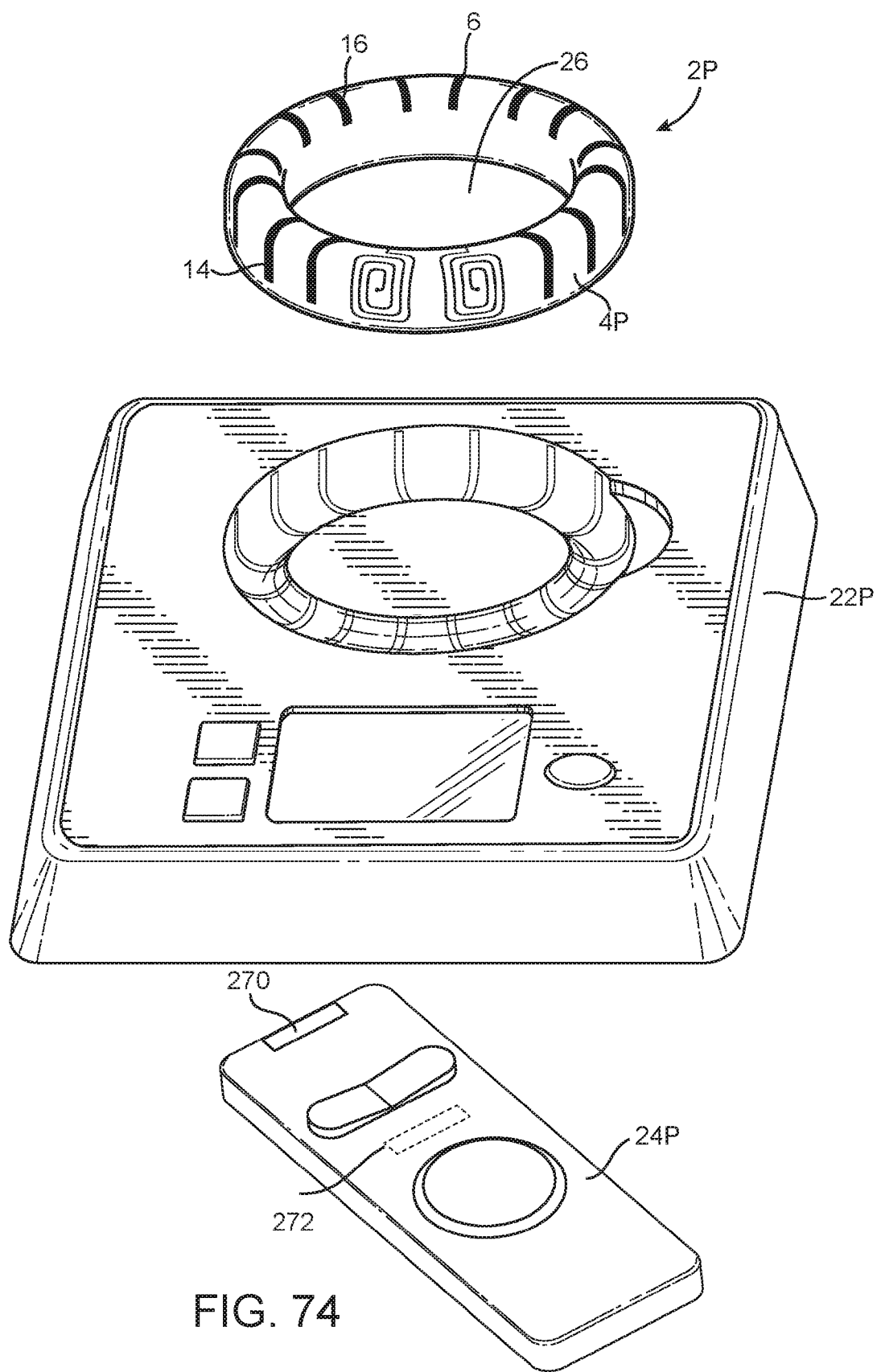
FIG. 74 shows the device of FIG. 73 together with a controller and battery charger for the device.

Referring now to FIGS. 73 and 74, another device 2P designed to be positioned in the vagina (and in particular the vaginal fornices) is shown. The device 2P may also be used to charge the power source 238 of the implant 220B (such as the capacitor 239) of FIGS. 71 and 72 but may be used with any other implanted medical device as well. The device 2P is similar to the devices 2, 2A-N and all uses and aspects of devices 2, 2A-N are incorporated here. The device 2P is similar to the device 2 except that two nerve stimulating elements 6 have each been replaced with a magnetic field creating element 268. The magnetic field creating element 268 includes one or more coils 269 configured to create a magnetic field which impinges on the induction coils 262 of the implant 220B to charge the power source 238. The device 2P also includes nerve stimulating elements 6 which may be used in any manner described herein including all combinations described with the implants 220, 220A, 220B. A control system 18P regulates the current passing through the coils 269 in a conventional manner to provide a fluctuating, pulsing or otherwise changing magnetic field at the induction element 262 of the implant 220B. The induction elements 262 are electrically coupled to the capacitor 239 via contacts 265 on the front and back sides of the capacitor 239. The capacitor 239 is coupled to the implant control system 242B which draws electrical energy from the capacitor 239 and generates and delivers nerve stimulating therapy. The device 2P and control system 18P may operate in any manner described herein. Notably, all target plexuses may still be treated and targeted with the device 2P since adjacent nerve stimulating elements 6 are still capable of stimulating the target locations adjacent the magnetic field creating elements 268.

Figure 75:
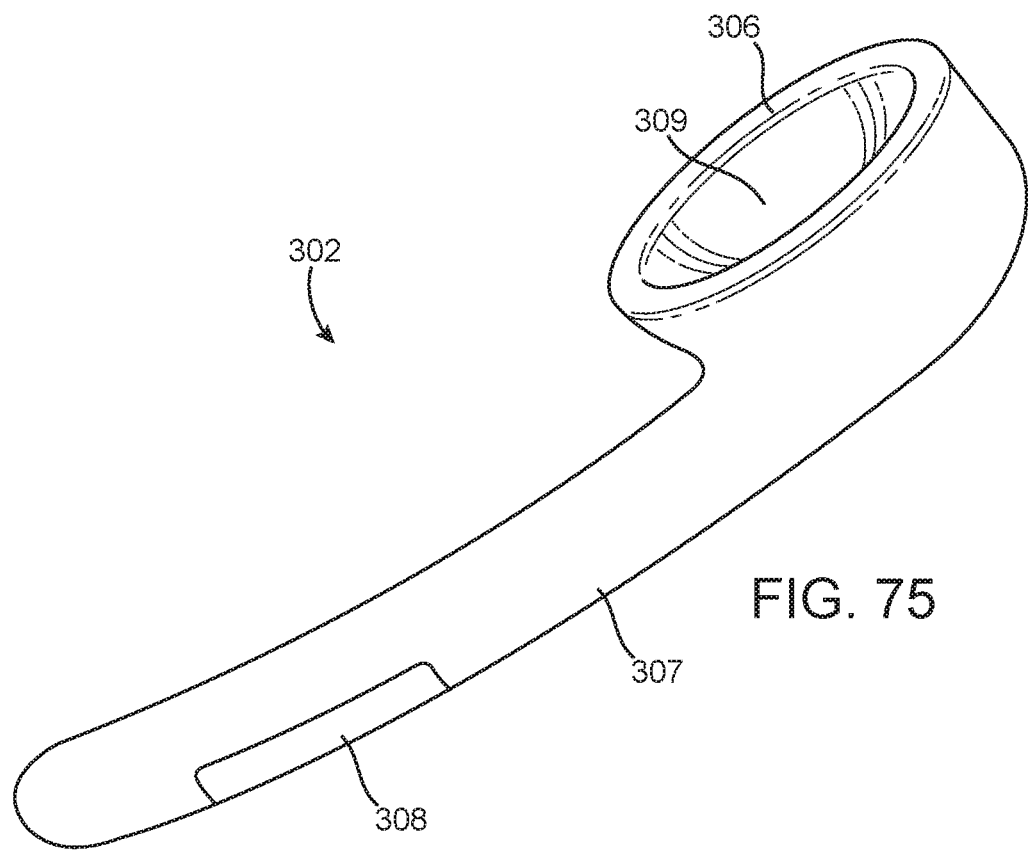
FIG. 75 shows a device for charging a power source for an implant of the present invention.
Figure 76:
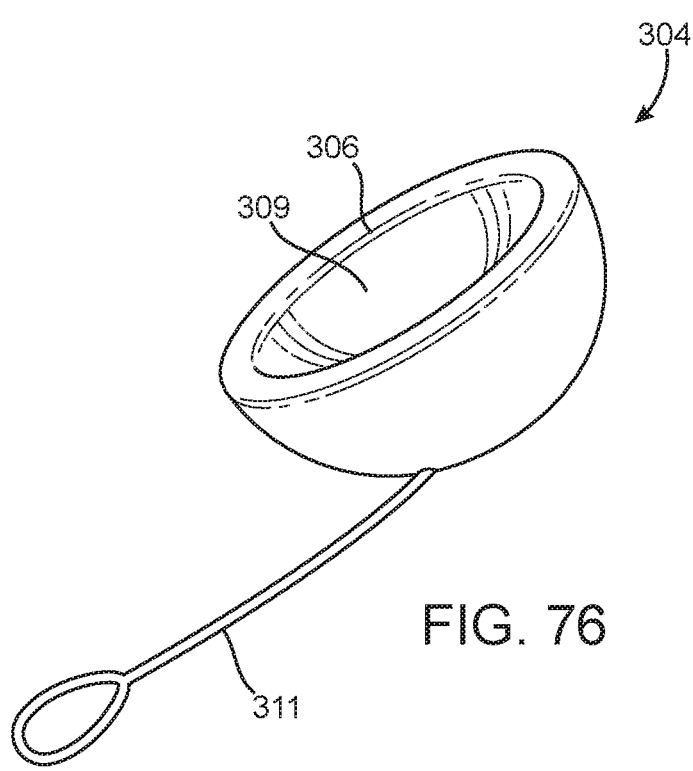
FIG. 76 shows another device for charging a power source for an implant of the present invention.
Figure 77:
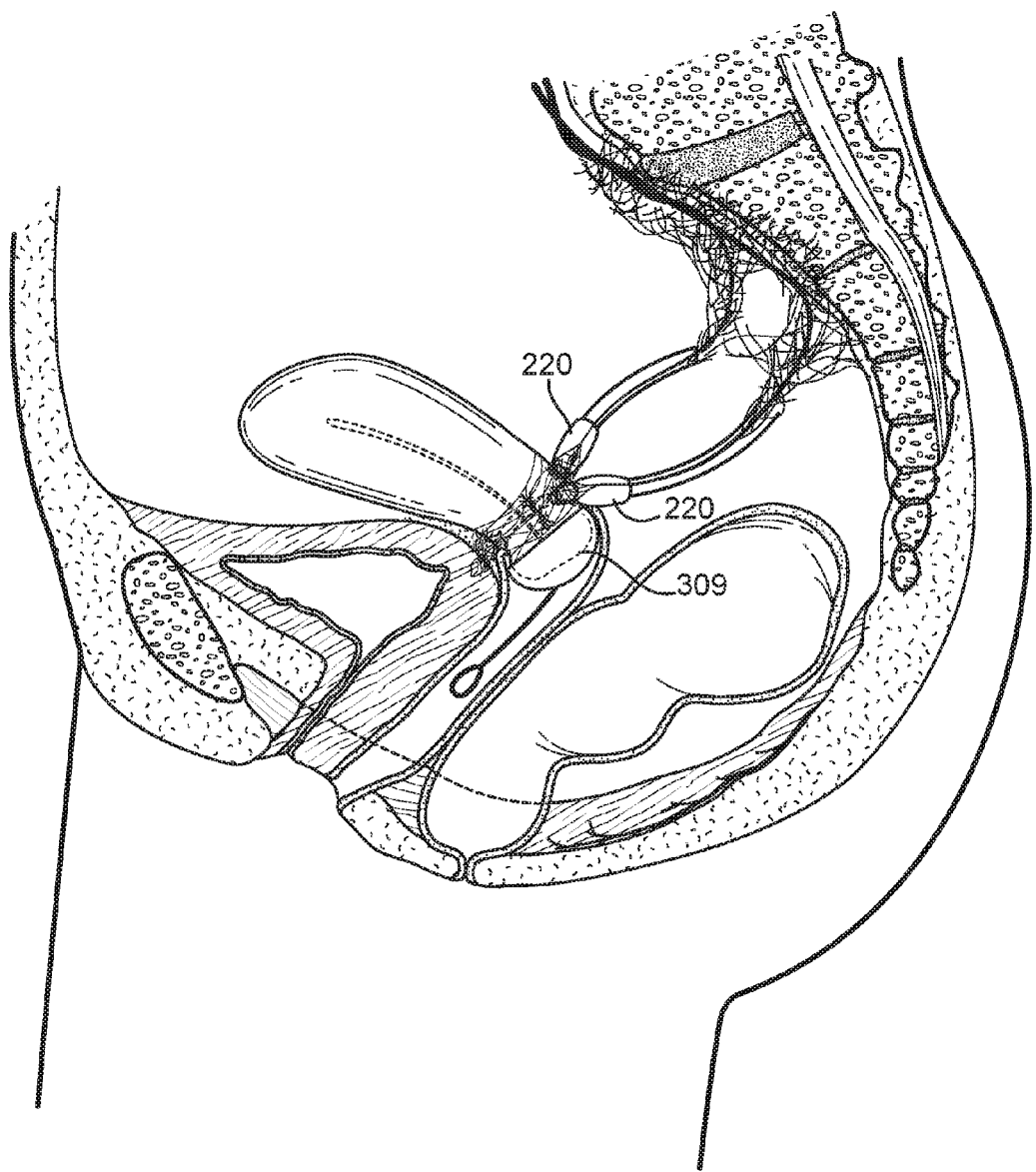
FIG. 77 shows the device of FIG. 76 positioned in the vagina to charge the power sources for two implants each attached to a uterosacral ligament.

The implants 220, 220A, 220B may also be recharged with a separate device rather than using the nerve stimulating devices 2, 2A-P. Referring to FIGS. 75 and 76, a first charger 302 and a second charger 304 are shown. The first and second chargers 302, 304 each include a magnetic field creating element 306 extending around a recess 309. The recess 309 may be part of a throughhole similar to the device 2 or may the recess 309 may be covered at the end of the recess 309 as shown. The first charger 302 has a handle 307 with an actuator 308 to turn the charger on and off. The second charger 304 includes a pull string 311 to aid in removing the second charger 304. The first and second chargers 302, 304 are substantially the same except for shape and the anatomy of the user may dictate which charger 302, 304 is more comfortable for the wearer. FIG. 77 shows the charger 306 in position to charge the power sources for the implants 220.

Referring again to the devices 2, 2A-P, the following discussion relates to methods and devices for confirming that the device 2, 2A-P is in the proper orientation, that is, that the device 2, 2A-P has not shifted so that the nerve stimulating elements 6 have changed position. The devices 2, 2A-2P are initially positioned by the user in a known starting orientation so that the nerve stimulating elements 6 are positioned adjacent their intended targets for stimulation. The marker 81 (see FIG. 9) may be useful when initially positioning and orienting the device 2P. The device 2P (or any of the other devices 2A-P) may also include a procedure to confirm that the device 2P has maintained the starting or intended orientation. To confirm that the device 2P is still positioned as intended, the device 2P is configured to assess the current orientation of device 2P to confirm that the orientation has not changed. The control system 18P may periodically assess the orientation of the device 2P or the user may transmit an instruction to the device 2P using the controller 24P to assess whether the device 2P has moved from the desired orientation relative to the cervix or the CVA. If the orientation has changed, the control system 18P uses the change in orientation information to reassign, as necessary, the nerve stimulating elements (based on the change in orientation) so that the nerve stimulating elements are again positioned adjacent the intended nerves and/or plexus(es) in the known orientation. In this manner, the device 2P may continue to operate normally without the need to reposition the device 2P as would otherwise be necessary.

As mentioned above, the control system 18P may assess the current orientation of the device 2P automatically and reassign the nerve stimulating elements 6 as necessary without user input. In one aspect, the device 2P may include a sensor 270 coupled to the control system 18P for sensing a parameter which relates to the orientation of the device 2P. The control system 18P may sample the same parameter periodically to confirm that the device 2P has not moved. As mentioned above, the parameter may be an electrical signal received at one or more nerve stimulating elements 6 and emitted by another nerve stimulating element 6. Alternatively, the parameter may be another electrophysiological parameter such as tissue impedance or may simply be a measure of native electrical activity. Depending upon the particular parameter selected, the control system 18P may also sense and store the parameter relating to the starting or desired orientation for comparison to the parameter sensed for the current orientation.

Referring to FIG. 74, the sensor 270 is mounted within a hub 56P and positioned at or near the midline 83 (see FIG. 9). The sensor 270 may be an independent element as shown or may be one or more of the nerve stimulating element(s) 6 as mentioned herein without departing from the scope of the invention. In one aspect, the sensor 270 may be configured to sense proximity to an object 272 which may be part of the controller 24P or may be independent of the controller 24P. The sensor 270 may be a magnetic sensor 270 and the object 272 may create a magnetic field which the sensor 270 can remotely sense. The sensor 270 may, of course, operate in any other suitable manner such as a metal sensor 270 for use with the object 272 being metallic, an ultraviolet light sensor which senses UV light emitted by the object 272, or the sensor 270 may be an RF antennae which receives RF signals emitted by the object 272. The object 272 may optionally be worn by the user, for example, the object 272 may be secured to clothing or an accessory (such as a belt) at a predetermined position. When the object is worn or carried by the user at the predetermined location the device 2P may periodically assess orientation automatically.

The object 272 may be carried by the controller 24P. The controller 24P is positioned at the predetermined location relative to the body of the user and the control system 18P is used to transmit an instruction to the device 2P to assess the current orientation of the device 2P. To this end, the user simply positions the controller 24P at the predetermined location, such as the belly button, and the controller 24P is then used to transmit an instruction to the device 2P to assess the orientation of the device 2P. The sensor 270 (such as the magnetic sensor) senses the object 272 and determines the orientation of the device based on the sensed data.

The sensor 270 may be a gravity sensor. Similar to other methods described above, the controller 24P initiates assessing device orientation by using the controller 24P to send an instruction to the device 2P to assess the orientation of the device 2P. Prior to sending the instruction to the device 2P, the user first positions herself in a predetermined body position, such as lying flat on her back. The controller 24P is then used to send a signal to instruct the control system 18P of the device 2P to assess the orientation. At this time, the sensor 270 determines the current orientation of the device 2P. The control system 18P may compare the sensor 270 gravity related data for the current orientation to data (either stored data or sensed and saved data) relating to the starting orientation. To this end, the control system 18P may store data relating to the starting orientation in the same manner. The user will assume the predetermined body position, such as lying down, and then uses the controller 24P to instruct the device 2P to use the sensor 270 to obtain sensor data relating to the starting or intended orientation for comparison to the sensor data relating to the current orientation. The sensor 270 and object 272 may also switch positions with the sensor 270 mounted to the controller 24P and the object 272 mounted to the device 2P. For example, the object 272 may simply be a metallic part of the hub 56P and the sensor 270 may be a metallic sensor 270 mounted to the controller 24P. The controller 24P receives information from the sensor 270 to assess the current orientation of the device 2P. The control system 18P transmits a signal to the device 2P to reassign the nerve stimulating elements 6 in accordance with the current orientation of the device 2P if necessary.

Assessing the orientation of the device 2P may also be accomplished by using one or more of the implants 220, 220A, 220B of the present invention like an internal marker or reference point. When the device 2P and implant 220B are used together, the implant 220B may emit a signal detected by the sensor 270 to assess orientation of the device 2P. The device 2P may also use two or more sensors 270 to triangulate the sensor data. Two or more nerve stimulating elements 6 may also be used to sense the electrical activity of one or more of the implants 220B. The device 2P may sense any suitable parameter relating to electrical activity of the implant 220B.

The control systems 242, 242B of the devices 2, 2A-2N and/or the handheld controller 24 may record data regarding treatment regimens including start and end times, nerve stimulating elements used, resistance, current, frequency, disruption of therapy and any changes made to a regimen. The user will also be able to record subjective and objective information, which will be used to adjust and tailor future regimens to her specific needs. For example, if she has a good response to a certain regimen she may note it at the end of a day or predetermined assessment period. In this case, the regimen will be maintained or she may opt to decrease stimulation intensity towards the threshold of benefit.

The user may also note when she experiences a side effect. By reviewing the treatment regimen (including current, frequency of stimulation, active electrodes and duration of therapy) employed during the time the side effect was experienced, she and her healthcare team will be able to change the stimulation setting or redirect therapy to another target structure altogether.

The user may record experiences using the controller 24 or via free text respond to periodic questions or standardized questionnaires and bladder diaries. All data will be recorded and downloadable to computers and portable devices, such as phones. In one aspect, the user's personal device (ie., phone) may reprogram the controller 24 and alter the regimen. If the patient desires and consents, this objective, subjective and regimen data may be transmitted electronically for remote assessment by healthcare providers or for research purposes.

The present invention may be used to treat a number of different conditions such as urge, frequency, nocturia, urge incontinence, stress incontinence, loss of urine without sensory awareness, bladder pain, urethral pain, urethral syndrome, urinary hesitancy, pelvic floor dyssynergia, interstitial cystitis, dysuria, overactive bladder, urinary retention, hesitancy, protracted urinary stream, dysmenorrhea, pelvic pain, pelvic venous congestion syndrome, endometriosis, irritable bowel syndrome, constipation, fecal urgency, fecal incontinence, rectal pain, pain with defecation, and anal pain. Of course, other uses of the present invention may become apparent without departing from the scope of the invention.

The present invention has been described in connection with preferred embodiments but it is understood that numerous modifications could be made to the preferred embodiments without departing from the scope of the invention. For example, the main body could be V-shaped or the nerve stimulating element could be a coil through which a current is passed to induce a magnetic field without departing from numerous aspects of the present invention.

What is claimed is:

1. An implantable or vaginally inserted system for stimulating nerves, comprising:
   a first body having an exterior surface;
   a first nerve stimulating element coupled to the first body;
   a first power source coupled to the first body; and
   a first control system coupled to the first power source and the first nerve stimulating element;
   the first power source being coupled to the first control system, the first power source being a capacitor sized to provide at least 2 days of power to operate under peak operating conditions.

2. An implantable or vaginally inserted system for stimulating nerves, comprising:
   a first body having an exterior surface;
   a first nerve stimulating element coupled to the first body;
   a first power source coupled to the first body; and
   a first control system coupled to the first power source and the first nerve stimulating element;
   the first power source is coupled to the first control system, the first power source being a capacitor sized to provide no more than 60 days of power for under peak operating conditions.

* * * * *